United States Patent

Rogier, Jr. et al.

(10) Patent No.: US 6,822,102 B2
(45) Date of Patent: Nov. 23, 2004

(54) DIHYDROBENZOPYRANS, DIHYDROBENZOTHIOPYRANS, AND TETRAHYDROQUINOLINES FOR THE TREATMENT OF COX-2 MEDIATED DISORDERS

(75) Inventors: Donald Rogier, Jr., Kalamazoo, MI (US); Jeffery Carter, Chesterfield, MO (US); John Talley, Cambridge, MA (US)

(73) Assignee: Pharmacia Corporation, St. Louis, MO (US)

( * ) Notice: Subject to any disclaimer, the term of this patent is extended or adjusted under 35 U.S.C. 154(b) by 0 days.

(21) Appl. No.: 10/169,443
(22) PCT Filed: Dec. 19, 2000
(86) PCT No.: PCT/US00/34525
§ 371 (c)(1),
(2), (4) Date: Oct. 15, 2002
(87) PCT Pub. No.: WO01/49675
PCT Pub. Date: Jul. 12, 2001

(65) Prior Publication Data

US 2003/0232844 A1 Dec. 18, 2003

Related U.S. Application Data

(60) Provisional application No. 60/174,281, filed on Jan. 3, 2000.

(51) Int. Cl.$^7$ .................. C07D 319/14; A61K 31/425
(52) U.S. Cl. .................................. 549/366; 514/457
(58) Field of Search ........................ 514/457; 549/366

(56) References Cited

U.S. PATENT DOCUMENTS 6,077,850 A * 6/2000 Carter et al. ................ 514/311

FOREIGN PATENT DOCUMENTS

| DE | 19638484 | * | 3/1998 |
| EP | 0 924 207 | * | 6/1999 |
| WO | WO 98/47890 | * | 10/1998 |
| WO | WO 00/23433 | * | 4/2000 |

OTHER PUBLICATIONS

Jayaram, CA 115:256033, abstract of Indian Journal of Chemistry, Sction B: Organic Chemistry, vol. 29B(8), pp 707–710, 1990.*

Adegoke, CA 109:149291, abstract of J of Heterocyclic Chemistry, vol. 24(6), 1705–1708, 1987.*

Korte, CA 54:97560, abstract of Chemische Berichte, vol. 93, 1025–1033, 1960.*

* cited by examiner

Primary Examiner—D. Margaret Seaman
(74) Attorney, Agent, or Firm—Julie M. Lappin; James M. Warner

(57) ABSTRACT

A class of dihydrobenzopyrans, dihydrobenzothiopyrans, tetrahydroquinolines, tetrahydronaphthalenes, and analogs thereof, is described for use in treating cyclooxygenase-2 mediated disorders. Compounds of particular interest are defined by Formula (I) wherein X, $A^1$, $A^2$, $A^3$, $A^4$, R, R", $R^1$ and $R^2$ are as described in the specification

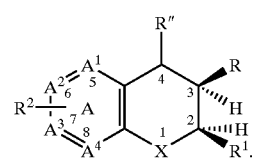

15 Claims, No Drawings

DIHYDROBENZOPYRANS, DIHYDROBENZOTHIOPYRANS, AND TETRAHYDROQUINOLINES FOR THE TREATMENT OF COX-2 MEDIATED DISORDERS

This application claims the benefit of provisional application No. 60/174,281 filed on Jan. 3, 2000.

FIELD OF THE INVENTION

This invention is in the field of anti-inflammatory pharmaceutical agents and specifically relates to compounds, compositions and methods for treating cyclooxygenase-2 mediated disorders, such as inflammation and inflammation-related disorders.

BACKGROUND OF THE INVENTION

Prostaglandins play a major role in the inflammation process and the inhibition of prostaglandin production, especially production of $PGG_2$, $PGH_2$ and $PGE_2$, has been a common target of antiinflammatory drug discovery. However, common non-steroidal antiinflammatory drugs (NSAIDs) that are active in reducing the prostaglandin-induced pain and swelling associated with the inflammation process are also active in affecting other prostaglandin-regulated processes not associated with the inflammation process. Thus, use of high doses of most common NSAIDs can produce severe side effects, including life threatening ulcers, that limit their therapeutic potential. An alternative to NSAIDs is the use of corticosteroids, which have even more drastic side effects, especially when long term therapy is involved.

Previous NSAIDs have been found to prevent the production of prostaglandins by inhibiting enzymes in the human arachidonic acid/prostaglandin pathway, including the enzyme cyclooxygenase (COX). The recent discovery of an inducible enzyme associated with inflammation (named "cyclooxygenase-2 (COX-2)" or "prostaglandin G/H synthase II") provides a viable target of inhibition which more effectively reduces inflammation and produces fewer and less drastic side effects.

Recently, there has been significant research into some of the roles of cyclooxygenase-2. It has been found that COX-2 is upregulated in benign and malignant tumors (K. Subbaramaiah et al., Proc. Soc. Exp. Biol. Med., 216, 201 (1997)) including lung cancer (T. Hida et al., Anticancer Res., 18, 775–82 (1998)), Barrett's esophagus (K. Wilson, Cancer Res., 58, 2929–34 (1998)) and skin cancer (S. Buckman et al., Carcinogenesis, 19, 723–29 (1998)). It is expressed in airway cells with implication in asthma (P. Barnes et al., Lung Biol. Health Dis., 114, 111–27 (1998)). Cox-2 also has a role in pre-term labor, angiogenesis (M. Tsujii et al. Cell, 93, 705–16 (1998)), vascular rejection (M. Bustos, J. Clin. Invest., 100, 1150–58 (1997)), HIV induced apoptosis (G. Bagetta et al., Biochem. Biophys. Res. Commun., 244, 819–24 (1998)), neurodegeneration (T. Sandhya et al., Brain Res., 788, 223–31 (1998)), inflammatory bowel disease, colitis, (I. Singer et al., Gastroenterology, 115, 297–306 (1998)), cerebral ischemia (S. Nogawa et al., Proc. Natl. Acad. Sci., 95, 10966–71 (1998)), hypertension (A. Nasjletti, Hypertension, 31, 194–200 (1997)), among others.

Drugs that inhibit cyclooxygenase affect colon cancer (T. Kawamori et al., Cancer Res., 58, 409–12 (1998)), allergic neuritis (K. Miyamoto et al., Neuro Report, 9, 2331–4 (1998)), dementia, burn infections (M. Shoup, J. Trauma: Inj., Infec., Crit care, 45, 215–21 (1998)), cytomegalovirus infectivity (E. Speir et al., Circ. Res., 83, 210–16 (1998)), lumbago (H. Bosch, Curr. Med. Res. Opin., 14, 29–38 (1997)), among others.

Japanese Patent No. 6166813 describes dihydrobenzopyrans as plastic additives. Japanese Patent No. 5032591 describes bicyclic compounds for preparing coloring materials. EP publication 736529, published Oct. 9, 1996, describes 2,2-dimethyldihydrobenzopyrans as reagents for immunoassay. U.S. Pat. No. 5,773,203, issued Jun. 30, 1998, describes tetrahydroquinoline compounds for color imagining agents. Japanese patent 10069044 describes tetrahydroquinolines as color agents. Japanese patent 10062926 describes tetrahydroquinolines as color agents. Japanese patent 10062929 describes tetrahydroquinolines as color agents. U.S. Pat. No. 5,120,862, issued Jun. 9, 1992, describes tetrahydronaphthalene carboxylic acids as intermediates. Japanese publication 4009959 describes the use of dihydrothiobenzopyrans as photographic agents. WO98/29386, published Jul. 9, 1998, describes sulfonyl substituted dihydrobenzopyran derivatives as linkers. EP670312, published Sep. 6, 1995, describes tetrahydroquinolines as color developing agents. WO98/12192 describes tetrahydroquinolines as herbicides. WO98/12180 describes tetrahydroquinolines as herbicides.

U.S. Pat. No. 4,954,518, issued Sep. 4, 1990, describes benzopyran-ones for the treatment of inflammation. EP publication 695547, published Feb., 7, 1996, describes benzopyran-ones as immunomodulators. Japanese patent 6128155 describes antiinflammatory benzopyranones. Japanese patent 5178745 describes antiinflammatory benzopyranones. Japanese publication 6227971 describes amidine derivatives as antiviral agents. Japanese publication 8020532 describes amidine derivatives as pancreatitis agents. U.S. Pat. No. 5,639,911 describes amidino compounds for the treatment of cancer. U.S. Pat. No. 5,620,991 describes amidino compounds as factor Xa inhibitors. U.S. Pat. No. 5,462,965, issued Oct. 31, 1995, describes amino alcohols for treatment of CNS disease. EP 363883 describes chroman derivatives for the treatment of carrdiovascular disease. U.S. Pat. No. 4,777,257 describes tetrahydronaphthyl acid derivatives for the inhibition of thromboxane.

U.S. Pat. No. 5,731,324, issued Mar. 24, 1998, describes benzopyran derivatives as platelet aggregation inhibitors. U.S. Pat. No. 5,618,843 describes tetrahydronaphthalene derivatives as anti-platelet agents. PCT publication WO98/08836, published Mar. 5, 1998, describes chromene-3-carboxylic acid analogs as endothelin antagonists. PCT publication WO95/04530, published Feb. 16, 1995, describes tetrahydronaphthalene analogs as endothelin antagonists. PCT publication WO98/38992, published Sep. 11, 1998, describes benzopyran analogs as remedies for peripheral circulation disturbances. U.S. Pat. No. 5,112,972, issued May 12, 1992, describes chroman derivatives for the treatment of cardiovascular disease. U.S. Pat. No. 5,387,587, issued Feb. 7, 1995, describes chroman derivatives for the treatment of cardiovascular disease. PCT publication WO96/15099, published May 23, 1996, describes tetrahydronaphthalene carboxylic acid analogs as glutamate receptor agonist/antagonists. U.S. Pat. No. 5,124,325, issued Jun. 23, 1992, describes tetrahydroquinoline-8-carboxylic acid derivatives as agents to treat metabolic bone disease. Japanese publication 9255660 describes the use of tetrahydoquinolines for the treatment of vessel wall hypertrophy inhibitors. WO93/14066 describes sulfonamide amino acid derivatives as CCK antagonists.

U.S. Pat. No. 4,889,871, issued Dec. 26, 1989, describes dihydrobenzopyran derivatives as leukotriene inhibitors.

U.S. Pat. No. 5,281,600, issued Jan. 25, 1994, describes tetrahydroquinoline-8-carboxylic acid derivatives as antirheumatoid agents. WO93/15067 describes 4-hydroxy-dihydrobenzopyrans as LTB$_4$ antagonists. U.S. Pat. No. 5,242,912, issued Sep. 7, 1993, describes tetrahydroquinoline carboxylic acid derivatives as antirheumatoid agents. WO88/03805, published Jun. 2, 1988, describes tetrahydronaphthalenes for the treatment of cancer. U.S. Pat. No. 5,698,550 describes chroman derivatives as 5-lipoxygenase inhibitors. U.S. Pat. No. 5,552,441 describes leukotriene B4 antagonists.

The references below that disclose antiinflammatory activity, show continuing efforts to find a safe and effective antiinflammatory agent. The novel dihydrobenzopyran, tetrahydroquinoline, dihydrobenzothiopyran and tetrahydronapthalene derivatives disclosed herein are such safe and also effective antiinflammatory agents furthering such efforts.

However, compounds of the current invention have not been described as antiinflammatory cyclooxygenase-2 inhibitors.

DESCRIPTION OF THE INVENTION

A class of compounds useful in treating cyclooxygenase-2 mediated disorders is defined by Formula I

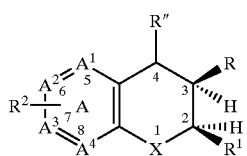

I wherein X is selected from O, S, CR$^c$R$^b$ and NR$^a$;

wherein R$^a$ is selected from hydrido, C$_1$–C$_3$-alkyl, phenyl-C$_1$–C$_3$-alkyl, (substituted phenyl)-C$_1$–C$_3$-alkyl, C$_1$–C$_3$-alkoxycarbonyl-C$_1$–C$_3$-alkyl and carboxy-C$_1$–C$_6$-alkyl;

wherein each of R$^b$ and R$^c$ is independently selected from hydrido, C$_1$–C$_3$-alkyl, substituted or unsubstituted phenyl-C$_1$–C$_3$-alkyl, C$_1$–C$_3$-perfluoroalkyl, chloro, C$_1$–C$_6$-alkylthio, C$_1$–C$_6$-alkoxy, nitro, cyano and cyano-C$_1$–C$_3$-alkyl; or wherein CR$^b$R$^c$ forms a 3–6 membered cycloalkyl ring;

wherein R is selected from carboxyl, aminocarbonyl, C$_1$–C$_6$-alkylsulfonylaminocarbonyl and C$_1$–C$_6$-alkoxycarbonyl;

wherein R" is selected from hydrido, phenyl, thienyl, C$_1$–C$_6$-alkyl and C$_2$–C$_6$-alkenyl;

wherein R$^1$ is selected from C$_1$–C$_3$-perfluoroalkyl, chloro, C$_1$–C$_6$-alkylthio, C$_1$–C$_6$-alkoxy, nitro, cyano and cyano-C$_1$–C$_3$-alkyl;

wherein R$^2$ is one or more radicals independently selected from hydrido, halo, C$_1$–C$_6$-alkyl, C$_2$–C$_6$-alkenyl, C$_2$–C$_6$-alkynyl, halo-C$_2$–C$_6$-alkynyl, aryl-C$_1$–C$_3$-alkyl, aryl-C$_2$–C$_6$-alkynyl, aryl-C$_1$–C$_6$-alkenyl, C$_1$–C$_6$-alkoxy, methylenedioxy, C$_1$–C$_6$-alkylthio, C$_1$–C$_6$-alkylsulfinyl, aryloxy, arylthio, arylsulfinyl, heteroaryloxy, C$_1$–C$_6$-alkoxy-C$_1$–C$_6$-alkyl, aryl-C$_1$–C$_6$-alkoxy, heteroaryl-C$_1$–C$_6$-alkoxy, aryl-C$_1$–C$_6$-alkoxy-C$_1$–C$_6$-alkyl, C$_1$–C$_6$-haloalkyl, C$_1$–C$_6$-haloalkoxy, C$_1$–C$_6$-haloalkylthio, C$_1$–C$_6$-haloalkylsulfinyl, C$_1$–C$_6$-haloalkylsulfonyl, C$_1$–C$_3$-(haloalkyl)-C$_1$–C$_3$-hydroxyalkyl, C$_1$–C$_6$-hydroxyalkyl, hydroxyimino-C$_1$–C$_6$-alkyl, C$_1$–C$_6$-alkylamino, arylamino, N-aryl-N—C$_1$–C$_6$-alkylamino, heteroarylamino, N-heteroaryl-N—C$_1$–C$_6$-alkylamino, nitro, cyano, amino, aminosulfonyl, C$_1$–C$_6$-alkylaminosulfonyl, arylaminosulfonyl, heteroarylaminosulfonyl, N-aryl-C$_1$–C$_6$-alkylaminosulfonyl, N-heteroaryl-C$_1$–C$_6$-alkylaminosulfonyl, heterocyclylsulfonyl, C$_1$–C$_6$-alkylsulfonyl, aryl-C$_1$–C$_6$-alkylsulfonyl, optionally substituted aryl, optionally substituted heteroaryl, aryl-C$_1$–C$_6$-alkylcarbonyl, heteroaryl-C$_1$–C$_6$-alkylcarbonyl, heteroarylcarbonyl, arylcarbonyl, aminocarbonyl, C$_1$–C$_6$-alkoxycarbonyl, formyl, C$_1$–C$_6$-haloalkylcarbonyl and C$_1$–C$_6$-alkylcarbonyl; and wherein the A ring atoms A$^1$, A$^2$, A$^3$ and A$^4$ are independently selected from carbon and nitrogen with the proviso that at least two of A$^1$, A$^2$, A$^3$ and A$^4$ are carbon;

or wherein R$^2$ together with ring A forms a radical selected from naphthyl, quinolyl, isoquinolyl, quinolizinyl, quinoxalinyl and dibenzofuryl;

or an isomer or pharmaceutically acceptable salt thereof.

Compounds of the present invention would be useful for, but not limited to, the treatment of inflammation in a subject, and for treatment of other cyclooxygenase-2 mediated disorders, such as, as an analgesic in the treatment of pain and headaches, or as an antipyretic for the treatment of fever. For example, compounds of the invention would be useful to treat arthritis, including but not limited to rheumatoid arthritis, spondyloarthropathies, gouty arthritis, osteoarthritis, systemic lupus erythematosus and juvenile arthritis. Such compounds of the invention would be useful in the treatment of asthma, bronchitis, menstrual cramps, preterm labor, tendinitis, bursitis, allergic neuritis, cytomegalovirus infectivity, apoptosis including HIV induced apoptosis, lumbago, liver disease including hepatitis, skin-related conditions such as psoriasis, eczema, acne, UV damage, burns and dermatitis, and post-operative inflammation including ophthalmic surgery such as cataract surgery and refractive surgery. Compounds of the invention also would be useful to treat gastrointestinal conditions such as inflammatory bowel disease, Crohn's disease, gastritis, irritable bowel syndrome and ulcerative colitis. Compounds of the invention would be useful in treating inflammation in such diseases as migraine headaches, periarteritis nodosa, thyroiditis, aplastic anemia, Hodgkin's disease, sclerodoma, rheumatic fever, type I diabetes, neuromuscular junction disease including myasthenia gravis, white matter disease including multiple sclerosis, sarcoidosis, nephrotic syndrome, Behcet's syndrome, polymyositis, gingivitis, nephritis, hypersensitivity, swelling occurring after injury including brain edema, myocardial ischemia, and the like. The compounds would also be useful in the treatment of ophthalmic diseases, such as retinitis, conjunctivitis, retinopathies, uveitis, ocular photophobia, and of acute injury to the eye tissue. The compounds would also be useful in the treatment of pulmonary inflammation, such as that associated with viral infections and cystic fibrosis, and in bone reorption such as associated with osteoporosis.

The compounds would also be useful for the treatment of certain central nervous system disorders, such as cortical dementias including Alzheimer's disease, neurodegeneration, and central nervous system damage resulting from stroke, ischemia and trauma. The term "treatment" includes partial or total inhibition of the dementia, including Alzheimer's disease, vascular dementia, multi-infarct dementia, pre-senile dementia, alcoholic dementia, and senile dementia.

The compounds of the invention are useful as anti-inflammatory agents, such as for the treatment of arthritis, with the additional benefit of having significantly less harmful side effects. These compounds would also be useful in the treatment of allergic rhinitis, respiratory distress syndrome, endotoxin shock syndrome, and liver disease. The compounds would also be useful in the treatment of pain, but not limited to postoperative pain, dental pain, muscular pain, and pain resulting from cancer.

The method above would be useful for, but not limited to, treating and preventing inflammation-related cardiovascular disorders in a subject. The method would be useful for treatment and prevention of vascular diseases, coronary artery disease, aneurysm, vascular rejection, arteriosclerosis, atherosclerosis including cardiac transplant atherosclerosis, myocardial infarction, embolism, stroke, thrombosis, including venous thrombosis, angina including unstable angina, coronary plaque inflammation, bacterial-induced inflammation including Chlamydia-induced inflammation, viral induced inflammation, and inflammation associated with surgical procedures such as vascular grafting including coronary artery bypass surgery, revascularization procedures including angioplasty, stent placement, endarterectomy, or other invasive procedures involving arteries, veins and capillaries.

The compounds would be useful for, but not limited to, the treatment of angiogenesis-related disorders in a subject. According to the present invention, the compounds can be administered to a subject in need of angiogenesis inhibition. The method would be useful for treatment of neoplasia, including metastasis; ophthalmological conditions such as corneal graft rejection, ocular neovascularization, retinal neovascularization including neovascularization following injury or infection, diabetic retinopathy, macular degeneration, retrolental fibroplasia and glaucoma; ulcerative diseases such as gastric ulcer; pathological, but non-malignant, conditions such as hemangiomas, including invantile hemaginomas, angiofibroma of the nasopharynx and avascular necrosis of bone; and disorders of the female reproductive system such as endometriosis.

Compounds of the invention would be useful for the prevention or treatment of benign and malignant tumors/neoplasia including cancer, such as colorectal cancer, brain cancer, bone cancer, epithelial cell-derived neoplasia (epithelial carcinoma) such as basal cell carcinoma, adenocarcinoma, gastrointestinal cancer such as lip cancer, mouth cancer, esophogeal cancer, small bowel cancer and stomach cancer, colon cancer, liver cancer, bladder cancer, pancreas cancer, ovary cancer, cervical cancer, lung cancer, breast cancer and skin cancer, such as squamus cell and basal cell cancers, prostate cancer, renal cell carcinoma, and other known cancers that effect epithelial cells throughout the body. Preferably, neoplasia is selected from gastrointestinal cancer, Barrett's esophagus, liver cancer, bladder cancer, pancreas cancer, ovary cancer, prostate cancer, cervical cancer, lung cancer, breast cancer and skin cancer, such as squamus cell and basal cell cancers. The compounds can also be used to treat the fibrosis which occurs with radiation therapy. The method can be used to treat subjects having adenomatous polyps, including those with sporadic adenomatous polyposis (SAP) or familial adenomatous polyposis (FAP). Additionally, the method can be used to prevent polyps from forming in patients at risk of FAP.

The administration of compounds of the present invention may be used alone or in conjunction with additional therapies known to those skilled in the art in the prevention or treatment of neoplasia. Alternatively, the compounds described herein may be used in conjunctive therapy. By way of example, the compounds may be administered alone or in conjunction with other antineoplastic agents or other growth inhibiting agents or other drugs or nutrients.

There are large numbers of antineoplastic agents available in commercial use, in clinical evaluation and in pre-clinical development, which could be selected for treatment of neoplasia by combination drug chemotherapy. Such antineoplastic agents fall into several major categories, namely, antibiotic-type agents, alkylating agents, antimetabolite agents, hormonal agents, immunological agents, interferon-type agents and a category of miscellaneous agents. Alternatively, other anti-neoplastic agents, such as metallo-matrix proteases (MMP), SOD mimics or $\alpha_v\beta_3$ inhibitors may be used.

A first family of antineoplastic agents which may be used in combination with compounds of the present invention consists of antimetabolite-type antineoplastic agents. Suitable antimetabolite antineoplastic agents may be selected from the group consisting of 5-FU-fibrinogen, acanthifolic acid, aminothiadiazole, brequinar sodium, carmofur, Ciba-Geigy CGP-30694, cyclopentyl cytosine, cytarabine phosphate stearate, cytarabine conjugates, Lilly DATHF, Merrel Dow DDFC, dezaguanine, dideoxycytidine, dideoxyguanosine, didox, Yoshitomi DMDC, doxifluridine, Wellcome EHNA, Merck & Co. EX-015, fazarabine, floxuridine, fludarabine phosphate, 5-fluorouracil, N-(2'-furanidyl)-5-fluorouracil, Daiichi Seiyaku FO-152, isopropyl pyrrolizine, Lilly LY-188011, Lilly LY-264618, methobenzaprim, methotrexate, Wellcome MZPES, norspermidine, NCI NSC-127716, NCI NSC-264880, NCI NSC-39661, NCI NSC-612567, Warner-Lambert PALA, pentostatin, piritrexim, plicamycin, Asahi Chemical PL-AC, Takeda TAC-788, thioguanine, tiazofurin, Erbamont TIF, trimetrexate, tyrosine kinase inhibitors, tyrosine protein kinase inhibitors, Taiho UFT and uricytin.

A second family of antineoplastic agents which may be used in combination with compounds of the present invention consists of alkylating-type antineoplastic agents. Suitable alkylating-type antineoplastic agents may be selected from the group consisting of Shionogi 254-S, aldophosphamide analogues, altretamine, anaxirone, Boehringer Mannheim BBR-2207, bestrabucil, budotitane, Wakunaga CA-102, carboplatin, carmustine, Chinoin-139, Chinoin-153, chlorambucil, cisplatin, cyclophosphamide, American Cyanamid CL-286558, Sanofi CY-233, cyplatate, Degussa D-19-384, Sumimoto DACHP (Myr)2, diphenylspiromustine, diplatinum cytostatic, Erba distamycin derivatives, Chugai DWA-2114R, ITI E09, elmustine, Erbamont FCE-24517, estramustine phosphate sodium, fotemustine, Unimed G-6-M, Chinoin GYKI-17230, hepsulfam, ifosfamide, iproplatin, lomustine, mafosfamide, mitolactol, Nippon Kayaku NK-121, NCI NSC-264395, NCI NSC-342215, oxaliplatin, Upjohn PCNU, prednimustine, Proter PTT-119, ranimustine, semustine, SmithKline SK&F-101772, Yakult Honsha SN-22, spiromus-tine, Tanabe Seiyaku TA-077, tauromustine, temozolomide, teroxirone, tetraplatin and trimelamol.

A third family of antineoplastic agents which may be used in combination with compounds of the present invention consists of antibiotic-type antineoplastic agents. Suitable antibiotic-type antineoplastic agents may be selected from the group consisting of Taiho 4181-A, aclarubicin, actinomycin D, actinoplanone, Erbamont ADR-456, aeroplysinin derivative, Ajinomoto AN-201-II, Ajinomoto AN-3, Nippon Soda anisomycins, anthracycline, azino-mycin-A, bisucaberin, Bristol-Myers BL-6859, Bristol-Myers BMY-25067, Bristol-Myers BMY-25551, Bristol-Myers BMY-26605, Bristol-Myers BMY-27557, Bristol-Myers BMY-28438, bleomycin sulfate, bryostatin-1, Taiho C-1027, calichemycin, chromoximycin, dactinomycin, daunorubicin, Kyowa Hakko DC-102, Kyowa Hakko DC-79, Kyowa Hakko DC-88A, Kyowa Hakko DC89-A1, Kyowa Hakko DC92-B, ditrisarubicin B, Shionogi DOB-41, doxorubicin, doxorubicin-fibrinogen, elsamicin-A, epirubicin, erbstatin, esorubicin, esperamicin-A1, esperamicin-A1b, Erbamont FCE-21954, Fujisawa FK-973, fostriecin, Fujisawa FR-900482, glidobactin, gregatin-A, grincamycin, herbimycin, idarubicin, illudins, kazusamycin, kesarirhodins, Kyowa Hakko KM-5539, Kirin Brewery KRN-8602, Kyowa Hakko KT-5432, Kyowa Hakko KT-5594, Kyowa Hakko KT-6149, American Cyanamid LL-D49194, Meiji Seika ME 2303, menogaril, mitomycin, mitoxantrone, SmithKline M-TAG, neoenactin, Nippon Kayaku NK-313, Nippon Kayaku NKT-01, $SR^1$ International NSC-357704, oxalysine, oxaunomycin, peplomycin, pilatin, pirarubicin, porothramycin, pyrindamycin A, Tobishi RA-I, rapamycin, rhizoxin, rodorubicin, sibanomicin, siwenmycin, Sumitomo SM-5887, Snow Brand SN-706, Snow Brand SN-07, sorangicin-A, sparsomycin, SS Pharmaceutical SS-21020, SS Pharmaceutical SS-7313B, SS Pharmaceutical SS-9816B, steffimycin B, Taiho 4181-2, talisomycin, Takeda TAN-868A, terpentecin, thrazine, tricrozarin A, Upjohn U-73975, Kyowa Hakko UCN-10028A, Fujisawa WF-3405, Yoshitomi Y-25024 and zorubicin.

A fourth family of antineoplastic agents which may be used in combination with compounds of the present invention consists of a miscellaneous family of antineoplastic agents selected from the group consisting of alpha-carotene, alpha-difluoromethyl-arginine, acitretin, Biotec AD-5, Kyorin AHC-52, alstonine, amonafide, amphethinile, amsacrine, Angiostat, ankinomycin, anti-neoplaston A10, antineoplaston A2, antineoplaston A3, antineoplaston A5, antineoplaston AS2-1, Henkel APD, aphidicolin glycinate, asparaginase, Avarol, baccharin, batracylin, benfluron, benzotript, Ipsen-Beaufour BIM-23015, bisantrene, Bristo-Myers BMY-40481, Vestar boron-10, bromofosfamide, Wellcome BW-502, Wellcome BW-773, caracemide, carmethizole hydrochloride, Ajinomoto CDAF, chlorsulfaquinoxalone, Chemes CHX-2053, Chemex CHX-100, Warner-Lambert CI-921, Warner-Lambert CI-937, Warner-Lambert CI-941, Warner-Lambert CI-958, clanfenur, claviridenone, ICN compound 1259, ICN compound 4711, Contracan, Yakult Honsha CPT-11, crisnatol, curaderm, cytochalasin B, cytarabine, cytocytin, Merz D-609, DABIS maleate, dacarbazine, datelliptinium, didemnin-B, dihaematoporphyrin ether, dihydrolenperone, dinaline, distamycin, Toyo Pharmar DM-341, Toyo Pharmar DM-75, Daiichi Seiyaku DN-9693, elliprabin, elliptinium acetate, Tsumura EPMTC, ergotamine, etoposide, etretinate, fenretinide, Fujisawa FR-57704, gallium nitrate, genkwadaphnin, Chugai GLA-43, Glaxo GR-63178, grifolan NMF-5N, hexadecylphosphocholine, Green Cross HO-221, homoharringtonine, hydroxyurea, BTG ICRF-187, ilmofosine, isoglutamine, isotretinoin, Otsuka JI-36, Ramot K-477, Otsuak K-76COONa, Kureha Chemical K-AM, MECT Corp KI-8110, American Cyanamid L-623, leukoregulin, lonidamine, Lundbeck LU-23-112, Lilly LY-186641, NCI (US) MAP, marycin, Merrel Dow MDL-27048, Medco MEDR-340, merbarone, merocyanine derivatives, methylanilinoacridine, Molecular Genetics MGI-136, minactivin, mitonafide, mitoquidone, mopidamol, motretinide, Zenyaku Kogyo MST-16, N-(retinoyl)amino acids, Nisshin Flour Milling N-021, N-acylated-dehydroalanines, nafazatrom, Taisho NCU-190, nocodazole derivative, Normosang, NCI NSC-145813, NCI NSC-361456, NCI NSC-604782, NCI NSC-95580, octreotide, Ono ONO-112, oquizanocine, Akzo Org-10172, pancratistatin, pazelliptine, Warner-Lambert PD-111707, Warner-Lambert PD-115934, Warner-Lambert PD-131141, Pierre Fabre PE-1001, ICRT peptide D, piroxantrone, polyhaematoporphyrin, polypreic acid, Efamol porphyrin, probimane, procarbazine, proglumide, Invitron protease nexin I, Tobishi RA-700, razoxane, Sapporo Breweries RBS, restrictin-P, retelliptine, retinoic acid, Rhone-Poulenc RP-49532, Rhone-Poulenc RP-56976, SmithKline SK&F-104864, Sumitomo SM-108, Kuraray SMANCS, SeaPharm SP-10094, spatol, spirocyclopropane derivatives, spirogermanium, Unimed, SS Pharmaceutical SS-554, strypoldinone, Stypoldione, Suntory SUN 0237, Suntory SUN 2071, superoxide dismutase, Toyama T-506, Toyama T-680, taxol, Teijin TEI-0303, teniposide, thaliblastine, Eastman Kodak TJB-29, tocotrienol, Topostin, Teijin TT-82, Kyowa Hakko UCN-01, Kyowa Hakko UCN-1028, ukrain, Eastman Kodak USB-006, vinblastine sulfate, vincristine, vindesine, vinestramide, vinorelbine, vintriptol, vinzolidine, withanolides and Yamanouchi YM-534.

Examples of radioprotective agents which may be used in combination with compounds of the present invention are AD-5, adchnon, amifostine analogues, detox, dimesna, 1-102, MM-159, N-acylated-dehydroalanines, TGF-Genentech, tiprotimod, amifostine, WR-151327, FUT-187, ketoprofen transdermal, nabumetone, superoxide dismutase (Chiron) and superoxide dismutase Enzon.

Besides being useful for human treatment, these compounds are also useful for veterinary treatment of companion animals, exotic animals and farm animals, including mammals, rodents, and the like. More preferred animals include horses, dogs, and cats.

The present compounds may also be used in co-therapies, partially or completely, in addition to other antiinflammatories, such as together with steroids, NSAIDs, iNOS inhibitors, p-38 inhibitors, TNF inhibitors, 5-lipoxygenase inhibitors, $LTB_4$ receptor antagonists and $LTA_4$ hydrolase inhibitors.

Suitable $LTA_4$ hydrolase inhibitors include RP-64966, (S,S)-3-amino-4-(4-benzyloxyphenyl)-2-hydroxybutyric acid benzyl ester (Scripps Res. Inst.), N-(2(R)-(cyclohexylmethyl)-3-(hydroxycarbamoyl)propionyl)-L-alanine (Searle), 7-(4-(4-ureidobenzyl)phenyl)heptanoic acid (Rhone-Poulenc Rorer), and 3-(3-(1E,3E-tetradecadienyl)-2-oxiranyl)benzoic acid lithium salt (Searle).

Suitable $LTB_4$ receptor antagonists include, among others, ebselen, linazolast, ontazolast, Bayer Bay-x-1005, Ciba Geigy compound CGS-25019C, Leo Denmark compound ETH-615, Merck compound MAFP, Terumo compound. TMK-688, Tanabe compound T-0757, Lilly compounds LY-213024, LY-210073, LY223982, LY233469, and LY255283, LY-293111, 264086 and 292728, ONO compounds ONO-LB457, ONO-4057, and ONO-LB-448, Shionogi compound S-2474, calcitrol, Lilly compounds Searle compounds SC-53228, SC-41930, SC-50605 and SC-51146, Warner Lambert compound BPC 15, SmithKline Beecham compound SB-209247 and SK&F compound SKF-104493. Preferably, the $LTB_4$ receptor antagonists are selected from calcitrol, ebselen, Bayer Bay-x-1005, Ciba Geigy compound CGS-25019C, Leo Denmark compound ETH-615, Lilly compound LY-293111, Ono compound ONO-4057, and Terumo compound TMK-688.

Suitable 5-LO inhibitors include, among others, Abbott compounds A-76745, 78773 and ABT761, Bayer Bay-x-1005, Cytomed CMI-392, Eisai E-3040, Scotia Pharmaceutica EF-40, Fujirebio F-1322, Merckle ML-3000, Purdue Frederick PF-5901, 3M Pharmaceuticals R-840, rilopirox, flobufen, linasolast, lonapolene, masoprocol, ontasolast, tenidap, zileuton, pranlukast, tepoxalin, rilopirox, flezelastine hydrochloride, enazadrem phosphate, and bunaprolast.

The present compounds may also be used in combination therapies with opioids and other analgesics, including narcotic analgesics, Mu receptor antagonists, Kappa receptor antagonists, non-narcotic (i.e. non-addictive) analgesics, monoamine uptake inhibitors, adenosine regulating agents, cannabinoid derivatives, Substance P antagonists, neurokinin-1 receptor antagonists and sodium channel blockers, among others. More preferred would be combinations with compounds selected from morphine, meperidine, codeine, pentazocine, buprenorphine, butorphanol, dezocine, meptazinol, hydrocodone, oxycodone, methadone, Tramadol [(+) enantiomer], DuP 747, Dynorphine A, Enadoline, RP-60180, HN-11608, E-2078, ICI-204448, acetominophen (paracetamol), propoxyphene, nalbuphine, E-4018, filenadol, mirfentanil, amitriptyline, DuP631, Tramadol [(−) enantiomer], GP-531, acadesine, AKI-1, AKI-2, GP-1683, GP-3269, 4030W92, tramadol racemate, Dynorphine A, E-2078, AXC3742, SNX-111, ADL2-1294, ICI-204448, CT-3, CP-99,994, and CP-99,994.

The compounds can be used in co-therapies, in place of other conventional antiinflammatories, in combination with one or more antihistamines, decongestants, diuretics, antitussive agents or with other agents previously known to be effective in combination with antiinflammatory agents.

The term "prevention" includes either preventing the onset of clinically evident cardiovascular disorders altogether or preventing the onset of a preclinically evident stage of cardiovascular disorder in individuals. This includes prophylactic treatment of those at risk of developing a disease, such as a cardiovascular disorder, dementia or cancer, for example.

The phrase "therapeutically-effective" is intended to qualify the amount of each agent which will achieve the goal of improvement in disorder severity and the frequency of incidence over treatment of each agent by itself, while avoiding adverse side effects typically associated with alternative therapies.

The present invention preferably includes compounds which selectively inhibit cyclooxygenase-2 over cyclooxygenase-1. Preferably, the compounds have a cyclooxygenase-2 $IC_{50}$ of less than about 0.5 $\mu$M, and also have a selectivity ratio of cyclooxygenase-2 inhibition over cyclooxygenase-1 inhibition of at least 50, and more preferably of at least 100. Even more preferably, the compounds have a cyclooxygenase-1 $IC_{50}$ of greater than about 5 $\mu$M. Such preferred selectivity may indicate an ability to reduce the incidence of common NSAID-induced side effects.

A preferred class of compounds consists of those compounds of Formula I wherein X is selected from O, S, $CR^cR^b$ and $NR^a$; wherein $R^a$ is selected from hydrido, $C_1$–$C_3$-alkyl, phenyl-$C_1$–$C_3$-alkyl, (substituted phenyl)-$C_1$–$C_3$-alkyl, $C_1$–$C_3$-alkoxycarbonyl-$C_1$–$C_3$-alkyl and carboxy-$C_1$–$C_6$-alkyl; wherein each of $R^b$ and $R^c$ is independently selected from hydrido, $C_1$–$C_3$-alkyl, phenyl-$C_1$–$C_3$-alkyl, (substituted phenyl)-$C_1$–$C_3$-alkyl, $C_1$–$C_3$-perfluoroalkyl, chloro, $C_1$–$C_4$-alkylthio, $C_1$–$C_4$-alkoxy, nitro, cyano and cyano-$C_1$–$C_3$-alkyl; or wherein $CR^bR^c$ forms a cyclopropyl ring; wherein R is selected from carboxyl, aminocarbonyl, $C_1$–$C_4$-alkylsulfonylaminocarbonyl and $C_1$–$C_4$-alkoxycarbonyl; wherein R" is selected from hydrido, phenyl, thienyl, $C_1$–$C_4$-alkyl and $C_2$–$C_4$-alkenyl; wherein $R^1$ is selected from $C_1$–$C_3$-perfluoroalkyl, chloro, $C_1$–$C_4$-alkylthio, $C_1$–$C_4$-alkoxy, nitro, cyano and cyano-$C_1$–$C_3$-alkyl; wherein $R^2$ is one or more radicals independently selected from hydrido, halo, $C_1$–$C_4$-alkyl, $C_2$–$C_4$-alkenyl, $C_2$–$C_6$-alkynyl, halo-$C_2$–$C_6$-alkynyl, aryl-$C_1$–$C_3$-alkyl, aryl-$C_2$–$C_4$-alkynyl, aryl-$C_2$–$C_4$-alkenyl, $C_1$–$C_4$-alkoxy, methylenedioxy, $C_1$–$C_4$-alkylthio, $C_1$–$C_4$-alkylsulfinyl, aryloxy, arylthio, arylsulfinyl, heteroaryloxy, $C_1$–$C_4$-alkoxy-$C_1$–$C_4$-alkyl, aryl-$C_1$–$C_4$-alkoxy, heteroaryl-$C_1$–$C_4$-alkoxy, aryl-$C_1$–$C_4$-alkoxy-$C_1$–$C_4$-alkyl, $C_1$–$C_4$-haloalkyl, $C_1$–$C_4$-haloalkoxy, $C_1$–$C_4$-haloalkylthio, $C_1$–$C_4$-haloalkylsulfinyl, $C_1$–$C_4$-haloalkylsulfonyl, $C_1$–$C_3$-(haloalkyl) —$C_1$–$C_3$-hydroxyalkyl, $C_1$–$C_4$-hydroxyalkyl, hydroxyimino-$C_1$–$C_4$-alkyl, $C_1$–$C_4$-alkylamino, arylamino, N-aryl-N—$C_1$–$C_4$-alkylamino, heteroarylamino, N-heteroaryl-N—$C_1$–$C_4$-alkylamino, nitro, cyano, amino, aminosulfonyl, $C_1$–$C_4$-alkylaminosulfonyl, arylaminosulfonyl, heteroarylaminosulfonyl, aryl-$C_1$–$C_4$-alkylaminosulfonyl, heteroaryl-$C_1$–$C_4$-alkylaminosulfonyl, heterocyclylsulfonyl, $C_1$–$C_4$-alkylsulfonyl, aryl-$C_1$–$C_4$-alkylsulfonyl, optionally substituted aryl, optionally substituted heteroaryl, aryl-$C_1$–$C_4$-alkylcarbonyl, heteroaryl-$C_1$–$C_4$-alkylcarbonyl, heteroarylcarbonyl, arylcarbonyl, aminocarbonyl, $C_1$–$C_4$-alkoxycarbonyl, formyl, $C_1$–$C_4$-haloalkylcarbonyl and $C_1$–$C_4$-alkylcarbonyl; and wherein the A ring atoms $A^1$, $A^2$, $A^3$ and $A_4$ are independently selected from carbon and nitrogen with the proviso that at least three of $A^1$, $A^2$, $A^3$ and $A^4$ are carbon; or wherein $R^2$ together with ring A forms a naphthyl or quinolyl radical; or an isomer or pharmaceutically acceptable salt thereof.

A more preferred class of compounds of Formula I consists of compounds wherein X is selected from O, S and $NR^a$; wherein $R^a$ is selected from hydrido, $C_1$–$C_3$-alkyl and (optionally substituted phenyl)methyl; wherein R is carboxyl; wherein R" is selected from hydrido, $C_1$–$C_3$-alkyl and $C_2$–$C_3$-alkenyl; wherein $R^1$ is selected from $C_1$–$C_3$-perfluoroalkyl; wherein $R^2$ is one or more radicals independently selected from hydrido, halo, $C_1$–$C_4$-alkyl, $C_2$–$C_3$-alkenyl, $C_2$–$C_6$-alkynyl, halo-$C_2$–$C_6$-alkynyl, optionally substituted phenyl-$C_1$–$C_3$-alkyl, optionally substituted phenyl-$C_2$–$C_3$-alkynyl, phenyl-$C_2$–$C_3$-alkenyl, $C_1$–$C_3$-alkoxy, methylenedioxy, $C_1$–$C_3$-alkoxy-$C_1$–$C_3$-alkyl, $C_1$–$C_3$-alkylthio, $C_1$–$C_3$-alkylsulfinyl, optionally substituted phenyloxy, optionally substituted phenylthio, optionally substituted phenylsulfinyl, $C_1$–$C_3$-haloalkyl-$C_1$–$C_3$-hydroxyalkyl, phenyl-$C_1$–$C_3$-alkoxy-$C_1$–$C_3$-alkyl, $C_1$–$C_3$-haloalkyl, $C_1$–$C_3$-haloalkoxy, $C_1$–$C_3$-haloalkylthio, $C_1$–$C_3$-hydroxyalkyl, $C_1$–$C_3$-alkoxy-$C_1$–$C_3$-alkyl, hydroxyimino-$C_1$–$C_3$-alkyl, $C_1$–$C_6$-alkylamino, nitro, cyano, amino, aminosulfonyl, N-alkylaminosulfonyl, N-arylaminosulfonyl, N-heteroarylaminosulfonyl, N-(phenyl-$C_1$–$C_6$-alkyl) aminosulfonyl, N-(heteroaryl-$C_1$–$C_6$-alkyl)aminosulfonyl, phenyl-$C_1$–$C_3$-alkylsulfonyl, 5- to 8-membered heterocyclylsulfonyl, $C_1$–$C_3$-alkylsulfonyl, optionally substituted phenyl, optionally substituted 5- to 9-membered heteroaryl, phenyl-$C_1$–$C_3$-alkylcarbonyl, phenylcarbonyl, 4-chlorophenylcarbonyl, 4-hydroxyphenylcarbonyl, 4-trifluoromethylphenylcarbonyl, 4-methoxyphenylcarbonyl, aminocarbonyl, formyl, and $C_1$–$C_6$-alkylcarbonyl; wherein the A ring atoms $A^1$, $A^2$, $A^3$ and $A^4$ are independently selected from carbon and nitrogen with the proviso that at least three of $A^1$, $A^2$, $A^3$ and $A^4$ are carbon; or wherein $R^2$ together with ring A forms a naphthyl, benzofurylphenyl, or quinolyl radical; or an isomer or pharmaceutically acceptable salt thereof.

An even more preferred class of compounds of Formula I consists of compounds wherein X is selected from O, S and $NR^a$; wherein $R^a$ is selected from hydrido, methyl, ethyl, (4-trifluoromethyl)benzyl, (4-chloromethyl)benzyl, (4-methoxy)benzyl, (4-cyano)benzyl, and (4-nitro)benzyl; wherein R is carboxyl; wherein R" is selected from hydrido, ethyl and ethenyl; wherein $R^1$ is trifluoromethyl or pentafluoroethyl; wherein $R^2$ is one or more radicals independently selected from hydrido, chloro, bromo, fluoro, iodo, methyl, tert-butyl, ethenyl, ethynyl, 5-chloro-1-pentynyl, 1-pentynyl, 3,3-dimethyl-1-butynyl, benzyl, phenylethyl, phenyl-ethynyl, 4-chlorophenyl-ethynyl, 4-methoxyphenyl-ethynyl, phenylethenyl, methoxy, methylthio, methylsulfinyl, phenyloxy, phenylthio, phenylsulfinyl, methylenedioxy, benzyloxymethyl, trifluoromethyl, difluoromethyl, pentafluoroethyl, trifluoromethoxy, trifluoromethylthio, hydroxymethyl, hydroxy-trifluoroethyl, methoxymethyl, hydroxyiminomethyl, N-methylamino, nitro, cyano, amino, aminosulfonyl, N-methylaminosulfonyl, N-phenylaminosulfonyl, N-furylaminosulfonyl, N-(benzyl)aminosulfonyl, N-(furylmethyl)aminosulfonyl, benzylsulfonyl, phenylethylaminosulfonyl, furylsulfonyl, methylsulfonyl, phenyl, phenyl substituted with one or more radicals selected from chloro, fluoro, bromo, methoxy, methylthio and methylsulfonyl, benzimidazolyl, thienyl, thienyl substituted with chloro, furyl, furyl substituted with chloro, benzylcarbonyl, optionally substituted phenylcarbonyl, aminocarbonyl, formyl and methylcarbonyl; wherein the A ring atoms $A^1$, $A^2$, $A^3$ and $A^4$ are independently selected from carbon and nitrogen with the proviso that at least three of $A^1$, $A^2$, $A^3$ and $A^4$ are carbon; or wherein $R^2$ together with ring A forms a naphthyl, or quinolyl radical; or an isomer or pharmaceutically acceptable salt thereof.

Within Formula I there is a subclass of compounds of high interest represented by Formula II

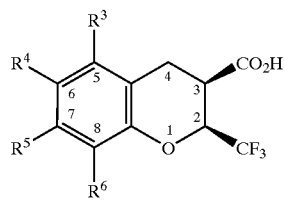

II wherein $R^3$ is selected from hydrido, $C_1$–$C_3$-alkyl, $C_1$–$C_3$-hydroxyalkyl, $C_1$–$C_3$-alkoxy and halo;

wherein $R^4$ is selected from hydrido, halo, $C_1$–$C_4$-alkyl, $C_1$–$C_3$-alkylthio, $C_1$–$C_3$-haloalkyl, amino, aminosulfonyl, $C_1$–$C_3$-alkylsulfonyl, $C_1$–$C_3$-alkylsulfinyl, $C_1$–$C_3$-alkoxy-$C_1$–$C_3$-alkyl, $C_1$–$C_3$-alkylcarbonyl, formyl, cyano, $C_1$–$C_3$-haloalkylthio, substituted or unsubstituted phenylcarbonyl, $C_1$–$C_3$-haloalkoxy, $C_1$–$C_3$-alkoxy, aryl-$C_1$–$C_3$-alkylcarbonyl, di-$C_1$–$C_3$-alkylaminosulfonyl, $C_1$–$C_3$-alkylaminosulfonyl, aryl-$C_1$–$C_3$-alkylaminosulfonyl, 5- or 6-heteroaryl-$C_2$–$C_3$-alkylaminosulfonyl, 5- or 6-membered heteroaryl, $C_1$–$C_3$-hydroxyalkyl, substituted or unsubstituted phenyl and 5- or 6-membered nitrogen-containing heterocyclylsulfonyl;

wherein $R^5$ is selected from hydrido, $C_1$–$C_4$-alkyl, halo, $C_1$–$C_3$-haloalkyl, $C_1$–$C_4$-hydroxyalkyl, $C_2$–$C_3$-alkynyl, $C_2$–$C_3$-alkenyl, $C_1$–$C_3$-alkoxy, phenoxy, phenoxy independently substituted with one or more radicals selected from $C_1$–$C_3$-haloalkyl, nitro, carboxyl, $C_1$–$C_3$-haloalkoxy, $C_1$–$C_3$-alkoxy, cyano, $C_1$–$C_3$-alkyl and halo, naphthyloxy, naphthyloxy substituted with one or more halo radicals, phenylthio, phenylthio substituted with one or more halo radicals, phenylsulfinyl, phenylsulfinyl substituted with one or more halo radicals, phenylsulfonyl, phenylsulfonyl substituted with one or more halo radicals, pyridinyloxy, pyridinyloxy substituted with one or more halo radicals, and phenyl; and wherein $R^6$ is selected from hydrido, halo, cyano, hydroxyiminomethyl, $C_1$–$C_3$-hydroxyalkyl, $C_1$–$C_3$-alkynyl, phenyl-$C_2$–$C_3$-alkynyl, $C_1$–$C_4$-alkyl, $C_1$–$C_3$-alkoxy, formyl and phenyl;

or an isomer or pharmaceutically acceptable salt thereof.

A class of compounds of particular interest consists of those compounds of Formula II wherein $R^3$ is hydrido or chloro; wherein $R^4$ is selected from hydrido, chloro, methyl, tert-butyl, methylthio, trifluoromethyl, difluoromethyl, pentafluoromethyl, trifluoromethylthio, trifluoromethoxy, cyano, substituted or unsubstituted phenylcarbonyl, and substituted or unsubstituted phenyl; wherein $R^5$ is selected from hydrido, methyl, tert-butyl, 2,2,2-trifluoroethoxy, 2-hydroxy-1,1-dimethylethyl, phenoxy, 4-methoxyphenoxy, 4-chlorophenoxy, 3-chlorophenoxy, 2-chlorophenoxy, 4-cyanophenoxy, 2,6-dimethylphenoxy, 2,4-dichlorophenoxy, 3,4-difluorophenoxy, 4-chloro-3-fluorophenoxy, 4-(trifluoromethyl)phenoxy, 4-nitrophenoxy, 4-carboxyphenoxy, 3-carboxyphenoxy, 2-chloro-4-carboxyphenoxy, 4-(trifluoromethoxy)phenoxy, 2-bromo-4-chlorophenoxy, (6-bromo-2-naphthalenyl)oxy, phenylthio, (4-methoxyphenyl)thio, (4-chlorophenyl)thio, (4-chlorophenyl)sulfinyl, (4-chlorophenyl)sulfonyl, (6-chloro-2-pyridinyl)oxy, (2-chloro-3-pyridinyl)oxy, (3-pyridinyl)oxy, (2-pyridinyl)oxy, iodo, ethenyl, ethynyl, chloro; and wherein $R^6$ is selected from hydrido, chloro, thienyl, hydroxyiminomethyl, substituted or unsubstituted phenylethynyl, phenyl and substituted phenyl; or an isomer or pharmaceutically acceptable salt thereof.

Within Formula I there is a subclass of compounds of high interest represented by Formula III:

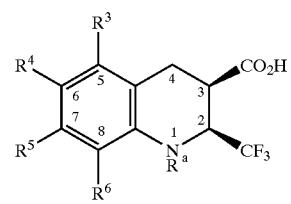

III wherein $R^a$ is selected from hydrido and lower aralkyl;
wherein $R^3$ is selected from hydrido, $C_1$–$C_3$-alkyl, $C_1$–$C_3$-hydroxyalkyl, $C_1$–$C_3$-alkoxy and halo;
wherein $R^4$ is selected from hydrido, halo, $C_1$–$C_4$-alkyl, $C_1$–$C_3$-alkylthio, $C_1$–$C_3$-haloalkyl, amino, aminosulfonyl, $C_1$–$C_3$-alkylsulfonyl, $C_1$–$C_3$-alkylsulfinyl, $C_1$–$C_3$-alkoxy-$C_1$–$C_3$-alkyl, $C_1$–$C_3$-alkylcarbonyl, formyl, cyano, $C_1$–$C_3$-haloalkylthio, substituted or unsubstituted phenylcarbonyl, $C_1$–$C_3$-haloalkoxy, $C_1$–$C_3$-alkoxy, aryl-$C_1$–$C_3$-alkylcarbonyl, di-$C_1$–$C_3$-alkylaminosulfonyl, $C_1$–$C_3$-alkylaminosulfonyl, aryl-$C_1$–$C_3$-alkylaminosulfonyl, 5- or 6-heteroaryl-$C_1$–$C_3$-alkylaminosulfonyl, 5- or 6-membered heteroaryl, $C_1$–$C_3$-hydroxyalkyl, substituted or unsubstituted phenyl and 5- or 6-membered nitrogen-containing heterocyclylsulfonyl;
wherein $R^5$ is selected from hydrido, $C_1$–$C_4$-alkyl, halo, $C_1$–$C_3$-haloalkyl, $C_1$–$C_4$-hydroxyalkyl, $C_2$–$C_3$-alkynyl, $C_2$–$C_3$-alkenyl, $C_1$–$C_3$-alkoxy, phenoxy, phenoxy independently substituted with one or more radicals selected from $C_1$–$C_3$-haloalkyl, nitro, carboxyl, $C_1$–$C_3$-haloalkoxy, $C_1$–$C_3$-alkoxy, cyano, $C_1$–$C_3$-alkyl and halo, naphthyloxy, naphthyloxy substituted with one or more halo radicals, phenylthio, phenylthio substituted with one or more halo radicals, phenylsulfinyl, phenylsulfinyl substituted with one or more halo radicals, phenylsulfonyl, phenylsulfonyl substituted with one or more halo radicals, pyridinyloxy, pyridinyloxy substituted with one or more halo radicals, and phenyl; and wherein $R^6$ is selected from hydrido, halo, cyano, hydroxyiminomethyl, $C_1$–$C_3$-hydroxyalkyl, $C_2$–$C_3$-alkynyl, phenyl-$C_2$–$C_3$-alkynyl, $C_1$–$C_4$-alkyl, $C_1$–$C_3$-alkoxy, formyl and phenyl; or an isomer or pharmaceutically acceptable salt thereof.

A class of compounds of particular interest consists of those compounds of Formula III $R^3$ is hydrido or chloro; wherein $R^4$ is selected from hydrido, chloro, methyl, tert-butyl, methylthio, trifluoromethyl, difluoromethyl, pentafluoromethyl, trifluoromethylthio, trifluoromethoxy, cyano, substituted or unsubstituted phenylcarbonyl, and substituted or unsubstituted phenyl; wherein $R^5$ is selected from hydrido, methyl, tert-butyl, 2,2,2-trifluoroethoxy, 2-hydroxy-1,1-dimethylethyl, phenoxy, 4-methoxyphenoxy, 4-chlorophenoxy, 3-chlorophenoxy, 2-chlorophenoxy, 4-cyanophenoxy, 2,6-dimethylphenoxy, 2,4-dichlorophenoxy, 3,4-difluorophenoxy, 4-chloro-3-fluorophenoxy, 4-(trifluoromethyl)phenoxy, 4-nitrophenoxy, 4-carboxyphenoxy, 3-carboxyphenoxy, 2-chloro-4-carboxyphenoxy, 4-(trifluoromethoxy)phenoxy, 2-bromo-4-chlorophenoxy, (6-bromo-2-naphthalenyl)oxy, phenylthio, (4-methoxyphenyl)thio, (4-chlorophenyl)thio, (4-chlorophenyl)sulfinyl, (4-chlorophenyl)sulfonyl, (6-chloro-2-pyridinyl)oxy, (2-chloro-3-pyridinyl)oxy, (3-pyridinyl)oxy, (2-pyridinyl)oxy, iodo, ethenyl, ethynyl, chloro; and wherein $R^6$ is selected from hydrido, chloro, thienyl, hydroxyiminomethyl, substituted or unsubstituted phenylethynyl, phenyl and substituted phenyl; or an isomer or pharmaceutically acceptable salt thereof.

Within Formula I there is a subclass of compounds of high interest represented by Formula IV

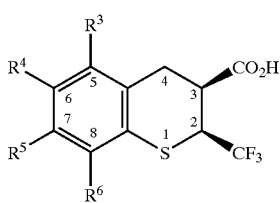

IV wherein $R^3$ is selected from hydrido, $C_1$–$C_3$-alkyl, $C_1$–$C_3$-hydroxyalkyl, $C_1$–$C_3$-alkoxy and halo;

wherein $R^4$ is selected from hydrido, halo, $C_1$–$C_4$-alkyl, $C_1$–$C_3$-alkylthio, $C_1$–$C_3$-haloalkyl, amino, aminosulfonyl, $C_1$–$C_3$-alkylsulfonyl, $C_1$–$C_3$-alkylsulfinyl, $C_1$–$C_3$-alkoxy-$C_1$–$C_3$-alkyl, $C_1$–$C_3$-alkylcarbonyl, formyl, cyano, $C_1$–$C_3$-haloalkylthio, substituted or unsubstituted phenylcarbonyl, $C_1$–$C_3$-haloalkoxy, $C_1$–$C_3$-alkoxy, aryl-$C_1$–$C_3$-alkylcarbonyl, di-$C_1$–$C_3$-alkylaminosulfonyl, $C_1$–$C_3$-alkylaminosulfonyl, aryl-$C_1$–$C_3$-alkylaminosulfonyl, 5- or 6-heteroaryl-$C_1$–$C_3$-alkylaminosulfonyl, 5- or 6-membered heteroaryl, $C_1$–$C_3$-hydroxyalkyl, substituted or unsubstituted phenyl and 5- or 6-membered nitrogen-containing heterocyclylsulfonyl;

wherein $R^5$ is selected from hydrido, $C_1$–$C_4$-alkyl, halo, $C_1$–$C_3$-haloalkyl, $C_1$–$C_4$-hydroxyalkyl, $C_2$–$C_3$-alkynyl, $C_2$–$C_3$-alkenyl, $C_1$–$C_3$-alkoxy, phenoxy, phenoxy independently substituted with one or more radicals selected from $C_1$–$C_3$-haloalkyl, nitro, carboxyl, $C_1$–$C_3$-haloalkoxy, $C_1$–$C_3$-alkoxy, cyano, $C_1$–$C_3$-alkyl and halo, naphthyloxy, naphthyloxy substituted with one or more halo radicals, phenylthio, phenylthio substituted with one or more halo radicals, phenylsulfinyl, phenylsulfinyl substituted with one or more halo radicals, phenylsulfonyl, phenylsulfonyl substituted with one or more halo radicals, pyridinyloxy, pyridinyloxy substituted with one or more halo radicals, and phenyl; and wherein $R^6$ is selected from hydrido, halo, cyano, hydroxyiminomethyl, $C_1$–$C_3$-hydroxyalkyl, $C_2$–$C_3$-alkynyl, phenyl-$C_2$–$C_3$-alkynyl, $C_1$–$C_4$-alkyl, $C_1$–$C_3$-alkoxy, formyl and phenyl; or an isomer or pharmaceutically acceptable salt thereof.

A class of compounds of particular interest consists of those compounds of Formula IV $R^3$ is hydrido or chloro; wherein $R^4$ is selected from hydrido, chloro, methyl, tert-butyl, methylthio, trifluoromethyl, difluoromethyl, pentafluoromethyl, trifluoromethylthio, trifluoromethoxy, cyano, substituted or unsubstituted phenylcarbonyl, and substituted or unsubstituted phenyl; wherein $R^5$ is selected from hydrido, methyl, tert-butyl, 2,2,2-trifluoroethoxy, 2-hydroxy-1,1-dimethylethyl, phenoxy, 4-methoxyphenoxy, 4-chlorophenoxy, 3-chlorophenoxy, 2-chlorophenoxy, 4-cyanophenoxy, 2,6-dimethylphenoxy, 2,4-dichlorophenoxy, 3,4-difluorophenoxy, 4-chloro-3-fluorophenoxy, 4-(trifluoromethyl)phenoxy, 4-nitrophenoxy, 4-carboxyphenoxy, 3-carboxyphenoxy, 2-chloro-4-carboxyphenoxy, 4-(trifluoromethoxy)phenoxy, 2-bromo-4-chlorophenoxy, (6-bromo-2-naphthalenyl)oxy, phenylthio, (4-methoxyphenyl)thio, (4-chlorophenyl)thio, (4-chlorophenyl)sulfinyl, (4-chlorophenyl)sulfonyl, (6-chloro-2-pyridinyl)oxy, (2-chloro-3-pyridinyl)oxy, (3-pyridinyl)oxy, (2-pyridinyl)oxy, iodo, ethenyl, ethynyl, chloro; and wherein $R^6$ is selected from hydrido, chloro, thienyl, hydroxyiminomethyl, substituted or unsubstituted phenylethynyl, phenyl and substituted phenyl; or an isomer or pharmaceutically acceptable salt thereof.

A family of specific compounds of particular interest within Formula I consists of compounds and pharmaceutically-acceptable salts thereof as follows:

6-chloro-3,4-dihydro-7-[(2-pyridyl-N-oxide)thio]-2-(trifluoromethyl)-2H-1-benzopyran-3-carboxylic acid;

6-chloro-3,4-dihydro-7-[(3-chloro-2-pyridyl-{N-oxide})thio]-2-(trifluoromethyl)-2H-1-benzopyran-3-carboxylic acid;

6-chloro-1,2,3,4-tetrahydro-7-[(2-pyridyl-N-oxide)oxy]-2-(trifluoromethyl)-2H-quinoline-3-carboxylic acid;

6-chloro-7-[(3-chloro-2-pyridyl-{N-oxide}) oxy]-1,2,3,4-tetrahydro-2-(trifluoromethyl)-2H-quinoline-3-carboxylic acid;

6-chloro-1,2,3,4-tetrahydro-7-[(2-pyridyl-N-oxide) thio]-2-(trifluoromethyl)-2H-quinoline-3-carboxylic acid;

6-chloro-7-[(3-chloro-2-pyridyl-{N-oxide}) thio]-1,2,3,4-tetrahydro-2-(trifluoromethyl)-2H-quinoline-3-carboxylic acid;

6-chloro-3,4-dihydro-7-[(2-pyridyl-N-oxide)oxy]-2-(trifluoromethyl)-2H-1-benzothiopyran-3-carboxylic acid;

6-chloro-7-[(3-chloro-2-pyridyl-{N-oxide}) oxy]-3,4-dihydro-2-(trifluoromethyl)-2H-1-benzothiopyran-3-carboxylic acid;

6-chloro-3,4-dihydro-7-[(2-pyridyl-N-oxide)thio]-2-(trifluoromethyl)-2H-1-benzothiopyran-3-carboxylic acid;

6-chloro-7-[(3-chloro-2-pyridyl-{N-oxide})thio]-3,4-dihydro-2-(trifluoromethyl)-2H-1-benzothiopyran-3-carboxylic acid;

6-chloro-7-(3,4-dichlorophenoxy)-3,4-dihydro-2-(trifluoromethyl)-2H-1-benzopyran-3-carboxylic acid;

6-chloro-7-(3-bromo-4-chlorophenoxy)-3,4-dihydro-2-(trifluoromethyl)-2H-1-benzopyran-3-carboxylic acid;

6-chloro-7-(4-bromo-3-chlorophenoxy)-3,4-dihydro-2-(trifluoromethyl)-2H-1-benzopyran-3-carboxylic acid;

6-chloro-7-(3,4-dibromophenoxy)-3,4-dihydro-2-(trifluoromethyl)-2H-1-benzopyran-3-carboxylic acid;

6-chloro-7-[4-chloro-3-(trifluoromethyl)phenoxy]-3,4-dihydro-2-(trifluoromethyl)-2H-1-benzopyran-3-carboxylic acid;

6-chloro-7-[3-chloro-4-(trifluoromethyl)phenoxy]-3,4-dihydro-2-(trifluoromethyl)-2H-1-benzopyran-3-carboxylic acid;

6-chloro-7-(2,6-dichlorophenoxy)-3,4-dihydro-2-(trifluoromethyl)-2H-1-benzopyran-3-carboxylic acid;

6-chloro-7-(2,6-dibromophenoxy)-3,4-dihydro-2-(trifluoromethyl)-2H-1-benzopyran-3-carboxylic acid;

6-chloro-7-(2,6-difluorophenoxy)-3,4-dihydro-2-(trifluoromethyl)-2H-1-benzopyran-3-carboxylic acid;

6-chloro-7-(2,5-dichlorophenoxy)-3,4-dihydro-2-(trifluoromethyl)-2H-1-benzopyran-3-carboxylic acid;

6-chloro-7-(2,5-dibromophenoxy)-3,4-dihydro-2-(trifluoromethyl)-2H-1-benzopyran-3-carboxylic acid;

6-chloro-7-(2,5-difluorophenoxy)-3,4-dihydro-2-(trifluoromethyl)-2H-1-benzopyran-3-carboxylic acid;

6-chloro-7-(2,3-dichlorophenoxy)-3,4-dihydro-2-(trifluoromethyl)-2H-1-benzopyran-3-carboxylic acid;

6-chloro-7-(2,3-dibromophenoxy)-3,4-dihydro-2-(trifluoromethyl)-2H-1-benzopyran-3-carboxylic acid;

6-chloro-7-(2,3-difluorophenoxy)-3,4-dihydro-2-(trifluoromethyl)-2H-1-benzopyran-3-carboxylic acid;

6-chloro-7-(4-chloro-3-cyanophenoxy)-3,4-dihydro-2-(trifluoromethyl)-2H-1-benzopyran-3-carboxylic acid;

6-chloro-3,4-dihydro-7-(3-tert-butylphenoxy)-2-(trifluoromethyl)-2H-1-benzopyran-3-carboxylic acid;

6-chloro-3,4-dihydro-7-(2-tert-butylphenoxy)-2-(trifluoromethyl)-2H-1-benzopyran-3-carboxylic acid;

6-chloro-7-(4-chloro-3-tert-butylphenoxy)-3,4-dihydro-2-(trifluoromethyl)-2H-1-benzopyran-3-carboxylic acid;

6-chloro-7-(4-chloro-2-tert-butylphenoxy)-3,4-dihydro-2-(trifluoromethyl)-2H-1-benzopyran-3-carboxylic acid;

6-chloro-7-(2-chloro-3-tert-butyl phenoxy)-3,4-dihydro-2-(trifluoromethyl)-2H-1-benzopyran-3-carboxylic acid;

3,4-dihydro-7-phenoxy-2-(trifluoromethyl)-2H-1-benzopyran-3-carboxylic acid;

6-chloro-3,4-dihydro-7-phenoxy-2-(trifluoromethyl)-2H-1-benzopyran-3-carboxylic acid;

6-chloro-3,4-dihydro-7-(2-hydroxy-1,1-dimethylethyl)-2-(trifluoromethyl)-2H-1-benzopyran-3-carboxylic acid;

3,4-dihydro-7-(2-hydroxy-1,1-dimethylethyl)-2-(trifluoromethyl)-2H-1-benzopyran-3-carboxylic;

6-chloro-3,4-dihydro-7-iodo-2-(trifluoromethyl)-2H-1-benzopyran-3-carboxylic acid;

6-chloro-3,4-dihydro-7-ethynyl-2-(trifluoromethyl)-2H-1-benzopyran-3-carboxylic acid;

6-chloro-3,4-dihydro-7-ethenyl-2-(trifluoromethyl)-2H-1-benzopyran-3-carboxylic acid;

6-chloro-3,4-dihydro-7-(4-methoxyphenoxy)-2-(trifluoromethyl)-2H-1-benzopyran-3-carboxylic acid;

6-chloro-7-(4-chlorophenoxy)-3,4-dihydro-2-(trifluoromethyl)-2H-1-benzopyran-3-carboxylic acid;

6-chloro-7-(4-chlorophenoxy)-3,4-dihydro-2-(trifluoromethyl)-2H-1-benzopyran-3-carboxylic acid;

6-chloro-7-(4-cyanophenoxy)-3,4-dihydro-2-(trifluoromethyl)-2H-1-benzopyran-3-carboxylic acid;

6-chloro-3,4-dihydro-7-[4-(trifluoromethyl)phenoxy]-2-(trifluoromethyl)-2H-1-benzopyran-3-carboxylic acid;

6-chloro-3,4-dihydro-7-[4-(trifluoromethoxy)phenoxy]-2-(trifluoromethyl)-2H-1-benzopyran-3-carboxylic acid;

6-chloro-7-(2-bromo-4-chlorophenoxy)-3,4-dihydro-2-(trifluoromethyl)-2H-1-benzopyran-3-carboxylic acid;

6-chloro-7-[(6-bromo-2-naphthyl)oxy]-3,4-dihydro-2-(trifluoromethyl)-2H-1-benzopyran-3-carboxylic acid;

6-chloro-3,4-dihydro-7-(2,6-dimethylphenoxy)-2-(trifluoromethyl)-2H-1-benzopyran-3-carboxylic acid;

6-chloro-3,4-dihydro-7-[(4-methoxyphenyl)thio]-2-(trifluoromethyl)-2H-1-benzopyran-3-carboxylic acid;

6-chloro-7-[(4-chlorophenyl)thio]-3,4-dihydro-2-(trifluoromethyl)-2H-1-benzopyran-3-carboxylic acid;

6-chloro-7-[(4-chlorophenyl)sulfinyl]-3,4-dihydro-2-(trifluoromethyl)-2H-1-benzopyran-3-carboxylic acid;

6-chloro-7-[(4-chlorophenyl)sulfonyl]-3,4-dihydro-2-(trifluoromethyl)-2H-1-benzopyran-3-carboxylic acid;

6-chloro-3,4-dihydro-7-phenylthio-2-(trifluoromethyl)-2H-1-benzopyran-3-carboxylic acid;

6-chloro-7-(3-chlorophenoxy)-3,4-dihydro-2-(trifluoromethyl)-2H-1-benzopyran-3-carboxylic acid;

6-chloro-7-(2,4-dichlorophenoxy)-3,4-dihydro-2-(trifluoromethyl)-2H-1-benzopyran-3-carboxylic acid;

6-chloro-7-(3,4-difluorophenoxy)-3,4-dihydro-2-(trifluoromethyl)-2H-1-benzopyran-3-carboxylic acid;

6-chloro-7-[(6-chloro-2-pyridinyl)oxy]-3,4-dihydro-2-(trifluoromethyl)-2H-1-benzopyran-3-carboxylic acid;

6-chloro-7-[(2-chloro-3-pyridinyl)oxy]-3,4-dihydro-2-(trifluoromethyl)-2H-1-benzopyran-3-carboxylic acid;

6-chloro-3,4-dihydro-7-[(3-pyridinyl)oxy]-2-(trifluoromethyl)-2H-1-benzopyran-3-carboxylic acid;

6-chloro-3,4-dihydro-7-[(2-pyridinyl)oxy]-2-(trifluoromethyl)-2H-1-benzopyran-3-carboxylic acid;

6-chloro-3,4-dihydro-7-(4-nitrophenoxy)-2-(trifluoromethyl)-2H-1-benzopyran-3-carboxylic acid;

6-chloro-7-(2-chlorophenoxy)-3,4-dihydro-2-(trifluoromethyl)-2H-1-benzopyran-3-carboxylic acid;

6-chloro-7-(4-chloro-3-fluorophenoxy)-3,4-dihydro-2-(trifluoromethyl)-2H-1-benzopyran-3-carboxylic acid;

6-chloro-7-(4-carboxyphenoxy)-3,4-dihydro-2-(trifluoromethyl)-2H-1-benzopyran-3-carboxylic acid;

6-chloro-7-(2-chloro-4-carboxyphenoxy)-3,4-dihydro-2-(trifluoromethyl)-2H-1-benzopyran-3-carboxylic acid;

6-chloro-7-(3-carboxyphenoxy)-3,4-dihydro-2-(trifluoromethyl)-2H-1-benzopyran-3-carboxylic acid;

6-chloro-3,4-dihydro-7-(2,2,2-trifluoroethoxy)-2-(trifluoromethyl)-2H-1-benzopyran-3-carboxylic acid;

6-chloro-1,2,3,4-tetrahydro-8-methyl-2-(trifluoromethyl)-3-quinolinecarboxylic acid;

1,2,3,4-tetrahydro-5-methyl-2-(trifluoromethyl)-3-quinolinecarboxylic acid;

1,2,3,4-tetrahydro-6-(4-fluorophenyl)-2-(trifluoromethyl)-3-quinolinecarboxylic acid;

1,2,3,4-tetrahydro-6-ethynyl-2-(trifluoromethyl)-3-quinolinecarboxylic acid;

8-bromo-1,2,3,4-tetrahydro-6-methyl-2-(trifluoromethyl)-3-quinolinecarboxylic acid;

1,2,3,4-tetrahydro-6-phenylethynyl-2-(trifluoromethyl)-3-quinolinecarboxylic acid;

6-chloro-3,4-dihydro-7-[(3-pyridyl-N-oxide)oxy]-2-(trifluoromethyl)-2H-1-benzopyran-3-carboxylic acid;

6-chloro-3,4-dihydro-7-[(2-pyridyl-N-oxide)oxy]-2-(trifluoromethyl)-2H-1-benzopyran-3-carboxylic acid;

6-chloro-7-[(3-chloro-2-pyridyl-{N-oxide})oxy]-3,4-dihydro-2-(trifluoromethyl)-2H-1-benzopyran-3-carboxylic acid;

6-chloro-7-[(4-chloro-2-pyridyl-{N-oxide}) oxy]-3,4-dihydro-2-(trifluoromethyl)-2H-1-benzopyran-3-carboxylic acid;
6-chloro-7-[(5-chloro-2-pyridyl-{N-oxide})oxy]-3,4-dihydro-2-(trifluoromethyl)-2H-1-benzopyran-3-carboxylic acid;
6-chloro-7-[(6-chloro-2-pyridyl-{N-oxide})oxy]-3,4-dihydro-2-(trifluoromethyl)-2H-1-benzopyran-3-carboxylic acid;
6-chloro-3,4-dihydro-2-trifluoromethyl-2H-1-benzopyran-3-carboxylic acid;
3,4-dihydro-7-ethyl-2-trifluoromethyl-2H-1-benzopyran-3-carboxylic acid;
7-methyl-3,4-dihydro-2-trifluoromethyl-2H-1-benzopyran-3-carboxylic acid;
2,7-bis(trifluoromethyl)-3,4-dihydro-2H-1-benzopyran-3-carboxylic acid;
7-bromo-3,4-dihydro-2-trifluoromethyl-2H-1-benzopyran-3-carboxylic acid;
6-chloro-3,4-dihydro-7-methyl-2-trifluoromethyl-2H-1-benzopyran-3-carboxylic acid;
3,4-dihydro-8-(1-methylethyl)-2-trifluoromethyl-2H-1-benzopyran-3-carboxylic acid;
6-chloro-3,4-dihydro-7-(1,1-dimethylethyl)-2-trifluoromethyl-2H-1-benzopyran-3-carboxylic acid;
6-chloro-3,4-dihydro-8-(1-methylethyl)-2-trifluoromethyl-2H-1-benzopyran-3-carboxylic acid;
3,4-dihydro-2-trifluoromethyl-2H-1-benzopyran-3-carboxylic acid;
3,4-dihydro-8-ethoxy-2-trifluoromethyl-2H-1-benzopyran-3-carboxylic acid;
3,4-dihydro-7-(1,1-dimethylethyl)-2-trifluoromethyl-2H-1-benzopyran-3-carboxylic acid;
6-bromo-3,4-dihydro-2-trifluoromethyl-2H-1-benzopyran-3-carboxylic acid;
8-chloro-3,4-dihydro-2-trifluoromethyl-2H-1-benzopyran-3-carboxylic acid;
8-bromo-6-chloro-3,4-dihydro-2-trifluoromethyl-2H-1-benzopyran-3-carboxylic acid;
3,4-dihydro-6-trifluoromethoxy-2-trifluoromethyl-2H-1-benzopyran-3-carboxylic acid;
3,4-dihydro-8-fluoro-2-trifluoromethyl-2H-1-benzopyran-3-carboxylic acid;
5,7-dichloro-3,4-dihydro-2-trifluoromethyl-2H-1-benzopyran-3-carboxylic acid;
7,8-dichloro-3,4-dihydro-2-trifluoromethyl-2H-1-benzopyran-3-carboxylic acid;
3,4-dihydro-7-isopropyloxy-2-trifluoromethyl-2H-1-benzopyran-3-carboxylic acid;
3,4-dihydro-8-phenyl-2-trifluoromethyl-2H-1-benzopyran-3-carboxylic acid;
3,4-dihydro-7,8-dimethyl-2-trifluoromethyl-2H-1-benzopyran-3-carboxylic acid;
6,8-bis(1,1-dimethylethyl)-3,4-dihydro-2-trifluoromethyl-2H-1-benzopyran-3-carboxylic acid;
7-chloro-3,4-dihydro-2-trifluoromethyl-2H-1-benzopyran-3-carboxylic acid;
3,4-dihydro-7-(1-methylethyl)-2-trifluoromethyl-2H-1-benzopyran-3-carboxylic acid;
3,4-dihydro-7-phenyl-2-trifluoromethyl-2H-1-benzopyran-3-carboxylic acid;
6-chloro-3,4-dihydro-7-ethyl-2-trifluoromethyl-2H-1-benzopyran-3-carboxylic acid;
3,4-dihydro-8-ethyl-2-trifluoromethyl-2H-1-benzopyran-3-carboxylic acid;
6-chloro-3,4-dihydro-8-ethyl-2-trifluoromethyl-2H-1-benzopyran-3-carboxylic acid;
6-chloro-3,4-dihydro-7-phenyl-2-trifluoromethyl-2H-1-benzopyran-3-carboxylic acid;
6,7-dichloro-3,4-dihydro-2-trifluoromethyl-2H-1-benzopyran-3-carboxylic acid;
6,8-dichloro-3,4-dihydro-2-trifluoromethyl-2H-1-benzopyran-3-carboxylic acid;
6,8-dibromo-3,4-dihydro-2-trifluoromethyl-2H-1-benzopyran-3-carboxylic acid;
3,4-dihydro-6,8-dimethoxy-2-trifluoromethyl-2H-1-benzopyran-3-carboxylic acid;
3,4-dihydro-6-nitro-2-trifluoromethyl-2H-1-benzopyran-3-carboxylic acid;
6-amino-3,4-dihydro-2-trifluoromethyl-2H-1-benzopyran-3-carboxylic acid; ethyl 6-amino-3,4-dihydro-2-trifluoromethyl-2H-1-benzopyran-3-carboxylate;
6-chloro-3,4-dihydro-8-methyl-2-trifluoromethyl-2H-1-benzopyran-3-carboxylic acid;
8-chloro-3,4-dihydro-6-methyl-2-trifluoromethyl-2H-1-benzopyran-3-carboxylic acid;
8-chloro-3,4-dihydro-6-methoxy-2-trifluoromethyl-2H-1-benzopyran-3-carboxylic acid;
6,8-difluoro-3,4-dihydro-2-trifluoromethyl-2H-1-benzopyran-3-carboxylic acid;
6-bromo-8-chloro-3,4-dihydro-2-trifluoromethyl-2H-1-benzopyran-3-carboxylic acid;
8-bromo-3,4-dihydro-6-fluoro-2-trifluoromethyl-2H-1-benzopyran-3-carboxylic acid;
8-bromo-3,4-dihydro-6-methyl-2-trifluoromethyl-2H-1-benzopyran-3-carboxylic acid;
8-bromo-3,4-dihydro-5-fluoro-2-trifluoromethyl-2H-1-benzopyran-3-carboxylic acid;
6-chloro-3,4-dihydro-8-fluoro-2-trifluoromethyl-2H-1-benzopyran-3-carboxylic acid;
6-bromo-3,4-dihydro-8-methoxy-2-trifluoromethyl-2H-1-benzopyran-3-carboxylic acid;
7-(N,N-diethylamino)-3,4-dihydro-2-trifluoromethyl-2H-1-benzopyran-3-carboxylic acid;
3,4-dihydro-6-[[(phenylmethyl)amino]sulfonyl]-2-trifluoromethyl-2H-1-benzopyran-3-carboxylic acid;
3,4-dihydro-6-[(dimethylamino)sulfonyl]-2-trifluoromethyl-2H-1-benzopyran-3-carboxylic acid;
6-aminosulfonyl-3,4-dihydro-2-trifluoromethyl-2H-1-benzopyran-3-carboxylic acid;
3,4-dihydro-6-(methylamino)sulfonyl-2-trifluoromethyl-2H-1-benzopyran-3-carboxylic acid;
3,4-dihydro-6-[(4-morpholino)sulfonyl]-2-trifluoromethyl-2H-1-benzopyran-3-carboxylic acid;
3,4-dihydro-6-[(1,1-dimethylethyl)aminosulfonyl]-2-trifluoromethyl-2H-1-benzopyran-3-carboxylic acid;
3,4-dihydro-6-[(2-methylpropyl)aminosulfonyl]-2-trifluoromethyl-2H-1-benzopyran-3-carboxylic acid;
3,4-dihydro-6-methylsulfonyl-2-trifluoromethyl-2H-1-benzopyran-3-carboxylic acid;
8-chloro-3,4-dihydro-6-[[(phenylmethyl)amino]sulfonyl]-2-trifluoromethyl-2H-1-benzopyran-3-carboxylic acid;
6-N,N-diethylaminosulfonyl-3,4-dihydro-2-trifluoromethyl-2H-1-benzopyran-3-carboxylic acid;
3,4-dihydro-6-phenylacetyl-2-trifluoromethyl-2H-1-benzopyran-3-carboxylic acid;
3,4-dihydro-6-(2,2-dimethylpropylcarbonyl)-2-trifluoromethyl-2H-1-benzopyran-3-carboxylic acid;
6,8-dichloro-3,4-dihydro-7-methoxy-2-trifluoromethyl-2H-1-benzopyran-3-carboxylic acid;
6-chloro-3,4-dihydro-2-trifluoromethyl-2H-1-benzothiopyran-3-carboxylic acid;
3,4-dihydro-6-[[(2-furanylmethyl)amino]sulfonyl]-2-(trifluoromethyl)-2H-1-benzopyran-3-carboxylic acid;

3,4-dihydro-6-[(phenylmethyl)sulfonyl]-2-(trifluoromethyl)-2H-1-benzopyran-3-carboxylic acid;
3,4-dihydro-6-[[(phenylethyl)amino]sulfonyl]-2-(trifluoromethyl)-2H-1-benzopyran-3-carboxylic acid;
3,4-dihydro-6-iodo-2-trifluoromethyl-2H-1-benzopyran-3-carboxylic acid;
6-chloro-3,4-dihydro-8-iodo-2-(trifluoromethyl)-2H-1-benzopyran-3-carboxylic acid;
8-bromo-6-chloro-3,4-dihydro-2-trifluoromethyl-2H-1-benzopyran-3-carboxylic acid;
3,4-dihydro-6-formyl-2-(trifluoromethyl)-2H-1-benzopyran-3-carboxylic acid;
6-chloro-3,4-dihydro-8-formyl-2-(trifluoromethyl)-2H-1-benzopyran-3-carboxylic acid;
6-bromo-7-(1,1-dimethylethyl)-3,4-dihydro-2-(trifluoromethyl)-2H-1-benzopyran-3-carboxylic acid;
5,6-dichloro-3,4-dihydro-2-(trifluoromethyl)-2H-1-benzopyran-3-carboxylic acid;
6-cyano-3,4-dihydro-2-(trifluoromethyl)-2H-1-benzopyran-3-carboxylic acid;
3,4-dihydro-6-hydroxymethyl-2-(trifluoromethyl)-2H-1-benzopyran-3-carboxylic acid;
6-(difluoromethyl)-3,4-dihydro-2-(trifluoromethyl)-2H-1-benzopyran-3-carboxylic acid;
2,6-bis(trifluoromethyl)-3,4-dihydro-2H-1-benzopyran-3-carboxylic acid;
3,4-dihydro-5,6,7-trichloro-2-(trifluoromethyl)-2H-1-benzopyran-3-carboxylic acid;
3,4-dihydro-6,7,8-trichloro-2-(trifluoromethyl)-2H-1-benzopyran-3-carboxylic acid;
3,4-dihydro-6-(methylthio)-2-(trifluoromethyl)-2H-1-benzopyran-3-carboxylic acid;
3,4-dihydro-6-(methylsulfinyl)-2-(trifluoromethyl)-2H-1-benzopyran-3-carboxylic acid;
5,8-dichloro-3,4-dihydro-2-(trifluoromethyl)-2H-1-benzopyran-3-carboxylic acid;
3,4-dihydro-6-(pentafluoroethyl)-2-(trifluoromethyl)-2H-1-benzopyran-3-carboxylic acid;
3,4-dihydro-6-(1,1-dimethylethyl)-2-(trifluoromethyl)-2H-1-benzopyran-3-carboxylic acid;
3,4-dihydro-2-(trifluoromethyl)-6-[(trifluoromethyl)thio]-2H-1-benzopyran-3-carboxylic acid;
6,8-dichloro-3,4-dihydro-7-methyl-2-(trifluoromethyl)-2H-1-benzopyran-3-carboxylic acid;
6-chloro-2,7-bis(trifluoromethyl)-3,4-dihydro-2H-1-benzopyran-3-carboxylic acid;
3,4-dihydro-5-methoxy-2-(trifluoromethyl)-2H-1-benzopyran-3-carboxylic acid;
6-benzoyl-3,4-dihydro-2-(trifluoromethyl)-2H-1-benzopyran-3-carboxylic acid;
6-(4-chlorobenzoyl)-3,4-dihydro-2-(trifluoromethyl)-2H-1-benzopyran-3-carboxylic acid;
3,4-dihydro-6-(4-hydroxybenzoyl)-2-(trifluoromethyl)-2H-1-benzopyran-3-carboxylic acid;
3,4-dihydro-6-phenoxy-2-(trifluoromethyl)-2μl-1-benzopyran-3-carboxylic acid;
8-chloro-6-(4-chlorophenoxy)-3,4-dihydro-2-trifluoromethyl)-2H-1-benzopyran-3-carboxylic acid;
3,4-dihydro-2-(trifluoromethyl)-6-[4-(trifluoromethyl)phenoxy]-2H-1-benzopyran-3-carboxylic acid;
3,4-dihydro-6-(4-methoxyphenoxy)-2-(trifluoromethyl)-2H-1-benzopyran-3-carboxylic acid;
6-(3-chloro-4-methoxyphenoxy)-3,4-dihydro-2-(trifluoromethyl)-2H-1-benzopyran-3-carboxylic acid;
6-(4-chlorophenoxy)-3,4-dihydro-2-(trifluoromethyl)-2H-1-benzopyran-3-carboxylic acid;
8-chloro-3,4-dihydro-2-(trifluoromethyl)-6-(4-(trifluoromethyl)phenoxy]-2H-1-benzopyran-3-carboxylic acid;
6-chloro-8-cyano-3,4-dihydro-2-(trifluoromethyl)-2H-1-benzopyran-3-carboxylic acid;
6-chloro-3,4-dihydro-8-[(hydroxyimino)methyl]-2-(trifluoromethyl)-2H-1-benzopyran-3-carboxylic acid;
6-chloro-8-(hydroxymethyl)-2-(trifluoromethyl)-2H-1-benzopyran-3-carboxylic acid;
8-(1H-benzimidazol-2-yl)-6-chloro-3,4-dihydro-2-(trifluoromethyl)-2H-1-benzopyran-3-carboxylic acid;
3,4-dihydro-7-(1,1-dimethylethyl)-2-(pentafluoroethyl)-2H-1-benzopyran-3-carboxylic acid;
6-chloro-3,4-dihydro-8-(methoxymethyl)-2-(trifluoromethyl)-2H-1-benzopyran-3-carboxylic acid;
6-chloro-8-(benzyloxymethyl)-3,4-dihydro-2-(trifluoromethyl)-2H-1-benzopyran-3-carboxylic acid;
6-chloro-3,4-dihydro-8-ethenyl-2-(trifluoromethyl)-2H-1-benzopyran-3-carboxylic acid;
6-chloro-3,4-dihydro-8-ethynyl-2-(trifluoromethyl)-2H-1-benzopyran-3-carboxylic acid;
6-chloro-3,4-dihydro-8-(2-thienyl)-2-(trifluoromethyl)-2H-1-benzopyran-3-carboxylic acid;
6-chloro-3,4-dihydro-8-(2-furanyl)-2-(trifluoromethyl)-2H-1-benzopyran-3-carboxylic acid;
6-chloro-8-(5-chloro-1-pentynyl)-3,4-dihydro-2-(trifluoromethyl)-2H-1-benzopyran-3-carboxylic acid;
6-chloro-3,4-dihydro-8-(1-pentynyl)-2-(trifluoroinethyl)-2H-1-benzopyran-3-carboxylic acid;
6-chloro-3,4-dihydro-8-(phenylethynyl)-2-(trifluoromethyl)-2H-1-benzopyran-3-carboxylic acid;
6-chloro-3,4-dihydro-8-(3,3-dimethyl-1-butynyl)-2-(trifluoromethyl)-2H-1-benzopyran-3-carboxylic acid;
6-chloro-8-[(4-chlorophenyl)ethynyl]-3,4-dihydro-2-(trifluoromethyl)-2H-1-benzopyran-3-carboxylic acid;
6-chloro-3,4-dihydro-8-[(4-methoxyphenyl)ethynyl]-2-(trifluoromethyl)-2H-1-benzopyran-3-carboxylic acid;
3,4-dihydro-6-(phenylethynyl)-2-(trifluoromethyl)-2H-1-benzopyran-3-carboxylic acid;
6-chloro-8-(4-chlorophenyl)-3,4-dihydro-2-(trifluoromethyl)-2H-1-benzopyran-3-carboxylic acid;
6-chloro-3,4-dihydro-8-(3-methoxyphenyl)-2-(trifluoromethyl)-2H-1-benzopyran-3-carboxylic acid;
6-chloro-3,4-dihydro-8-[(4-methylthio)phenyl]-2-(trifluoromethyl)-2H-1-benzopyran-3-carboxylic acid;
6-chloro-3,4-dihydro-8-[(4-methylsulfonyl)phenyl]-2-(trifluoromethyl)-2H-1-benzopyran-3-carboxylic acid;
6-chloro-3,4-dihydro-8-phenyl-2-(trifluoromethyl)-2H-1-benzopyran-3-carboxylic acid;
6-bromo-3,4-dihydro-8-fluoro-2-(trifluoromethyl)-2H-1-benzopyran-3-carboxylic acid;
3,4-dihydro-6-(4-fluorophenyl)-2-(trifluoromethyl)-2H-1-benzopyran-3-carboxylic acid;
3,4-dihydro-6-phenyl-2-(trifluoromethyl)-2H-1-benzopyran-3-carboxylic acid;
8-chloro-3,4-dihydro-6-fluoro-2-(trifluoromethyl)-2H-1-benzopyran-3-carboxylic acid;
3,4-dihydro-6,8-diiodo-2-(trifluoromethyl)-2H-1-benzopyran-3-carboxylic acid;
6-(5-chloro-2-thienyl)-3,4-dihydro-2-(trifluoromethyl)-2H-1-benzopyran-3-carboxylic acid;
3,4-dihydro-6-(2-thienyl)-2-(trifluoromethyl)-2H-1-benzopyran-3-carboxylic acid;
6-(4-chlorophenyl)-3,4-dihydro-2-(trifluoromethyl)-2H-1-benzopyran-3-carboxylic acid;
6-(4-bromophenyl)-3,4-dihydro-2-(trifluoromethyl)-2H-1-benzopyran-3-carboxylic acid;
3,4-dihydro-6-(ethynyl)-2-(trifluoromethyl)-2H-1-benzopyran-3-carboxylic acid;
3,4-dihydro-6-methyl-2-(trifluoromethyl)-2H-1-benzopyran-3-carboxylic acid;

6-chloro-3,4-dihydro-8-(4-methoxyphenyl)-2-trifluoromethyl-2H-1-benzopyran-3-carboxylic acid;
6-chloro-3,4-dihydro-2-(trifluoromethyl)-4-ethenyl-2H-1-benzopyran-3-carboxylic acid;
6-chloro-3,4-dihydro-2-(trifluoromethyl)-4-phenyl-2H-1-benzopyran-3-carboxylic acid;
6-chloro-3,4-dihydro-4-(2-thienyl)-2-(trifluoromethyl)-2H-1-benzopyran-3-carboxylic acid;
3,4-dihydro-6-(2,2,2-trifluoro-1-hydroxyethyl)-2-(trifluoromethyl)-2H-1-benzopyran-3-carboxylic acid;
3,4-dihydro-6-methyl-2-(trifluoromethyl)-2H-1-benzothiopyran-3-carboxylic acid;
3,4-dihydro-6,8-dimethyl-2-(trifluoromethyl)-2H-1-benzothiopyran-3-carboxylic acid;
3,4-dihydro-6-(1,1-dimethylethyl)-2-(trifluoromethyl)-2H-1-benzothiopyran-3-carboxylic acid;
3,4-dihydro-7-methyl-2-(trifluoromethyl)-2H-1-benzothiopyran-3-carboxylic acid;
3,4-dihydro-6,7-dimethyl-2-(trifluoromethyl)-2H-1-benzothiopyran-3-carboxylic acid;
3,4-dihydro-8-methyl-2-(trifluoromethyl)-2H-1-benzothiopyran-3-carboxylic acid;
3,4-dihydro-2-(trifluoromethyl)-2H-1-benzothiopyran-3-carboxylic acid;
6-chloro-3,4-dihydro-7-methyl-2-(trifluoromethyl)-2H-1-benzothiopyran-3-carboxylic acid;
7-chloro-3,4-dihydro-2-(trifluoromethyl)-2H-1-benzothiopyran-3-carboxylic acid;
6,7-dichloro-3,4-dihydro-2-(trifluoromethyl)-2H-1-benzothiopyran-3-carboxylic acid;
3,4-dihydro-2-(trifluoromethyl)-6-[(trifluoromethyl)thio]-2H-1-benzothiopyran-3-carboxylic acid;
6,8-dichloro-3,4-dihydro-2-trifluoromethyl-2H-1-benzothiopyran-3-carboxylic acid;
6-chloro-1,2,3,4-tetrahydro-2-(trifluoromethyl)-3-quinolinecarboxylic acid;
6,8-dichloro-1,2,3,4-tetrahydro-2-(trifluoromethyl)-3-quinolinecarboxylic acid;
6,7-difluoro-1,2,3,4-tetrahydro-2-(trifluoromethyl)-3-quinolinecarboxylic acid;
6-iodo-1,2,3,4-tetrahydro-2-(trifluoromethyl)-3-quinolinecarboxylic acid;
6-bromo-1,2,3,4-tetrahydro-2-(trifluoromethyl)-3-quinolinecarboxylic acid;
1,2,3,4-tetrahydro-6-(trifluoromethoxy)-2-(trifluoromethyl)-3-quinolinecarboxylic acid;
6-(trifluoromethyl)-1,2,3,4-tetrahydro-2-(trifluoromethyl)-3-quinolinecarboxylic acid;
6-cyano-1,2,3,4-tetrahydro-2-(trifluoromethyl)-3-quinolinecarboxylic acid;
6-chloro-1,2,3,4-tetrahydro-1-methyl-2-(trifluoromethyl)-3-quinolinecarboxylic acid;
6-chloro-1,2,3,4-tetrahydro-2-(trifluoromethyl)-1-[[4-(trifluoromethyl)phenyl]methyl]-3-quinolinecarboxylic acid;
6-chloro-1-[(4-chlorophenyl)methyl]-1,2,3,4-tetrahydro-2-(trifluoromethyl)-3-quinolinecarboxylic acid;
6-chloro-1,2,3,4-tetrahydro-2-(trifluoromethyl)-1-[[4-(methoxy)phenyl]methyl]-3-quinolinecarboxylic acid;
6-chloro-1-[(4-cyanophenyl)methyl]-1,2,3,4-tetrahydro-2-(trifluoromethyl)-3-quinolinecarboxylic acid;
6-chloro-1,2,3,4-tetrahydro-1-[(4-nitrophenyl)methyl]-2-(trifluoromethyl)-3-quinolinecarboxylic acid;
6-chloro-1,2,3,4-tetrahydro-1-ethyl-2-(trifluoromethyl)-3-quinolinecarboxylic acid;
6-chloro-2-(triflouromethyl)-1,2,3,4-tetrahydro[1,8]napthyridine-3-carboxylic acid;
6-chloro-3,4-dihydro-7-[(3-pyridyl-N-oxide)oxy]-2-(trifluoromethyl)-2H-1-benzopyran-3-carboxylic acid
6-chloro-3,4-dihydro-7-[(2-pyridyl-N-oxide)oxy]-2-(trifluoromethyl)-2H-1-benzopyran-3-carboxylic acid;
6-chloro-7-[(3-chloro-2-pyridyl-{N-oxide})oxy]-3,4-dihydro-2-(trifluoromethyl)-2H-1-benzopyran-3-carboxylic acid;
6-chloro-7-[(4-chloro-2-pyridyl-{N-oxide})oxy]-3,4-dihydro-2-(trifluoromethyl)-2H-1-benzopyran-3-carboxylic acid;
6-chloro-7-[(5-chloro-2-pyridyl-{N-oxide})oxy]-3,4-dihydro-2-(trifluoromethyl)-2H-1-benzopyran-3-carboxylic acid;
6-chloro-7-[(6-chloro-2-pyridyl-{N-oxide})oxy]-3,4-dihydro-2-(trifluoromethyl)-2H-1-benzopyran-3-carboxylic acid;
6-chloro-3,4-dihydro-7-[(2-pyridyl-N-oxide)thio]-2-(trifluoromethyl)-2H-1-benzopyran-3-carboxylic acid;
6-chloro-7-[(3-chloro-2-pyridyl-{N-oxide})thio]-3,4-dihydro-2-(trifluoromethyl)-2H-1-benzopyran-3-carboxylic acid;
6-chloro-7-[(2-pyridyl-N-oxide)oxy]-2-(trifluoromethyl)-2H-12,3,4-tetrahydroquinoline-3-carboxylic acid;
6-chloro-7-[(3-chloro-2-pyridyl-{N-oxide})oxy]-2-(trifluoromethyl)-2H-1,2,3,4-tetrahydroquinoline-3-carboxylic acid;
6-chloro-7-[(2-pyridyl-N-oxide)thio]-2-(trifluoromethyl)-2H-12,3,4-tetrahydroquinoline-3-carboxylic acid;
6-chloro-7-[(3-chloro-2-pyridyl-{N-oxide})thio]-2-(trifluoromethyl)-2H-1,2,3,4-tetrahydroquinoline-3-carboxylic acid;
6-chloro-3,4-dihydro-7-[(2-pyridyl-N-oxide)oxy]-2-(trifluoromethyl)-2H-1-benzothiopyran-3-carboxylic acid;
6-chloro-7-[(3-chloro-2-pyridyl-{N-oxide})oxy]-3,4-dihydro-2-(trifluoromethyl)-2H-1-benzothiopyran-3-carboxylic acid;
6-chloro-3,4-dihydro-7-[(2-pyridyl-N-oxide)thio]-2-(trifluoromethyl)-2H-1-benzothiopyran-3-carboxylic acid;
6-chloro-7-[(3-chloro-2-pyridyl-{N-oxide})thio]-3,4-dihydro-2-(trifluoromethyl)-2H-1-benzothiopyran-3-carboxylic acid;
3,4-dihydro-7-phenoxy-2-(trifluoromethyl)-2H-1-benzopyran-3-carboxylic acid;
6-chloro-3,4-dihydro-7-phenoxy-2-(trifluoromethyl)-2H-1-benzopyran-3-carboxylic acid;
6-chloro-3,4-dihydro-7-(2-hydroxy-1,1-dimethylethyl)-2-(trifluoromethyl)-2H-1-benzopyran-3-carboxylic acid;
3,4-dihydro-7-(2-hydroxy-1,1-dimethylethyl)-2-(trifluoromethyl)-2H-1-benzopyran-3-carboxylic;
6-chloro-3,4-dihydro-7-iodo-2-(trifluoromethyl)-2H-1-benzopyran-3-carboxylic acid;
6-chloro-3,4-dihydro-7-ethynyl-2-(trifluoromethyl)-2H-1-benzopyran-3-carboxylic acid;
6-chloro-3,4-dihydro-7-ethenyl-2-(trifluoromethyl)-2H-1-benzopyran-3-carboxylic acid;
6-chloro-3,4-dihydro-7-(4-methoxyphenoxy)-2-(trifluoromethyl)-2H-1-benzopyran-3-carboxylic acid;
6-chloro-7-(4-chlorophenoxy)-3,4-dihydro-2-(trifluoromethyl)-2H-1-benzopyran-3-carboxylic acid;
6-chloro-7-(4-chlorophenoxy)-3,4-dihydro-2-(trifluoromethyl)-2H-1-benzopyran-3-carboxylic acid;
6-chloro-7-(4-cyanophenoxy)-3,4-dihydro-2-(trifluoromethyl)-2H-1-benzopyran-3-carboxylic acid;
6-chloro-3,4-dihydro-7-[4-(trifluoromethyl)phenoxy]-2-(trifluoromethyl)-2H-1-benzopyran-3-carboxylic acid;

6-chloro-3,4-dihydro-7-[4-(trifluoromethoxy)phenoxy]-2-(trifluoromethyl)-2H-1-benzopyran-3-carboxylic acid;
6-chloro-7-(2-bromo-4-chlorophenoxy)-3,4-dihydro-2-(trifluoromethyl)-2H-1-benzopyran-3-carboxylic acid;
6-chloro-7-[(6-bromo-2-naphthyl)oxy]-3,4-dihydro-2-(trifluoromethyl)-2H-1-benzopyran-3-carboxylic acid;
6-chloro-3,4-dihydro-7-(2,6-dimethylphenoxy)-2-(trifluoromethyl)-2H-1-benzopyran-3-carboxylic acid;
6-chloro-3,4-dihydro-7-[(4-methoxyphenyl)thio]-2-(trifluoromethyl)-2H-1-benzopyran-3-carboxylic acid;
6-chloro-7-[(4-chlorophenyl)thio]-3,4-dihydro-2-(trifluoromethyl)-2H-1-benzopyran-3-carboxylic acid;
6-chloro-7-[(4-chlorophenyl)sulfinyl]-3,4-dihydro-2-(trifluoromethyl)-2H-1-benzopyran-3-carboxylic acid;
6-chloro-7-[(4-chlorophenyl)sulfonyl]-3,4-dihydro-2-(trifluoromethyl)-2H-1-benzopyran-3-carboxylic acid;
6-chloro-3,4-dihydro-7-phenylthio-2-(trifluoromethyl)-2H-1-benzopyran-3-carboxylic acid;
6-chloro-7-(3-chlorophenoxy)-3,4-dihydro-2-(trifluoromethyl)-2H-1-benzopyran-3-carboxylic acid;
6-chloro-7-(2,4-dichlorophenoxy)-3,4-dihydro-2-(trifluoromethyl)-2H-1-benzopyran-3-carboxylic acid;
6-chloro-7-(3,4-difluorophenoxy)-3,4-dihydro-2-(trifluoromethyl)-2H-1-benzopyran-3-carboxylic acid;
6-chloro-7-[(6-chloro-2-pyridinyl)oxy]-3,4-dihydro-2-(trifluoromethyl)-2H-1-benzopyran-3-carboxylic acid;
6-chloro-7-[(2-chloro-3-pyridinyl)oxy]-3,4-dihydro-2-(trifluoromethyl)-2H-1-benzopyran-3-carboxylic acid;
6-chloro-3,4-dihydro-7-[(3-pyridinyl)oxy]-2-(trifluoromethyl)-2H-1-benzopyran-3-carboxylic acid;
6-chloro-3,4-dihydro-7-[(2-pyridinyl)oxy]-2-(trifluoromethyl)-2H-1-benzopyran-3-carboxylic acid;
6-chloro-3,4-dihydro-7-(4-nitrophenoxy)-2-(trifluoromethyl)-2H-1-benzopyran-3-carboxylic acid;
6-chloro-7-(2-chlorophenoxy)-3,4-dihydro-2-(trifluoromethyl)-2H-1-benzopyran-3-carboxylic acid;
6-chloro-7-(4-chloro-3-fluorophenoxy)-3,4-dihydro-2-(trifluoromethyl)-2H-1-benzopyran-3-carboxylic acid;
6-chloro-7-(4-carboxyphenoxy)-3,4-dihydro-2-(trifluoromethyl)-2H-1-benzopyran-3-carboxylic acid;
6-chloro-7-(2-chloro-4-carboxyphenoxy)-3,4-dihydro-2-(trifluoromethyl)-2H-1-benzopyran-3-carboxylic acid;
6-chloro-7-(3-carboxyphenoxy)-3,4-dihydro-2-(trifluoromethyl)-2H-1-benzopyran-3-carboxylic acid;
6-chloro-3,4-dihydro-7-(2,2,2-trifluoroethoxy)-2-(trifluoromethyl)-2H-1-benzopyran-3-carboxylic acid;
1,2,3,4-tetrahydro-6-ethynyl-2-(trifluoromethyl)-3-quinolinecarboxylic acid;
1,2,3,4-tetrahydro-6-phenylethynyl-2-(trifluoromethyl)-3-quinolinecarboxylic acid;
6-chloro-7-(3,4-dichlorophenoxy)-3,4-dihydro-2-(trifluoromethyl)-2H-1-benzopyran-3-carboxylic acid;
6-chloro-7-(3-bromo-4-chlorophenoxy)-3,4-dihydro-2-(trifluoromethyl)-2H-1-benzopyran-3-carboxylic acid;
6-chloro-7-(4-bromo-3-chlorophenoxy)-3,4-dihydro-2-(trifluoromethyl)-2H-1-benzopyran-3-carboxylic acid;
6-chloro-7-(3,4-dibromophenoxy)-3,4-dihydro-2-(trifluoromethyl)-2H-1-benzopyran-3-carboxylic acid;
6-chloro-7-[4-chloro-3-(trifluoromethyl)phenoxy]-3,4-dihydro-2-(trifluoromethyl)-2H-1-benzopyran-3-carboxylic acid;
6-chloro-7-[3-chloro-4-(trifluoromethyl)phenoxy]-3,4-dihydro-2-(trifluoromethyl)-2H-1-benzopyran-3-carboxylic acid;
6-chloro-7-(2,6-dichlorophenoxy)-3,4-dihydro-2-(trifluoromethyl)-2H-1-benzopyran-3-carboxylic acid;
6-chloro-7-(2,6-dibromophenoxy)-3,4-dihydro-2-(trifluoromethyl)-2H-1-benzopyran-3-carboxylic acid;
6-chloro-7-(2,6-difluorophenoxy)-3,4-dihydro-2-(trifluoromethyl)-2H-1-benzopyran-3-carboxylic acid;
6-chloro-7-(2,5-dichlorophenoxy)-3,4-dihydro-2-(trifluoromethyl)-2H-1-benzopyran-3-carboxylic acid;
6-chloro-7-(2,5-dibromophenoxy)-3,4-dihydro-2-(trifluoromethyl)-2H-1-benzopyran-3-carboxylic acid;
6-chloro-7-(2,5-difluorophenoxy)-3,4-dihydro-2-(trifluoromethyl)-2H-1-benzopyran-3-carboxylic acid;
6-chloro-7-(2,3-dichlorophenoxy)-v2-(trifluoromethyl)-1-benzopyran-3-carboxylic acid;
6-chloro-7-(2,3-dibromophenoxy)-3,4-dihydro-2-(trifluoromethyl)-2H-1-benzopyran-3-carboxylic acid;
6-chloro-7-(2,3-difluorophenoxy)-3,4-dihydro-2-(trifluoromethyl)-2H-1-benzopyran-3-carboxylic acid;
6-chloro-7-(4-chloro-3-cyanophenoxy)-3,4-dihydro-2-(trifluoromethyl)-2H-1-benzopyran-3-carboxylic acid;
6-chloro-3,4-dihydro-7-(3-tert-butylphenoxy)-2-(trifluoromethyl)-2H-1-benzopyran-3-carboxylic acid;
6-chloro-3,4-dihydro-7-(2-tert-butylphenoxy)-2-(trifluoromethyl)-2H-1-benzopyran-3-carboxylic acid;
6-chloro-7-(4-chloro-3-tert-butylphenoxy)-3,4-dihydro-2-(trifluoromethyl)-2H-1-benzopyran-3-carboxylic acid;
6-chloro-7-(4-chloro-2-tert-butylphenoxy)-3,4-dihydro-2-(trifluoromethyl)-2H-1-benzopyran-3-carboxylic acid;
6-chloro-7-(2-chloro-3-tert-butyl phenoxy)-3,4-dihydro-2-(trifluoromethyl)-2H-1-benzopyran-3-carboxylic acid;
6-chloro-7-(3-chloro-2-tert-butyl phenoxy)-3,4-dihydro-2-(trifluoromethyl)-2H-1-benzopyran-3-carboxylic acid;
6-chloro-3,4-dihydro-7-(3-thienyloxy)-2-(trifluoromethyl)-2H-1-benzopyran-3-carboxylic acid;
6-chloro-7-(2-chloro-3-thienyloxy)-3,4-dihydro-2-(trifluoromethyl)-2H-1-benzopyran-3-carboxylic acid;
6-chloro-7-(4-chloro-3-thienyloxy)-3,4-dihydro-2-(trifluoromethyl)-2H-1-benzopyran-3-carboxylic acid;
6-chloro-7-(5-chloro-3-thienyloxy)-3,4-dihydro-2-(trifluoromethyl)-2H-1-benzopyran-3-carboxylic acid;
6-chloro-7-(2,5-dichloro-3-thienyloxy)-3,4-dihydro-2-(trifluoromethyl)-2H-1-benzopyran-3-carboxylic acid;
6-chloro-7-(2,4-dichloro-3-thienyloxy)-3,4-dihydro-2-(trifluoromethyl)-2H-1-benzopyran-3-carboxylic acid;
6-chloro-7-[(3-chloro-2-pyridyl)oxy]-3,4-dihydro-2-(trifluoromethyl)-2H-1-benzopyran-3-carboxylic acid;
6-chloro-7-[(4-chloro-2-pyridyl)oxy]-3,4-dihydro-2-(trifluoromethyl)-2H-1-benzopyran-3-carboxylic acid;
6-chloro-7-[(3-chloro-2-pyridyl)oxy]-3,4-dihydro-2-(trifluoromethyl)-2H-1-benzopyran-3-carboxylic acid;
6-chloro-7-[(5-chloro-2-pyridyl)oxy]-3,4-dihydro-2-(trifluoromethyl)-2H-1-benzopyran-3-carboxylic acid;
6-chloro-7-[(6-chloro-2-pyridyl)oxy]-3,4-dihydro-2-(trifluoromethyl)-2H-1-benzopyran-3-carboxylic acid;
6-chloro-7-[(5,6-dichloro-2-pyridyl)oxy]-3,4-dihydro-2-(trifluoromethyl)-2H-1-benzopyran-3-carboxylic acid;
6-chloro-7-[(3,4-dichloro-2-pyridyl)oxy]-3,4-dihydro-2-(trifluoromethyl)-2H-1-benzopyran-3-carboxylic acid;
6-chloro-7-[(4,5-dichloro-2-pyridyl)oxy]-3,4-dihydro-2-(trifluoromethyl)-2H-1-benzopyran-3-carboxylic acid;
6-chloro-7-[(3,5-dichloro-2-pyridyl)oxy]-3,4-dihydro-2-(trifluoromethyl)-2H-1-benzopyran-3-carboxylic acid;
6-chloro-7-[(3,6-dichloro-2-pyridyl)oxy]-3,4-dihydro-2-(trifluoromethyl)-2H-1-benzopyran-3-carboxylic acid;
6-chloro-7-[(4,5-dichloro-2-pyridyl)oxy]-3,4-dihydro-2-(trifluoromethyl)-2H-1-benzopyran-3-carboxylic acid;
6-chloro-7-[(4,6-dichloro-2-pyridyl)oxy]-3,4-dihydro-2-(trifluoromethyl)-2H-1-benzopyran-3-carboxylic acid;
6-chloro-7-[(5,6-dichloro-2-pyridyl)oxy]-3,4-dihydro-2-(trifluoromethyl)-2H-1-benzopyran-3-carboxylic acid;
6-chloro-3,4-dihydro-7-[(2-quinolyl)oxy]-2-(trifluoromethyl)-2H-1-benzopyran-3-carboxylic acid;

3,4-dihydro-2-trifluoromethyl-2H-naphtho[1,2-b]pyran-3-carboxylic acid;

3,4-dihydro-2-trifluoromethyl-3H-naphtho[2,1-b]pyran-3-carboxylic acid;

3,4-dihydro-2-trifluoromethyl-2H-naphtho[2,3-b]pyran-3-carboxylic acid;

3,4-dihydro-5-(hydroxymethyl)-8-methyl-2-(trifluoromethyl)-2H-pyrano[2,3-c]pyridine-3-carboxylic acid;

3,4-dihydro-6-(trifluoromethyl)-6H-1,3-dioxolo[4,5-g][1]benzopyran-7-carboxylic acid; and 3,4-dihydro-3-(trifluoromethyl)-3H-benzofuro[3,2-f][1]benzopyran-2-carboxylic acid.

A preferred family of specific compounds of particular interest within Formulas I-I" consists of compounds as follows:

(2S,3R)-3,4-dihydro-7-phenoxy-2-(trifluoromethyl)-2H-1-benzopyran-3-carboxylic acid;

(2S,3R)-6-chloro-3,4-dihydro-7-phenoxy-2-(trifluoromethyl)-2H-1-benzopyran-3-carboxylic acid;

(2S,3R)-6-chloro-3,4-dihydro-7-(2-hydroxy-1,1-dimethylethyl)-2-(trifluoromethyl)-2H-1-benzopyran-3-carboxylic acid;

(2S,3R)-3,4-dihydro-7-(2-hydroxy-1,1-dimethylethyl)-2-(trifluoromethyl)-2H-1-benzopyran-3-carboxylic; (2S,3R)-6-chloro-3,4-dihydro-7-iodo-2-(trifluoromethyl)-2H-1-benzopyran-3-carboxylic acid;

(2S,3R)-6-chloro-3,4-dihydro-7-ethynyl-2-(trifluoromethyl)-2H-1-benzopyran-3-carboxylic acid;

(2S,3R)-6-chloro-3,4-dihydro-7-ethenyl-2-(trifluoromethyl)-2H-1-benzopyran-3-carboxylic acid;

(2S,3R)-6-chloro-3,4-dihydro-7-(4-methoxyphenoxy)-2-(trifluoromethyl)-2H-1-benzopyran-3-carboxylic acid;

(2S,3R)-6-chloro-7-(4-chlorophenoxy)-3,4-dihydro-2-(trifluoromethyl)-2H-1-benzopyran-3-carboxylic acid;

(2S,3R)-6-chloro-7-(4-chlorophenoxy)-3,4-dihydro-2-(trifluoromethyl)-2H-1-benzopyran-3-carboxylic acid;

(2S,3R)-6-chloro-7-(4-cyanophenoxy)-3,4-dihydro-2-(trifluoromethyl)-2H-1-benzopyran-3-carboxylic acid;

(2S,3R)-6-chloro-7-[4-(trifluoromethyl)phenoxy]-3,4-dihydro-2-(trifluoromethyl)-2H-1-benzopyran-3-carboxylic acid;

(2S,3R)-6-chloro-7-[4-(trifluoromethoxy)phenoxy]-3,4-dihydro-2-(trifluoromethyl)-2H-1-benzopyran-3-carboxylic acid;

(2S,3R)-6-chloro-7-(2-bromo-4-chlorophenoxy)-3,4-dihydro-2-(trifluoromethyl)-2H-1-benzopyran-3-carboxylic acid;

(2S,3R)-6-chloro-7-[(6-bromo-2-naphthyl) oxy]-3,4-dihydro-2-(trifluoromethyl)-2H-1-benzopyran-3-carboxylic acid;

(2S,3R)-6-chloro-7-(2,6-dimethylphenoxy)-3,4-dihydro-2-(trifluoromethyl)-2H-1-benzopyran-3-carboxylic acid;

(2S,3R)-6-chloro-7-[(4-methoxyphenyl)thio]-3,4-dihydro-2-(trifluoromethyl)-2H-1-benzopyran-3-carboxylic acid;

(2S,3R)-6-chloro-7-[(4-chlorophenyl)thio]-3,4-dihydro-2-(trifluoromethyl)-2H-1-benzopyran-3-carboxylic acid;

(2S,3R)-6-chloro-7-[(4-chlorophenyl)sulfinyl]-3,4-dihydro-2-(trifluoromethyl)-2H-1-benzopyran-3-carboxylic acid;

(2S,3R)-6-chloro-7-[(4-chlorophenyl)sulfonyl]-3,4-dihydro-2-(trifluoromethyl)-2H-1-benzopyran-3-carboxylic acid;

(2S,3R)-6-chloro-7-phenylthio-3,4-dihydro-2-(trifluoromethyl)-2H-1-benzopyran-3-carboxylic acid;

(2S,3R)-6-chloro-7-(3-chlorophenoxy)-3,4-dihydro-2-(trifluoromethyl)-2H-1-benzopyran-3-carboxylic acid;

(2S,3R)-6-chloro-7-(2,4-dichlorophenoxy)-3,4-dihydro-2-(trifluoromethyl)-2H-1-benzopyran-3-carboxylic acid;

(2S,3R)-6-chloro-7-(3,4-difluorophenoxy)-3,4-dihydro-2-(trifluoromethyl)-2H-1-benzopyran-3-carboxylic acid;

(2S,3R)-6-chloro-7-[(6-chloro-2-pyridinyl)oxy]-3,4-dihydro-2-(trifluoromethyl)-2H-1-benzopyran-3-carboxylic acid;

(2S,3R)-6-chloro-7-[(2-chloro-3-pyridinyl)oxy]-3,4-dihydro-2-(trifluoromethyl)-2H-1-benzopyran-3-carboxylic acid;

(2S,3R)-6-chloro-7-[(3-pyridinyl)oxy]-3,4-dihydro-2-(trifluoromethyl)-2H-1-benzopyran-3-carboxylic acid;

(2S,3R)-6-chloro-7-[(2-pyridinyl)oxy]-3,4-dihydro-2-(trifluoromethyl)-2H-1-benzopyran-3-carboxylic acid;

(2S,3R)-6-chloro-7-(4-nitrophenoxy)-3,4-dihydro-2-(trifluoromethyl)-2H-1-benzopyran-3-carboxylic acid;

(2S,3R)-6-chloro-7-(2-chlorophenoxy)-3,4-dihydro-2-(trifluoromethyl)-2H-1-benzopyran-3-carboxylic acid;

(2S,3R)-6-chloro-7-(4-chloro-3-fluorophenoxy)-3,4-dihydro-2-(trifluoromethyl)-2H-1-benzopyran-3-carboxylic acid;

(2S,3R)-6-chloro-7-(4-carboxyphenoxy)-3,4-dihydro-2-(trifluoromethyl)-2H-1-benzopyran-3-carboxylic acid;

(2S,3R)-6-chloro-7-(2-chloro-4-carboxyphenoxy)-3,4-dihydro-2-(trifluoromethyl)-2H-1-benzopyran-3-carboxylic acid;

(2S,3R)-6-chloro-7-(3-carboxyphenoxy)-3,4-dihydro-2-(trifluoromethyl)-2H-1-benzopyran-3-carboxylic acid;

(2S,3R)-6-chloro-7-(2,2,2-trifluoroethoxy)-3,4-dihydro-2-(trifluoromethyl)-2H-1-benzopyran-3-carboxylic acid;

(2S,3R)-6-chloro-1,2,3,4-tetrahydro-8-methyl-2-(trifluoromethyl)-3-quinolinecarboxylic acid;

(2S,3R)-1,2,3,4-tetrahydro-5-methyl-2-(trifluoromethyl)-3-quinolinecarboxylic acid;

(2S,3R)-1,2,3,4-tetrahydro-6-(4-fluorophenyl)-2-(trifluoromethyl)-3-quinolinecarboxylic acid;

(2S,3R)-1,2,3,4-tetrahydro-6-ethynyl-2-(trifluoromethyl)-3-quinolinecarboxylic acid;

(2S,3R)-8-bromo-1,2,3,4-tetrahydro-6-methyl-2-(trifluoromethyl)-3-quinolinecarboxylic acid;

(2S,3R)-1,2,3,4-tetrahydro-6-phenylethynyl-2-(trifluoromethyl)-3-quinolinecarboxylic acid;

(2S,3R)-6-chloro-3,4-dihydro-2-(trifluoromethyl)-2H-1-benzopyran-3-carboxylic acid;

(2S,3R)-7-ethyl-3,4-dihydro-2-trifluoromethyl-2H-1-benzopyran-3-carboxylic acid;

(2S,3R)-7-methyl-3,4-dihydro-2-trifluoromethyl-2H-1-benzopyran-3-carboxylic acid;

(2S,3R)-2,7-bis(trifluoromethyl)-2H-1-benzopyran-3-carboxylic acid;

(2S,3R)-7-bromo-3,4-dihydro-2-trifluoromethyl-2H-1-benzopyran-3-carboxylic acid;

(2S,3R)-6-chloro-7-methyl-3,4-dihydro-2-trifluoromethyl-2H-1-benzopyran-3-carboxylic acid;

(2S,3R)-8-(1-methylethyl)-3,4-dihydro-2-trifluoromethyl-2H-1-benzopyran-3-carboxylic acid;

(2S,3R)-6-chloro-3,4-dihydro-7-(1,1-dimethylethyl)-2-(trifluoromethyl)-2H-1-benzopyran-3-carboxylic acid;

(2S,3R)-6-chloro-8-(1-methylethyl)-3,4-dihydro-2-trifluoromethyl-2H-1-benzopyran-3-carboxylic acid;

(2S,3R)-3,4-dihydro-2-trifluoromethyl-2H-1-benzopyran-3-carboxylic acid;

(2S,3R)-8-ethoxy-3,4-dihydro-2-trifluoromethyl-2H-1-benzopyran-3-carboxylic acid;

(2S,3R)-7-(1,1-dimethylethyl)-3,4-dihydro-2-trifluoromethyl-2H-1-benzopyran-3-carboxylic acid;

(2S,3R)-6-bromo-3,4-dihydro-2-trifluoromethyl-2H-1-benzopyran-3-carboxylic acid;

(2S,3R)-8-chloro-3,4-dihydro-2-trifluoromethyl-2H-1-benzopyran-3-carboxylic acid;

(2S,3R)-8-bromo-6-chloro-3,4-dihydro-2-trifluoromethyl-2H-1-benzopyran-3-carboxylic acid;
rel-(2R,3S)-3,4-dihydro-6-trifluoromethoxy-2-(trifluoromethyl)-2H-1-benzopyran-3-carboxylic acid;
(2S,3R)-8-fluoro-3,4-dihydro-2-trifluoromethyl-2H-1-benzopyran-3-carboxylic acid;
(2S,3R)-5,7-dichloro-3,4-dihydro-2-trifluoromethyl-2H-1-benzopyran-3-carboxylic acid;
(2S,3R)-7,8-dichloro-3,4-dihydro-2-trifluoromethyl-2H-1-benzopyran-3-carboxylic acid;
(2S,3R)-7-isopropyloxy-3,4-dihydro-2-trifluoromethyl-2H-1-benzopyran-3-carboxylic acid;
(2S,3R)-8-phenyl-3,4-dihydro-2-trifluoromethyl-2H-1-benzopyran-3-carboxylic acid;
(2S,3R)-7,8-dimethyl-3,4-dihydro-2-trifluoromethyl-2H-1-benzopyran-3-carboxylic acid;
(2S,3R)-6,8-bis(1,1-dimethylethyl)-3,4-dihydro-2-trifluoromethyl-2H-1-benzopyran-3-carboxylic acid;
(2S,3R)-7-chloro-3,4-dihydro-2-trifluoromethyl-2H-1-benzopyran-3-carboxylic acid;
(2S,3R)-7-(1-methylethyl)-3,4-dihydro-2-trifluoromethyl-2H-1-benzopyran-3-carboxylic acid;
(2S,3R)-7-phenyl-3,4-dihydro-2-trifluoromethyl-2H-1-benzopyran-3-carboxylic acid;
(2S,3R)-6-chloro-7-ethyl-3,4-dihydro-2-trifluoromethyl-2H-1-benzopyran-3-carboxylic acid;
(2S,3R)-8-ethyl-3,4-dihydro-2-trifluoromethyl-2H-1-benzopyran-3-carboxylic acid;
(2S,3R)-6-chloro-8-ethyl-3,4-dihydro-2-trifluoromethyl-2H-1-benzopyran-3-carboxylic acid;
(2S,3R)-6-chloro-7-phenyl-3,4-dihydro-2-trifluoromethyl-2H-1-benzopyran-3-carboxylic acid;
(2S,3R)-6,7-dichloro-3,4-dihydro-2-trifluoromethyl-2H-1-benzopyran-3-carboxylic acid;
(2S,3R)-6,8-dichloro-3,4-dihydro-2-trifluoromethyl-2H-1-benzopyran-3-carboxylic acid;
(2S,3R)-6,8-dibromo-3,4-dihydro-2-trifluoromethyl-2H-1-benzopyran-3-carboxylic acid;
(2S,3R)-6,8-dimethoxy-3,4-dihydro-2-trifluoromethyl-2H-1-benzopyran-3-carboxylic acid;
(2S,3R)-6-nitro-3,4-dihydro-2-trifluoromethyl-2H-1-benzopyran-3-carboxylic acid;
(2S,3R)-6-amino-3,4-dihydro-2-trifluoromethyl-2H-1-benzopyran-3-carboxylic acid;
(2S,3R)-ethyl 6-amino-3,4-dihydro-trifluoromethyl-2H-1-benzopyran-3-carboxylate;
(2S,3R)-6-chloro-3,4-dihydro-8-methyl-2-trifluoromethyl-2H-1-benzopyran-3-carboxylic acid;
(2S,3R)-8-chloro-3,4-dihydro-6-methyl-2-trifluoromethyl-2H-1-benzopyran-3-carboxylic acid;
(2S,3R)-8-chloro-3,4-dihydro-6-methoxy-2-trifluoromethyl-2H-1-benzopyran-3-carboxylic acid;
(2S,3R)-6,8-difluoro-3,4-dihydro-2-trifluoromethyl-2H-1-benzopyran-3-carboxylic acid;
(2S,3R)-6-bromo-8-chloro-3,4-dihydro-2-trifluoromethyl-2H-1-benzopyran-3-carboxylic acid;
(2S,3R)-8-bromo-3,4-dihydro-6-fluoro-2-trifluoromethyl-2H-1-benzopyran-3-carboxylic acid;
(2S,3R)-8-bromo-3,4-dihydro-6-methyl-2-trifluoromethyl-2H-1-benzopyran-3-carboxylic acid;
(2S,3R)-8-bromo-3,4-dihydro-5-fluoro-2-trifluoromethyl-2H-1-benzopyran-3-carboxylic acid;
(2S,3R)-6-chloro-3,4-dihydro-8-fluoro-2-trifluoromethyl-2H-1-benzopyran-3-carboxylic acid;
(2S,3R)-6-bromo-3,4-dihydro-8-methoxy-2-trifluoromethyl-2H-1-benzopyran-3-carboxylic acid;
(2S,3R)-7-(N,N-diethylamino)-3,4-dihydro-2-trifluoromethyl-2H-1-benzopyran-3-carboxylic acid;
(2S,3R)-3,4-dihydro-6-[[(phenylmethyl)amino]sulfonyl]-2-trifluoromethyl-2H-1-benzopyran-3-carboxylic acid;
(2S,3R)-3,4-dihydro-6-[(dimethylamino)sulfonyl]-2-trifluoromethyl-2H-1-benzopyran-3-carboxylic acid;
(2S,3R)-6-aminosulfonyl-3,4-dihydro-2-trifluoromethyl-2H-1-benzopyran-3-carboxylic acid;
(2S,3R)-3,4-dihydro-6-(methylamino)sulfonyl-2-trifluoromethyl-2H-1-benzopyran-3-carboxylic acid;
(2S,3R)-3,4-dihydro-6-[(4-morpholino)sulfonyl]-2-trifluoromethyl-2H-1-benzopyran-3-carboxylic acid;
(2S,3R)-3,4-dihydro-6-[(1,1-dimethylethyl)aminosulfonyl]-2-trifluoromethyl-2H-1-benzopyran-3-carboxylic acid;
(2S,3R)-3,4-dihydro-6-[(2-methylpropyl)aminosulfonyl]-2-trifluoromethyl-2H-1-benzopyran-3-carboxylic acid;
(2S,3R)-3,4-dihydro-6-methylsulfonyl-2-trifluoromethyl-2H-1-benzopyran-3-carboxylic acid;
(2S,3R)-8-chloro-3,4-dihydro-6-[[(phenylmethyl)amino]sulfonyl]-2-trifluoromethyl-2H-1-benzopyran-3-carboxylic acid;
(2S,3R)-6-N,N-diethylaminosulfonyl-3,4-dihydro-2-trifluoromethyl-2H-1-benzopyran-3-carboxylic acid;
(2S,3R)-3,4-dihydro-6-phenylacetyl-2-trifluoromethyl-2H-1-benzopyran-3-carboxylic acid;
(2S,3R)-3,4-dihydro-6-(2,2-dimethylpropylcarbonyl)-2-trifluoromethyl-2H-1-benzopyran-3-carboxylic acid;
(2S,3R)-6,8-dichloro-3,4-dihydro-7-methoxy-2-trifluoromethyl-2H-1-benzopyran-3-carboxylic acid;
(2S,3R)-6-chloro-3,4-dihydro-2-trifluoromethyl-2H-1-benzothiopyran-3-carboxylic acid;
(2S,3R)-6-[[(2-furanylmethyl) amino] sulfonyl]-3,4-dihydro-2-(trifluoromethyl)-2H-1-benzopyran-3-carboxylic acid;
(2S,3R)-6-[(phenylmethyl)sulfonyl]-3,4-dihydro-2-(trifluoromethyl)-2H-1-benzopyran-3-carboxylic acid;
(2S,3R)-6-[[(phenylethyl)amino]sulfonyl]-3,4-dihydro-2-(trifluoromethyl)-2H-1-benzopyran-3-carboxylic acid;
(2S,3R)-3,4-dihydro-6-iodo-2-trifluoromethyl-2H-1-benzopyran-3-carboxylic acid;
(2S,3R)-6-chloro-8-iodo-3,4-dihydro-2-(trifluoromethyl)-2H-1-benzopyran-3-carboxylic acid;
(2S,3R)-8-bromo-6-chloro-3,4-dihydro-2-trifluoromethyl-2H-1-benzopyran-3-carboxylic acid;
(2S,3R)-6-formyl-3,4-dihydro-2-(trifluoromethyl)-2H-1-benzopyran-3-carboxylic acid;
(2S,3R)-6-chloro-8-formyl-3,4-dihydro-2-(trifluoromethyl)-2H-1-benzopyran-3-carboxylic acid;
(2S,3R)-6-bromo-7-(1,1-dimethylethyl)-3,4-dihydro-2-(trifluoromethyl)-2H-1-benzopyran-3-carboxylic acid;
rel-(2R,3S)-5,6-dichloro-3,4-dihydro-2-(trifluoromethyl)-2H-1-benzopyran-3-carboxylic acid;
rel-(2R,3S)-6-cyano-3,4-dihydro-2-(trifluoromethyl)-2H-1-benzopyran-3-carboxylic acid;
(2S,3R)-6-hydroxymethyl-3,4-dihydro-2-(trifluoromethyl)-2H-1-benzopyran-3-carboxylic acid;
(2S,3R)-6-(difluoromethyl)-3,4-dihydro-2-(trifluoromethyl)-2H-1-benzopyran-3-carboxylic acid;
(2S,3R)-2,6-bis(trifluoromethyl)-3,4-dihydro-2H-1-benzopyran-3-carboxylic acid;
rel-(2R, 3S)-3,4-dihydro-5,6,7-trichloro-2-(trifluoromethyl)-2H-1-benzopyran-3-carboxylic acid;
rel-(2R,3S)-3,4-dihydro-6,7,8-trichloro-2-(trifluoromethyl)-2H-1-benzopyran-3-carboxylic acid;
(2S,3R)-6-(methylthio)-3,4-dihydro-2-(trifluoromethyl)-2H-1-benzopyran-3-carboxylic acid;
(2S,3R)-6-(methylsulfinyl)-3,4-dihydro-2-(trifluoromethyl)-2H-1-benzopyran-3-carboxylic acid;
rel-(2R,3S)-5,8-dichloro-3,4-dihydro-2-(trifluoromethyl)-2H-1-benzopyran-3-carboxylic acid;

(2S,3R)-6-(pentafluoroethyl)-3,4-dihydro-2-(trifluoromethyl)-2H-1-benzopyran-3-carboxylic acid;
(2S,3R)-6-(1,1-dimethylethyl)-3,4-dihydro-2-(trifluoromethyl)-2H-1-benzopyran-3-carboxylic acid;
(2S,3R)-3,4-dihydro-2-(trifluoromethyl)-6-[(trifluoromethyl)thio]-2H-1-benzothiopyran-3-carboxylic acid;
(2S,3R)-6,8-dichloro-7-methyl-3,4-dihydro-2-(trifluoromethyl)-2H-1-benzopyran-3-carboxylic acid;
(2S,3R)-6-chloro-2,7-bis(trifluoromethyl)-3,4-dihydro-2H-1-benzopyran-3-carboxylic acid;
(2S,3R)-5-methoxy-3,4-dihydro-2-(trifluoromethyl)-2H-1-benzopyran-3-carboxylic acid;
(2S,3R)-6-benzoyl-3,4-dihydro-2-(trifluoromethyl)-2H-1-benzopyran-3-carboxylic acid;
(2S,3R)-6-(4-chlorobenzoyl)-3,4-dihydro-2-(trifluoromethyl)-2H-1-benzopyran-3-carboxylic acid;
(2S,3R)-6-(4-hydroxybenzoyl)-3,4-dihydro-2-(trifluoromethyl)-2H-1-benzopyran-3-carboxylic acid;
(2S,3R)-6-phenoxy-3,4-dihydro-2-(trifluoromethyl)-2H-1-benzopyran-3-carboxylic acid;
(2S,3R)-8-chloro-6-(4-chlorophenoxy)-3,4-dihydro-2-trifluoromethyl-2H-1-benzopyran-3-carboxylic acid;
(2S,3R)-3,4-dihydro-2-(trifluoroinethyl)-6-[4-(trifluoromethyl)phenoxy)-2H-1-benzopyran-3-carboxylic acid;
(2S,3R)-6-(4-methoxyphenoxy)-3,4-dihydro-2-(trifluoromethyl)-2H-1-benzopyran-3-carboxylic acid;
(2S,3R)-6-(3-chloro-4-methoxyphenoxy)-3,4-dihydro-2-(trifluoromethyl)-2H-1-benzopyran-3-carboxylic acid;
(2S,3R)-6-(4-chlorophenoxy)-3,4-dihydro-2-(trifluoromethyl)-2H-1-benzopyran-3-carboxylic acid;
(2S,3R)-8-chloro-3,4-dihydro-2-(trifluoromethyl)-6-[4-(trifluoromethyl)phenoxy]-2H-1-benzopyran-3-carboxylic acid;
(2S,3R)-6-chloro-8-cyano-3,4-dihydro-2-(trifluoromethyl)-2H-1-benzopyran-3-carboxylic acid;
(2S,3R)-6-chloro-8-[(hydroxyimino) methyl]-3,4-dihydro-2-(trifluoromethyl)-2H-1-benzopyran-3-carboxylic acid;
(2S,3R)-6-chloro-8-(hydroxymethyl)-3,4-dihydro-2-(trifluoromethyl)-2H-1-benzopyran-3-carboxylic acid;
(2S,3R)-8-(1H-benzimidazol-2-yl)-6-chloro-3,4-dihydro-2-(trifluoromethyl)-2H-1-benzopyran-3-carboxylic acid;
(2S,3R)-3,4-dihydro-7-(1,1-dimethylethyl)-2-(pentafluoroethyl)-2H-1-benzopyran-3-carboxylic acid;
(2S,3R)-6-chloro-8-(methoxymethyl)-3,4-dihydro-2-(trifluoromethyl)-2H-1-benzopyran-3-carboxylic acid;
(2S,3R)-6-chloro-8-(benzyloxymethyl)-3,4-dihydro-2-(trifluoromethyl)-2H-1-benzopyran-3-carboxylic acid;
(2S,3R)-6-chloro-8-ethenyl-3,4-dihydro-2-(trifluoromethyl)-2H-1-benzopyran-3-carboxylic acid;
(2S,3R)-6-chloro-8-ethynyl-3,4-dihydro-2-(trifluoromethyl)-2H-1-benzopyran-3-carboxylic acid;
(2S,3R)-6-chloro-8-(2-thienyl)-3,4-dihydro-2-(trifluoromethyl)-2H-1-benzopyran-3-carboxylic acid;
(2S,3R)-6-chloro-8-(2-furanyl)-3,4-dihydro-2-(trifluoromethyl)-2H-1-benzopyran-3-carboxylic acid;
(2S,3R)-6-chloro-8-(5-chloro-1-pentynyl)-3,4-dihydro-2-(trifluoromethyl)-2H-1-benzopyran-3-carboxylic acid;
(2S,3R)-6-chloro-8-(1-pentynyl)-3,4-dihydro-2-(trifluoromethyl)-2H-1-benzopyran-3-carboxylic acid;
(2S,3R)-6-chloro-8-(phenylethynyl)-3,4-dihydro-2-(trifluoromethyl)-2H-1-benzopyran-3-carboxylic acid;
(2S,3R)-6-chloro-8-(3,3-dimethyl-1-butynyl)-3,4-dihydro-2-(trifluoromethyl)-2H-1-benzopyran-3-carboxylic acid;
(2S,3R)-6-chloro-8-[(4-chlorophenyl)ethynyl]-3,4-dihydro-2-(trifluoromethyl)-2H-1-benzopyran-3-carboxylic acid;
(2S,3R)-6-chloro-8-[(4-methoxyphenyl) ethynyl]-3,4-dihydro-2-(trifluoromethyl)-2H-1-benzopyran-3-carboxylic acid;
(2S,3R)-6-(phenylethynyl)-3,4-dihydro-2-(trifluoromethyl)-2H-1-benzopyran-3-carboxylic acid;
(2S,3R)-6-chloro-8-(4-chlorophenyl)-3,4-dihydro-2-(trifluoromethyl)-2H-1-benzopyran-3-carboxylic acid;
(2S,3R)-6-chloro-8-(3-methoxyphenyl)-3,4-dihydro-2-(trifluoromethyl)-2H-1-benzopyran-3-carboxylic acid;
(2S,3R)-6-chloro-8-[(4-methylthio)phenyl]-3,4-dihydro-2-(trifluoromethyl)-2H-1-benzopyran-3-carboxylic acid;
(2S,3R)-6-chloro-8-[(4-methylsulfonyl)phenyl]-3,4-dihydro-2-(trifluoromethyl)-2H-1-benzopyran-3-carboxylic acid;
(2S,3R)-6-chloro-8-phenyl-3,4-dihydro-2-(trifluoromethyl)-2H-1-benzopyran-3-carboxylic acid;
(2S,3R)-6-bromo-8-fluoro-3,4-dihydro-2-(trifluoromethyl)-2H-1-benzopyran-3-carboxylic acid;
(2S,3R)-6-(4-fluorophenyl)-3,4-dihydro-2-(trifluoromethyl)-2H-1-benzopyran-3-carboxylic acid;
(2S,3R)-6-phenyl-3,4-dihydro-2-(trifluoromethyl)-2H-1-benzopyran-3-carboxylic acid;
(2S,3R)-8-chloro-6-fluoro-3,4-dihydro-2-(trifluoromethyl)-2H-1-benzopyran-3-carboxylic acid;
(2S,3R)-6,8-diiodo-3,4-dihydro-2-(trifluoromethyl)-2H-1-benzopyran-3-carboxylic acid;
(2S,3R)-6-(5-chloro-2-thienyl)-3,4-dihydro-2-(trifluoromethyl)-2H-1-benzopyran-3-carboxylic acid;
(2S,3R)-6-(2-thienyl)-3,4-dihydro-2-(trifluoromethyl)-2H-1-benzopyran-3-carboxylic acid;
(2S,3R)-6-(4-chlorophenyl)-3,4-dihydro-2-(trifluoromethyl)-2H-1-benzopyran-3-carboxylic acid;
(2S,3R)-6-(4-bromophenyl)-3,4-dihydro-2-(trifluoromethyl)-2H-1-benzopyran-3-carboxylic acid;
(2S,3R)-6-(ethynyl)-3,4-dihydro-2-(trifluoromethyl)-2H-1-benzopyran-3-carboxylic acid;
(2S,3R)-6-methyl-3,4-dihydro-2-(trifluoromethyl)-2H-1-benzopyran-3-carboxylic acid;
(2S,3R)-6-chloro-3,4-dihydro-8-(4-methoxyphenyl)-2-trifluoromethyl-2H-1-benzopyran-3-carboxylic acid;
(2S,3R)-6-chloro-3,4-dihydro-2-(trifluoromethyl)-4-ethenyl-2H-1-benzopyran-3-carboxylic acid;
(2S,3R)-6-chloro-3,4-dihydro-2-(trifluoromethyl)-4-phenyl-2H-1-benzopyran-3-carboxylic acid;
(2S,3R)-6-chloro-4-(2-thienyl)-3,4-dihydro-2-(trifluoromethyl)-2H-1-benzopyran-3-carboxylic acid;
(2S,3R)-6-(2,2,2-trifluoro-1-hydroxyethyl)-3,4-dihydro-2-(trifluoromethyl)-2H-1-benzopyran-3-carboxylic acid;
(2S,3R)-3,4-dihydro-6-methyl-2-(trifluoromethyl)-2H-1-benzothiopyran-3-carboxylic acid;
(2S,3R)-3,4-dihydro-6,8-dimethyl-2-(trifluoromethyl)-2H-1-benzothiopyran-3-carboxylic acid;
(2S,3R)-3,4-dihydro-6-(1,1-dimethylethyl)-2-(trifluoromethyl)-2H-1-benzothiopyran-3-carboxylic acid;
(2S,3R)-3,4-dihydro-7-methyl-2-(trifluoromethyl)-2H-1-benzothiopyran-3-carboxylic acid;
(2S,3R)-3,4-dihydro-6,7-dimethyl-2-(trifluoromethyl)-2H-1-benzothiopyran-3-carboxylic acid;
(2S,3R)-3,4-dihydro-8-methyl-2-(trifluoromethyl)-2H-1-benzothiopyran-3-carboxylic acid;
(2S,3R)-3,4-dihydro-2-(trifluoromethyl)-2H-1-benzothiopyran-3-carboxylic acid;
(2S,3R)-6-chloro-3,4-dihydro-7-methyl-2-(trifluoromethyl)-2H-1-benzothiopyran-3-carboxylic acid;
(2S,3R)-7-chloro-3,4-dihydro-2-(trifluoromethyl)-2H-1-benzothiopyran-3-carboxylic acid;

(2S,3R)-6,7-dichloro-3,4-dihydro-2-(trifluoromethyl)-2H-1-benzothiopyran-3-carboxylic acid;
(2S,3R)-3,4-dihydro-2-(trifluoromethyl)-6-[(trifluoromethyl)thio]-2H-1-benzopyran-3-carboxylic acid;
rel-(2R,3S)-6,8-dichloro-3,4-dihydro-2-(trifluoromethyl)-2H-1-benzothiopyran-3-carboxylic acid;
(2S,3R)-6-chloro-1,2,3,4-tetrahydro-2-(trifluoromethyl)-3-quinolinecarboxylic acid;
(2S,3R)-6,8-dichloro-1,2,3,4-tetrahydro-2-(trifluoromethyl)-3-quinolinecarboxylic acid;
(2S,3R)-6,7-difluoro-1,2,3,4-tetrahydro-2-(trifluoromethyl)-3-quinolinecarboxylic acid;
(2S,3R)-6-iodo-1,2,3,4-tetrahydro-2-(trifluoromethyl)-3-quinolinecarboxylic acid;
(2S,3R)-6-bromo-1,2,3,4-tetrahydro-2-(trifluoromethyl)-3-quinolinecarboxylic acid;
(2S,3R)-1,2,3,4-tetrahydro-6-(trifluoromethoxy)-2-(trifluoromethyl)-3-quinolinecarboxylic acid;
(2S,3R)-6-(trifluoromethyl)-1,2,3,4-tetrahydro-2-(trifluoromethyl)-3-quinolinecarboxylic acid;
(2S,3R)-6-cyano-1,2,3,4-tetrahydro-2-(trifluoromethyl)-3-quinolinecarboxylic acid;
(2S,3R)-6-chloro-1,2,3,4-tetrahydro-1-methyl-2-(trifluoromethyl)-3-quinolinecarboxylic acid;
(2S,3R)-6-chloro-1,2,3,4-tetrahydro-2-(trifluoromethyl)-1-[[4-(trifluoromethyl)phenyl]methyl]-3-quinolinecarboxylic acid;
(2S,3R)-6-chloro-1-[(4-chlorophenyl)methyl]-1,2,3,4-tetrahydro-2-(trifluoromethyl)-3-quinolinecarboxylic acid;
(2S,3R)-6-chloro-1,2,3,4-tetrahydro-2-(trifluoromethyl)-1-[[4-(methoxy)phenyl]methyl]-3-quinolinecarboxylic acid;
(2S,3R)-6-chloro-1-[(4-cyanophenyl)methyl]-1,2,3,4-tetrahydro-2-(trifluoromethyl)-3-quinolinecarboxylic acid;
(2S,3R)-6-chloro-1,2,3,4-tetrahydro-1-[(4-nitrophenyl)methyl]-2-(trifluoromethyl)-3-quinolinecarboxylic acid;
(2S,3R)-6-chloro-1,2,3,4-tetrahydro-1-ethyl-2-(trifluoromethyl)-3-quinolinecarboxylic acid;
(2S,3R)-6-chloro-2-(triflouromethyl)-1,2,3,4-tetrahydro[1,8]napthyridine-3-carboxylic acid;
(2S,3R)-3,4-dihydro-2-trifluoromethyl-2H-naphtho[1,2-b]pyran-3-carboxylic acid;
(2S,3R)-3,4-dihydro-2-trifluoromethyl-3H-naptho[2,1-b]pyran-3-carboxylic acid;
(2S,3R)-3,4-dihydro-2-trifluoromethyl-2H-naphtho[2,3-b]pyran-3-carboxylic acid; and
(2S,3R)-3,4-dihydro-5-(hydroxymethyl)-8-methyl-2-(trifluoromethyl)-2H-pyrano[2,3-c]pyridine-3-carboxylic acid.

The term "hydrido" denotes a single hydrogen atom (H). This hydrido radical may be attached, for example, to an oxygen atom to form a hydroxyl radical or two hydrido radicals may be attached to a carbon atom to form a methylene (—CH$_2$—) radical. Where the term "alkyl " is used, either alone or within other terms such as "haloalkyl" and "alkylsulfonyl", it embraces linear or branched radicals having one to about twelve carbon atoms or, preferably, one to about eight carbon atoms. More preferred alkyl radicals are "lower alkyl" radicals having one to about six carbon atoms. Examples of such radicals include methyl, ethyl, n-propyl, isopropyl, n-butyl, isobutyl, sec-butyl, tert-butyl, pentyl, iso-amyl, hexyl and the like. Even more preferred are lower alkyl radicals having one to four carbon atoms. The term "alkenyl" embraces linear or branched radicals having at least one carbon-carbon double bond of two to about twelve carbon atoms or, preferably, two to about eight carbon atoms. More preferred alkenyl radicals are "lower alkenyl" radicals having two to about six carbon atoms. Examples of alkenyl radicals include ethenyl, propenyl, allyl, propenyl, butenyl and 4-methylbutenyl. The term "alkynyl" denotes linear or branched radicals having two to about twelve carbon atoms or, preferably, two to about eight carbon atoms. More preferred alkynyl radicals are "lower alkynyl" radicals having two to about six carbon atoms. Most preferred are lower alkynyl radicals having two to about four carbon atoms. Examples of such radicals include propargyl, butynyl, and the like. The alkenyl and alkynyl radicals may be substituted with halo atoms to form "haloalkynyl" and "haloalkenyl" radicals. The terms "alkenyl" and "lower alkenyl", embrace radicals having "cis" and "trans" orientations, or alternatively, "E" and "Z" orientations. The term "halo" means halogens such as fluorine, chlorine, bromine or iodine atoms. The term "haloalkyl" embraces radicals wherein any one or more of the alkyl carbon atoms is substituted with halo as defined above. Specifically embraced are monohaloalkyl, dihaloalkyl and polyhaloalkyl radicals. A monohaloalkyl radical, for one example, may have either an iodo, bromo, chloro or fluoro atom within the radical. Dihalo and polyhaloalkyl radicals may have two or more of the same halo atoms or a combination of different halo radicals. "Lower haloalkyl" embraces radicals having 1–6 carbon atoms. Examples of haloalkyl radicals include fluoromethyl, difluoromethyl, trifluoromethyl, chloromethyl, dichloromethyl, trichloromethyl, pentafluoroethyl, heptafluoropropyl, difluorochloromethyl, dichlorofluoromethyl, difluoroethyl, difluoropropyl, dichloroethyl and dichloropropyl. "Perfluoroalkyl" means alkyl radicals having all hydrogen atoms replaced with fluoro atoms. Examples include trifluoromethyl and pentafluoroethyl. The term "hydroxyalkyl" embraces linear or branched alkyl radicals having one to about ten carbon atoms any one of which may be substituted with one or more hydroxyl radicals. More preferred hydroxyalkyl radicals are "lower hydroxyalkyl" radicals having one to six carbon atoms and one or more hydroxyl radicals. Examples of such radicals include hydroxymethyl, hydroxyethyl, hydroxypropyl, hydroxybutyl and hydroxyhexyl. Even more preferred are lower hydroxyalkyl radicals having one to three carbon atoms. The term "cyanoalkyl" embraces linear or branched alkyl radicals having one to about ten carbon atoms any one of which may be substituted with one cyano radicals. More preferred cyanoalkyl radicals are "lower cyanoalkyl" radicals having one to six carbon atoms and one cyano radical. Even more preferred are lower cyanoalkyl radicals having one to three carbon atoms. Examples of such radicals include cyanomethyl. The term "alkoxy" embraces linear or branched oxy-containing radicals each having alkyl portions of one to about ten carbon atoms. More preferred alkoxy radicals are "lower alkoxy" radicals having one to six carbon atoms. Examples of such radicals include methoxy, ethoxy, propoxy, butoxy and tert-butoxy. Even more preferred are lower alkoxy radicals having one to three carbon atoms. The "alkoxy" radicals may be further substituted with one or more halo atoms, such as fluoro, chloro or bromo, to provide "haloalkoxy" radicals. Even more preferred are lower haloalkoxy radicals having one to three carbon atoms. Examples of such radicals include fluoromethoxy, chloromethoxy, trifluoromethoxy, trifluoroethoxy, fluoroethoxy and fluoropropoxy. The term "aryl", alone or in combination, means a carbocyclic aromatic system containing one or two rings wherein such rings may be attached together in a pendent manner or may be fused. The term "aryl" embraces aromatic radicals such as phenyl, naphthyl, tetrahydronaphthyl, indane and biphenyl. More preferred aryl is phenyl. Said "aryl" group may have 1 to 3 substituents such as lower alkyl, hydroxy, halo, lower haloalkyl, nitro, cyano, lower alkoxy and lower alkylamino. The term "heterocyclyl" embraces 5–10 membered saturated, partially saturated and unsaturated heteroatom-containing ring-shaped radicals, where the heteroatoms may be selected from nitrogen, sulfur and oxygen. Examples of saturated heterocyclic radicals include saturated 3 to 6-membered heteromonocylic group containing 1 to 4 nitrogen atoms [e.g. pyrrolidinyl, imidazolidinyl, piperidino, piperazinyl]; saturated 3 to 6-membered heteromonocyclic group containing 1 to 2 oxygen atoms and 1 to 3 nitrogen atoms [e.g. morpholinyl]; saturated 3 to 6-membered heteromonocyclic group containing 1 to 2 sulfur atoms and 1 to 3 nitrogen atoms [e.g., thiazolidinyl]. Examples of partially saturated heterocyclyl radicals include dihydrothiophene, dihydropyran, dihydrofuran and dihydrothiazole. Examples of unsaturated heterocyclic radicals, also termed "heteroaryl" radicals, include unsaturated 5 to 6 membered heteromonocyclyl group containing 1 to 4 nitrogen atoms, for example, pyrrolyl, pyrrolinyl, imidazolyl, pyrazolyl, 2-pyridyl, 3-pyridyl, 4-pyridyl, pyrimidyl, pyrazinyl, pyridazinyl, triazolyl [e.g., 4H-1,2,4-triazolyl, 1H-1,2,3-triazolyl, 2H-1,2,3-triazolyl]; unsaturated condensed heterocyclic group containing 1 to 5 nitrogen atoms, for example, indolyl, isoindolyl, indolizinyl, benzimidazolyl, quinolyl, isoquinolyl, indazolyl, benzotriazolyl, tetrazolopyridazinyl [e.g., tetrazolo [1,5-b]pyridazinyl]; unsaturated 3 to 6-membered heteromonocyclic group containing an oxygen atom, for example, pyranyl, 2-furyl, 3-furyl, etc.; unsaturated 5 to 6-membered heteromonocyclic group containing a sulfur atom, for example, 2-thienyl, 3-thienyl, etc.; unsaturated 5- to 6-membered heteromonocyclic group containing 1 to 2 oxygen atoms and 1 to 3 nitrogen atoms, for example, oxazolyl, isoxazolyl, oxadiazolyl [e.g., 1,2,4-oxadiazolyl, 1,3,4-oxadiazolyl, 1,2,5-oxadiazolyl]; unsaturated condensed heterocyclic group containing 1 to 2 oxygen atoms and 1 to 3 nitrogen atoms [e.g. benzoxazolyl, benzoxadiazolyl]; unsaturated 5 to 6-membered heteromonocyclic group containing 1 to 2 sulfur atoms and 1 to 3 nitrogen atoms, for example, thiazolyl, thiadiazolyl [e.g., 1,2,4-thiadiazolyl, 1,3,4-thiadiazolyl, 1,2,5-thiadiazolyl]; unsaturated condensed heterocyclic group containing 1 to 2 sulfur atoms and 1 to 3 nitrogen atoms [e.g., benzothiazolyl, benzothiadiazolyl] and the like. The term also embraces 9–10 membered radicals where heterocyclic radicals are fused with aryl radicals. Examples of such fused bicyclic radicals include benzofuran, quinolyl, benzothiophene, and the like. Said "heterocyclyl" group may have 1 to 3 substituents such as lower alkyl, hydroxy, oxo, amino and lower alkylamino. Preferred heterocyclic radicals include five to ten membered fused or unfused radicals. More preferred examples of heteroaryl radicals include benzofuryl, 2,3-dihydrobenzofuryl, benzothienyl, indolyl, dihydroindolyl, chromanyl, benzopyran, thiochromanyl, benzothiopyran, benzodioxolyl, benzodioxanyl, pyridyl, thienyl, thiazolyl, oxazolyl, furyl, and pyrazinyl. Even more preferred heteroaryl radicals are 5- or 6-membered heteroaryl, containing one or two heteroatoms selected from sulfur nitrogen and oxygen, selected from thienyl, furanyl, pyrrolyl, thiazolyl, oxazolyl, imidazolyl, pyrazolyl, isoxazolyl, isothiazolyl, pyridyl, piperidinyl and pyrazinyl. The term "sulfonyl", whether used alone or linked to other terms such as alkylsulfonyl, denotes respectively divalent radicals $-SO_2-$. "Alkylsulfonyl" embraces alkyl radicals attached to a sulfonyl radical, where alkyl is defined as above. More preferred alkylsulfonyl radicals are "lower alkylsulfonyl" radicals having one to six carbon atoms. Even more preferred are lower alkylsulfonyl radicals having one to three carbon atoms. Examples of such lower alkylsulfonyl radicals include methylsulfonyl, ethylsulfonyl and propylsulfonyl. "Haloalkylsulfonyl" embraces haloalkyl radicals attached to a sulfonyl radical, where haloalkyl is defined as above. More preferred haloalkylsulfonyl radicals are "lower haloalkylsulfonyl" radicals having one to six carbon atoms. Even more preferred are lower haloalkylsulfonyl radicals having one to three carbon atoms. Examples of such lower haloalkylsulfonyl radicals include trifluoromethylsulfonyl. The term "arylalkylsulfonyl" embraces aryl radicals as defined above, attached to an alkylsulfonyl radical. Examples of such radicals include benzylsulfonyl and phenylethylsulfonyl. The term "heterocyclylsulfonyl" embraces heterocyclyl radicals as defined above, attached to a sulfonyl radical. More preferred heterocyclylsulfonyl radicals contain 5–7 membered heterocyclyl radicals containing one or two heteroatoms. Examples of such radicals include tetrahydropyrrolylsulfonyl morpholinylsulfonyl and azepinylsulfonyl. The terms "sulfamyl," "aminosulfonyl" and "sulfonamidyl, " whether alone or used with terms such as "N-alkylaminosulfonyl", "N-arylaminosulfonyl", "N,N-dialkylaminosulfonyl" and "N-alkyl-N-arylaminosulfonyl", denotes a sulfonyl radical substituted with an amine radical, forming a sulfonamide ($-SO_2NH_2$). The term "alkylaminosulfonyl" includes "N-alkylaminosulfonyl" and "N,N-dialkylaminosulfonyl" where sulfamyl radicals are substituted, respectively, with one alkyl radical, or two alkyl radicals. More preferred alkylaminosulfonyl radicals are "lower alkylaminosulfonyl" radicals having one to six carbon atoms. Even more preferred are lower alkylaminosulfonyl radicals having one to three carbon atoms. Examples of such lower alkylaminosulfonyl radicals include N-methylaminosulfonyl, N-ethylaminosulfonyl and N-methyl-N-ethylaminosulfonyl. The terms "N-arylaminosulfonyl" and "N-alkyl-N-arylaminosulfonyl" denote sulfamyl radicals substituted, respectively, with one aryl radical, or one alkyl and one aryl radical. More preferred N-alkyl-N-arylaminosulfonyl radicals are "lower N-alkyl-N-arylsulfonyl" radicals having alkyl radicals of one to six carbon atoms. Even more preferred are lower N-alkyl-N-arylaminosulfonyl radicals having one to three carbon atoms. Examples of such lower N-alkyl-N-arylaminosulfonyl radicals include N-methyl-N-phenylaminosulfonyl and N-ethyl-N-phenylaminosulfonyl. Examples of such N-aryl-aminosulfonyl radicals include N-phenylaminosulfonyl. The term "arylalkylaminosulfonyl" embraces aralkyl radicals as described above, attached to an aminosulfonyl radical. More preferred are lower arylalkylaminosulfonyl radicals having one to three carbon atoms. The term "heterocyclylaminosulfonyl" embraces heterocyclyl radicals as described above, attached to an aminosulfonyl radical. The term "heteroarylalkylaminosulfonyl" embraces heteroarylalkyl radicals as described above, attached to an aminosulfonyl radical. The terms "N-heteroarylaminosulfonyl" and "N-alkyl-N-heteroarylaminosulfonyl" denote sulfamyl radicals substituted, respectively, with one heteroaryl radical, or one alkyl and one heteroaryl radical. More preferred N-alkyl-N-heteroarylaminosulfonyl radicals are "lower N-alkyl-N-heteroarylsulfonyl" radicals having alkyl radicals of one to six carbon atoms. Even more preferred are lower N-alkyl-N-heteroarylaminosulfonyl radicals having one to three carbon atoms. The terms "carboxy" or "carboxyl", whether used alone or with other terms, such as "carboxyalkyl", denotes —CO$_2$H. The term "carboxyalkyl" embraces radicals having a carboxy radical as defined above, attached to an alkyl radical. The term "carbonyl", whether used alone or with other terms, such as "alkylcarbonyl", denotes —(C=O)—. The term "alkylcarbonyl" embraces radicals having a carbonyl radical substituted with an alkyl radical. More preferred alkylcarbonyl radicals are "lower alkylcarbonyl" radicals having one to six carbon atoms. Even more preferred are lower alkylcarbonyl radicals having one to three carbon atoms. Examples of such radicals include methylcarbonyl and ethylcarbonyl. The term "haloalkylcarbonyl" embraces radicals having a carbonyl radical substituted with an haloalkyl radical. More preferred haloalkylcarbonyl radicals are "lower haloalkylcarbonyl" radicals having one to six carbon atoms. Even more preferred are lower haloalkylcarbonyl radicals having one to three carbon atoms. Examples of such radicals include trifluoromethylcarbonyl. The term "arylcarbonyl" embraces radicals having a carbonyl radical substituted with an aryl radical. More preferred arylcarbonyl radicals include phenylcarbonyl. The term "heteroarylcarbonyl" embraces radicals having a carbonyl radical substituted with a heteroaryl radical. Even more preferred are 5- or 6-membered heteroarylcarbonyl radicals. The term "arylalkylcarbonyl" embraces radicals having a carbonyl radical substituted with an arylalkyl radical. More preferred radicals are phenyl-$C_1$–$C_3$-alkylcarbonyl, including benzylcarbonyl. The term "heteroarylalkylcarbonyl" embraces radicals having a carbonyl radical substituted with a heteroarylalkyl radical. Even more preferred are lower heteroarylalkylcarbonyl radicals having 5–6-membered heteroaryl radicals attached to alkyl portions having one to three carbon atoms. The term "alkoxycarbonyl" means a radical containing an alkoxy radical, as defined above, attached via an oxygen atom to a carbonyl radical. Preferably, "lower alkoxycarbonyl" embraces alkoxy radicals having one to six carbon atoms. Examples of such "lower alkoxycarbonyl" ester radicals include substituted or unsubstituted methoxycarbonyl, ethoxycarbonyl, propoxycarbonyl, butoxycarbonyl and hexyloxycarbonyl Even more preferred are lower alkoxycarbonyl radicals having alkoxy portions of one to three carbon atoms. The term "aminocarbonyl" when used by itself or with other terms such as "aminocarbonylalkyl", "N-alkylaminocarbonyl", "N-arylaminocarbonyl", "N,N-dialkylaminocarbonyl", "N-alkyl-N-arylaminocarbonyl", "N-alkyl-N-hydroxyaminocarbonyl" and "N-alkyl-N-hydroxyaminocarbonylalkyl", denotes an amide group of the formula —C(=O)NH$_2$. The terms "N-alkylaminocarbonyl" and "N,N-dialkylaminocarbonyl" denote aminocarbonyl radicals which have been substituted with one alkyl radical and with two alkyl radicals, respectively. More preferred are "lower alkylaminocarbonyl" having lower alkyl radicals as described above attached to an aminocarbonyl radical. The terms "N-arylaminocarbonyl" and "N-alkyl-N-arylaminocarbonyl" denote aminocarbonyl radicals substituted, respectively, with one aryl radical, or one alkyl and one aryl radical. The term "alkylsulfonylaminocarbonyl" denotes aminocarbonyl radicals substituted with one alkylsulfonyl radical. The term "cycloalkyl" embraces saturated carbocyclic radicals having three to about eight carbon atoms. More prefferred cycloalkyl radicals are "lower cycloalkyl" radicals of four to seven carbon atoms. Examples include cyclobutyl, cyclopentenyl and cyclohexyl. The term "N-cycloalkylaminocarbonyl" denoted aminocarbonyl radicals which have been substituted with at least one cycloalkyl radical. More preferred are "lower cycloalkylaminocarbonyl" having lower cycloalkyl radicals of three to seven carbon atoms, attached to an aminocarbonyl radical. The term "aminoalkyl" embraces alkyl radicals substituted with one or more amino radicals. The term "alkylaminoalkyl" embraces aminoalkyl radicals having the amino nitrogen atom substituted with an alkyl radical. Even more preferred are lower alkylaminoalkyl radicals having one to three carbon atoms. The term "heterocyclylalkyl" embraces heterocyclic-substituted alkyl radicals. More preferred heterocyclylalkyl radicals are "5- or 6-membered heteroarylalkyl" radicals having alkyl portions of one to six carbon atoms and a 5- or 6-membered heteroaryl radical. Even more preferred are lower heteroarylalkyl radicals having alkyl portions of one to three carbon atoms. Examples include such radicals as pyridylmethyl and thienylmethyl. The term "aralkyl" embraces aryl-substituted alkyl radicals. Preferable aralkyl radicals are "lower aralkyl" radicals having aryl radicals attached to alkyl radicals having one to six carbon atoms. Even more preferred are lower aralkyl radicals phenyl attached to alkyl portions having one to three carbon atoms. Examples of such radicals include benzyl, diphenylmethyl and phenylethyl. The terms benzyl and phenylmethyl are interchangeable. The aryl in said aralkyl may be additionally substituted with halo, lower alkyl, lower alkoxy, lower halkoalkyl and lower haloalkoxy. The term "arylalkenyl" embraces aryl-substituted alkenyl radicals Preferable arylalkenyl radicals are "lower arylalkenyl" radicals having aryl radicals attached to alkenyl radicals having two to six carbon atoms. Examples of such radicals include phenylethenyl. The aryl in said arylalkenyl may be additionally substituted such as with halo, lower alkyl, lower alkoxy, lower halkoalkyl and lower haloalkoxy The term "arylalkynyl" embraces aryl-substituted alkynyl radicals. Preferable arylalkynyl radicals are "lower arylalkynyl" radicals having aryl radicals attached to alkynyl radicals having two to six carbon atoms. Examples of such radicals include phenylethynyl. The aryl in said aralkyl may be additionally substituted such as with halo, lower alkyl, lower alkoxy, lower halkoalkyl and lower haloalkoxy. The term "alkylthio" embraces radicals containing a linear or branched alkyl radical, of one to ten carbon atoms, attached to a divalent sulfur atom. Even more preferred are lower alkylthio radicals having one to three carbon atoms. An example of "alkylthio" is methylthio, (CH$_3$—S—). The term "haloalkylthio" embraces radicals containing a haloalkyl radical, of one to ten carbon atoms, attached to a divalent sulfur atom. Even more preferred are lower haloalkylthio radicals having one to three carbon atoms. An example of "haloalkylthio" is trifluoromethylthio. The term "alkylsulfinyl" embraces radicals containing a linear or branched alkyl radical, of one to ten carbon atoms, attached to a divalent —S(=O)— atom. More preferred are lower alkylsulfinyl radicals having one to three carbon atoms. The term "arylsulfinyl" embraces radicals containing an aryl radical, attached to a divalent —S(=O)— atom. Even more preferred are optionally substituted phenylsulfinyl radicals. The term "haloalkylsulfinyl" embraces radicals containing a haloalkyl radical, of one to ten carbon atoms, attached to a divalent —S(=O)— atom. Even more preferred are lower haloalkylsulfinyl radicals having one to three carbon atoms. The terms "N-alkylamino" and "N,N-dialkylamino" denote amino groups which have been substituted with one or two alkyl radicals. More preferred alkylamino radicals are "lower alkylamino" radicals having one or two alkyl radicals of one to six carbon atoms, attached to a nitrogen atom. Even more preferred are lower alkylamino radicals having one to three carbon atoms. Suitable "alkylamino" may be mono or dialkylamino such as N-methylamino, N-ethylamino, N,N-dimethylamino, N,N-diethylamino or the like. The term "arylamino" denotes amino groups which have been substituted with one or two aryl radicals, such as N-phenylamino. The "arylamino" radicals may be further substituted on the aryl ring portion of the radical. The term "heteroarylamino" denotes amino groups which have been substituted with one or two heteroaryl radicals, such as N-thienylamino. The "heteroarylamino" radicals may be further substituted on the heteroaryl ring portion of the radical. The term "aralkylamino" denotes amino groups which have been substituted with one or two aralkyl radicals. More preferred are phenyl-$C_1$–$C_3$-alkylamino radicals, such as N-benzylamino. The "aralkylamino" radicals may be further substituted on the aryl ring portion of the radical. The terms "N-alkyl-N-arylamino" and "N-aralkyl-N-alkylamino" denote amino groups which have been substituted with one aralkyl and one alkyl radical, or one aryl and one alkyl radical, respectively, to an amino group. The term "heteroarylalkylamino" denotes amino groups which have been substituted with one or two heteroarylalkyl radicals. The "heteroarylalkylamino" radicals may be further substituted on the heteroaryl ring portion of the radical. The terms "N-alkyl-N-heteroarylamino" and "N-heteroarylalkyl-N-alkylamino" denote amino groups which have been substituted with one heteroarylalkyl and one alkyl radical, or one heteroaryl and one alkyl radical, respectively, to an amino group. The term "arylthio" embraces aryl radicals of six to ten carbon atoms, attached to a divalent sulfur atom. An example of "arylthio" is phenylthio. The term "aralkylthio" embraces aralkyl radicals as described above, attached to a divalent sulfur atom. More preferred are phenyl-$C_1$–$C_3$-alkylthio radicals. An example of "aralkylthio" is benzylthio. The term "aralkylsulfonyl" embraces aralkyl radicals as described above, attached to a divalent sulfonyl radical. More preferred are phenyl-$C_1$–$C_3$-alkylsulfonyl radicals. The term "aryloxy" embraces optionally substituted aryl radicals, as defined above, attached to an oxygen atom. Examples of such radicals include phenoxy. The term "heteroaryloxy" embraces optionally substituted heteroaryl radicals, as defined above, attached to an oxygen atom. The term "aralkoxy" embraces oxy-containing aralkyl radicals attached through an oxygen atom to other radicals. More preferred aralkoxy radicals are "lower aralkoxy" radicals having optionally substituted phenyl radicals attached to lower alkoxy radical as described above. Examples of such radicals include benzyloxy. The term "alkoxyalkyl" embraces alkoxy radicals attached through an oxygen atom to alkyl radicals. More preferred alkoxyalkyl radicals are "lower alkoxyalkyl" radicals having lower alkoxy radicals attached to lower alkoxy radical as described above. The term "arylalkoxyalkyl" embraces arylalkoxy radicals attached through an oxygen atom to alkyl radicals. More preferred arylalkoxyalkyl radicals are "lower arylalkoxyalkyl" radicals having optionally substituted aryl radicals attached to lower alkoxyalkyl radical as described above. The term "heteroarylalkoxy" embraces oxy-containing heteroarylalkyl radicals attached through an oxygen atom to alkyl radicals. More preferred heteroarylalkoxy radicals are "lower heteroarylalkoxy" radicals having optionally substituted heteroaryl radicals attached to lower alkoxy radical as described above.

The present invention comprises a pharmaceutical composition comprising a therapeutically-effective amount of a compound of Formula I–IV in association with at least one pharmaceutically-acceptable carrier, adjuvant or diluent.

The present invention also comprises a method of treating cyclooxygenase-2 mediated disorders, such as inflammation, in a subject, the method comprising treating the subject having or susceptible to such disorder with a therapeutically-effective amount of a compound of Formula I–IV.

Also included in the family of compounds of Formula I–IV are the stereoisomers thereof. Compounds of the present invention can possess one or more asymmetric carbon atoms and are thus capable of existing in the form of optical isomers as well as in the form of racemic or non-racemic mixtures thereof. Accordingly, some of the compounds of this invention may be present in racemic mixtures which are also included in this invention. The optical isomers can be obtained by resolution of the racemic mixtures according to conventional processes, for example by formation of diastereoisomeric salts by treatment with an optically active base and then separation of the mixture of diastereoisomers by crystallization, followed by liberation of the optically active bases from these salts. Examples of appropriate bases are brucine, strychnine, dehydroabietylamine, quinine, cinchonidine, ephedrine, α-methylbenzylamine, amphetamine, deoxyphedrine, chloramphenicol intermediate, 2-amino-1-butanol, and 1-(1-napthyl)ethylamine. A different process for separation of optical isomers involves the use of a chiral chromatography column optimally chosen to maximize the separation of the enantiomers. Still another available method involves synthesis of covalent diastereoisomeric molecules. The synthesized diastereoisomers can be separated by conventional means such as chromatography, distillation, crystallization or sublimation, and then hydrolyzed to deliver the enantiomerically pure compound. The optically active compounds of Formula I can likewise be obtained by utilizing optically active starting materials. These isomers may be in the form of a free acid, a free base, an ester or a salt. Additional methods for resolving optical isomers, known to those skilled in the art may be used, for example, those discussed by J. Jaques et al in *Enantiomers, Racemates, and Resolutions*, John Wiley and Sons, New York (1981).

Also included in the family of compounds of Formula I–IV are the protected acids thereof, such as the esters, hydroxyamino derivatives, amides and sulfonamides, to form the active compounds in vivo. Thus primary and secondary amines can be reacted with the dihydrochromene-3-carboxylic acids of Formula I–V to form amides which can be useful as prodrugs to form the active compounds in vivo. Preferred amines heterocyclicamines, including optionally substituted aminothiazoles, optionally substituted amino-isoxazoles, and optionally substituted aminopyridines; aniline derivatives; sulfonamides; aminocarboxylic acids; and the like. Additionally, 1-acyldihydroquinolines can behave as prodrugs for the 1H-dihydroquinolines. The esters, hydroxyamino derivatives and sulfonamides can be prepared from the acids by methods known to one skilled in the art.

Also included in the family of compounds of Formula I–V are the pharmaceutically-acceptable salts thereof. The term "pharmaceutically-acceptable salts" embraces salts commonly used to form alkali metal salts and to form addition salts of free acids or free bases. The nature of the salt is not critical, provided that it is pharmaceutically-acceptable. Suitable pharmaceutically-acceptable acid addition salts of compounds of Formula I–V may be prepared from an inorganic acid or from an organic acid. Examples of such inorganic acids are hydrochloric, hydrobromic, hydroiodic, nitric, carbonic, sulfuric and phosphoric acid. Appropriate organic acids may be selected from aliphatic, cycloaliphatic, aromatic, araliphatic, heterocyclic, carboxylic and sulfonic classes of organic acids, example of which are formic, acetic, propionic, succinic, glycolic, gluconic, lactic, malic, tartaric, citric, ascorbic, glucuronic, maleic, fumaric, pyruvic, aspartic, glutamic, benzoic, anthranilic, mesylic, salicylic, 4-hydroxybenzoic, phenylacetic, mandelic, embonic (pamoic), methanesulfonic, ethanesulfonic, benzenesulfonic, pantothenic, 2-hydroxyethanesulfonic, toluenesulfonic, sulfanilic, cyclohexylaminosulfonic, stearic, algenic, β-hydroxybutyric, galactaric and galacturonic acid. Suitable pharmaceutically-acceptable base addition salts of compounds of Formula I–V include metallic salts, such as salts made from aluminum, calcium, lithium, magnesium, potassium, sodium and zinc, or salts made from organic bases including primary, secondary and tertiary amines, substituted amines including cyclic amines, such as caffeine, arginine, choline, diethylamine, 2-dimethylaminoethanol, 2-diethylaminoethanol, ethanolamine, N-ethylpiperidine, histidine, glucamine, glucosamine, isopropylamine, lysine, morpholine, N-ethyl morpholine, piperazine, piperidine, procaine, purines, theobromine, triethylamine, trimethylamine, and tripropylamine. All of these salts may be prepared by conventional means from the corresponding compound of the invention by reacting, for example, the appropriate acid or base with the compound of Formula I–V.

General Synthetic Procedures

The compounds of the invention can be synthesized according to the following procedures of Schemes 1–17, wherein the $R^1$–$R^6$ substituents are as defined for Formulas I–V, above, except where further noted.

Synthetic Scheme 1 illustrates the general method for the preparation of a wide variety of substituted 2H-1-benzopyran derivatives 3 and 4. In step 1, a representative ortho-hydroxybenzaldehyde (salicylaldehyde) derivative 1 is condensed with an acrylate derivative 2 in the presence of base, such as potassium carbonate in a solvent such as dimethylformamide, to afford the desired 2H-1-benzopyran ester 3. An alternative base-solvent combination for this condensation includes an organic base such as triethylamine and a solvent such as dimethyl sulfoxide. In step 2 the ester is hydrolyzed to the corresponding acid, such as by treatment with aqueous base (sodium hydroxide) in a suitable solvent such as ethanol to afford after acidification the substituted 2H-1-benzopyran-3-carboxylic acid 4.

SCHEME 2

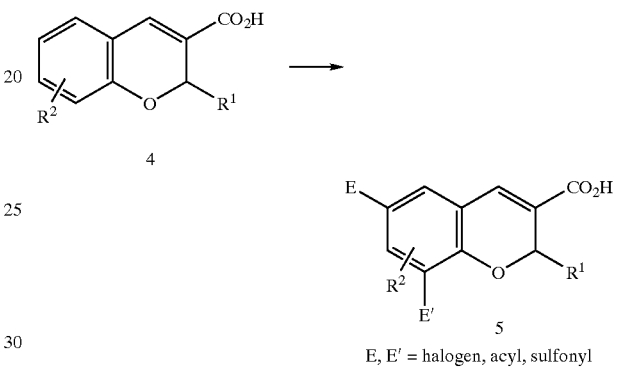

E, E' = halogen, acyl, sulfonyl

Synthetic Scheme 2 shows the general method for functionalizing selected 2H-1-benzopyrans. Treatment of the 2H-1-benzopyran carboxylic acid 4 or ester 3 with an electrophilic agent makes a 6-substituted 2H-1-benzopyran 5. A wide variety of electrophillic agents react selectively with 2H-1-benzopyrans 4 in the 6-position to provide new analogs in high yield. Electrophilic reagents such as halogen (chlorine or bromine) give the 6-halo derivatives. Chlorosulfonic acid reacts to afford the 6-position sulfonyl chloride that can further be converted to a sulfonamide or sulfone. Friedel-Crafts acylation of 4 provides 6-acylated 2H-1-benzopyrans in good to excellent yield. A number of other electrophiles can be used to selectively react with these 2H-1-benzopyrans in a similar manner. A 6-position substituted 2H-1-benzopyran can react with an electrophilic reagent at the 8-position using similar chemistries to that described for electrophilic substitution of the 6-position. This yields an 2H-1-benzopyran which is substituted at both the 6 and 8 positions.

SCHEME 1

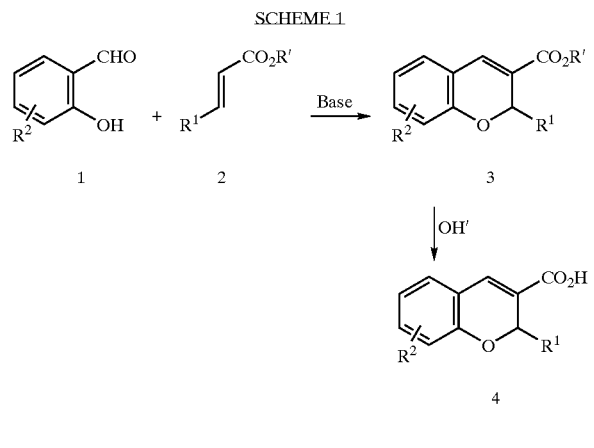

SCHEME 3

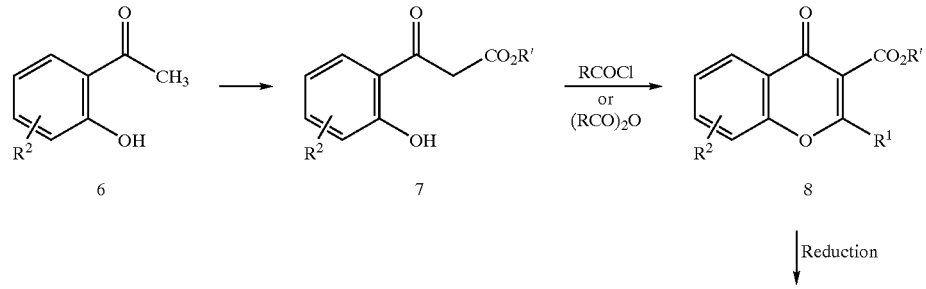

Reduction

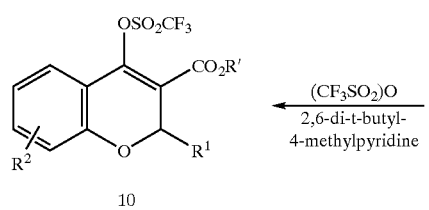

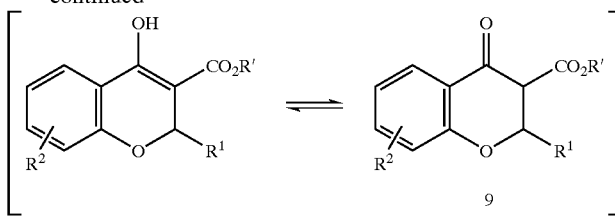

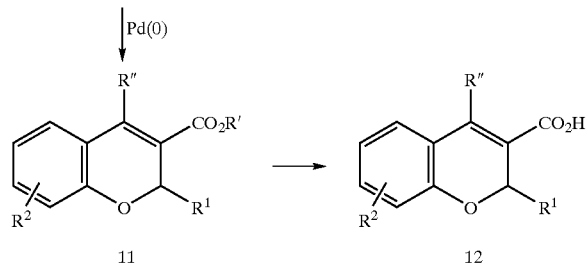

Synthetic Scheme 3 illustrates a second general synthesis of substituted 2H-1-benzopyran-3-carboxylic acids which allows substitution at position 4 of the 2H-1-benzopyran. In this case a commercially or synthetically available subtituted ortho-hydroxy acetophenone 6 is treated with two or more equivalents of a strong base such as lithium bis(trimethylsilyl)amide in a solvent such as tetrahydrofuran (THF), followed by reaction with diethyl carbonate to afford the beta-keto ester 7. Ester 7 is condensed with an acid chloride or anhydride in the presence of a base such as potassium carbonate in a solvent such as toluene with heat to afford 4-oxo-4H-1-benzopyran 8. Reduction of the olefin can be accomplished by a variety of agents including sodium borohydride ($NaBH_4$) in solvent mixtures such as ethanol and tetrahydrofuran (THF), or by use of triethylsilane in a solvent such as trifluoroacetic acid, or by catalytic reduction using palladium on charcoal and hydrogen gas in a solvent such as ethanol to yield the new beta-keto ester 9 (two tautomeric structures shown). Acylation of the oxygen of the ketone enolate in the presence of a base such as 2,6-di-tert-butyl-4-methylpyridine, an acylating agent such as trifluoromethanesulfonic anhydride, and using a solvent such as methylene chloride yields the enol-triflate 10. Triflate 10 can be reduced with reagents such as tri-n-butyltin hydride, lithium chloride and a palladium (0) catalyst such as tetrakis(triphenylphosphine)palladium (0) in a solvent such as tetrahydrofuran to yield 2H-1-benzopyran ester 11 where R" is hydrogen. The ester 11 can be saponified with a base such as 2.5 N sodium hydroxide in a mixed solvent such as tetrahydrofuran-ethanol-water (7:2:1) to yield the desired substituted 2H-1-benzopyran-3-carboxylic acid.

To incorporate a carbon fragment R" one can treat triflate 10 with reagents known to undergo "cross-coupling" chemistries such a tributylethenyltin, lithium chloride and a palladium (0) catalyst such as tetrakis(triphenylphosphine) palladium (0) in a solvent such as tetrahydrofuran to yield 2H-1-benzopyran ester 11 where R" is a vinyl moiety. The ester 6 can be saponified with a base such as 2.5 N sodium hydroxide in a mixed solvent such as tetrahydrofuran-ethanol-water (7:2:1) to yield the desired 4-vinyl-2H-1-benzopyran-3-carboxylic acid (12, R"=—$CHCH_2$). Similarly triflate 10 can be converted under similar conditions using tri-n-butylphenyltin to 2H-1-benzopyran where $R^3$=phenyl and by hydrolysis of the ester converted to the carboxylic acid 12 where R"=phenyl. Using a similar strategy, substituents which be incorporated as substitutent R" can be substituted olefins, substituted aromatics, substuted heteroaryl, acetylenes and substituted acetylenes.

SCHEME 4

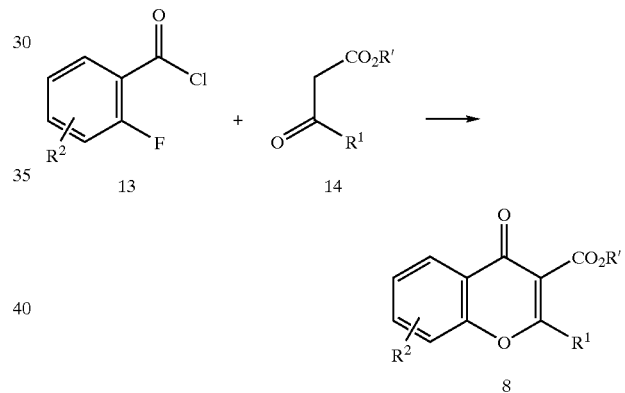

Synthetic Scheme 4 shows an alternative general procedure for the preparation of 4-oxo-4H-1-benzopyran 8. Treatment of an ortho-fluorobenzoyl chloride with an appropriately substituted beta-keto ester 14 with a base such as potassium carbonate in a solvent such as toluene provides 4-oxo-4H-1-benzopyran 8. 4-Oxo-4H-1-benzopyran 8 can be converted to 2H-1-benzopyran 12 as described in Scheme 3.

SCHEME 5

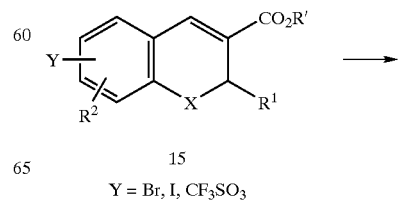

Y = Br, I, $CF_3SO_3$

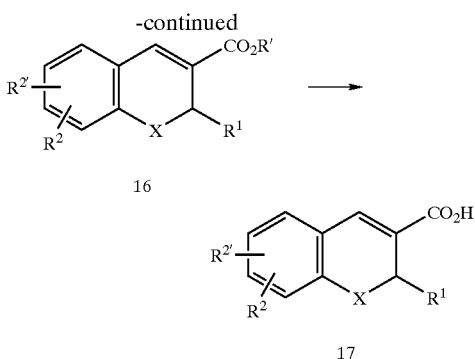

Synthetic Scheme 5 shows a general method for substitution of the aromatic ring of the 2H-1-benzopyran. This can be accomplished through organo-palladium mediated "cross-coupling" chemistries using a palladium (0) catalyst to couple benzopyran 15 at position Y, where Y is iodide, bromide or triflate, with an acetylene, olefin, nitrile, or aryl coupling agent. Substituted acetylenes as the coupling agent will provide the corresponding substituted acetylene. Substituted aryl moieties can be incorporated using arylboronic acids or esters; nitriles riles can be incorporated by use of zinc (II) cyanide. The resulting ester 16 can be converted to carboxylic acid 17 as described in Scheme 1.

Another approach to substitution of the aryl moiety of the benzopyran 15 is to convert Y, where Y is iodide or bromide, to a perfluoroalkyl moiety. Exemplary of this transformation is the conversion of 15 (Y=iodide) to 16 ($R^{2'}$= pentafluoroethyl) using a potassium pentafluoropropionate and copper (I) iodide in hexamethylphosphoramide (HMPA). The resulting ester 16 can be converted to carboxylic acid 15 as described in Scheme 1.

A similar method adds substitution of the aromatic ring in dihydroquinoline-3-carboxylates. This can be accomplished through organopalladium couplings with aryl iodides, bromides, or triflates and various coupling agents (R. F. Heck, Palladium Reagents in Organic Synthesis. Academic Press 1985). When using a suitable palladiumcatalyst such as tetrakis(triphenyl-phospine)palladium(0) in this reaction, coupling agents such as alkynes provide disubstituted alkynes, phenyl boronic acids afford biphenyl compounds, and cyanides produce arylcyano compounds. A number of other palladium catalysts and coupling reagents could be used to selectively react with appropriately substituted dihydroquinoline-3-carboxylates in a similar manner.

SCHEME 6

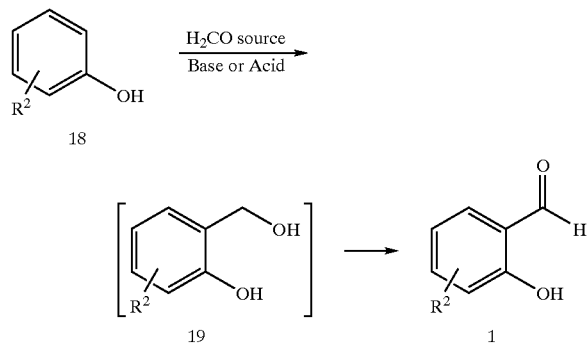

Synthetic Scheme 6 shows a general synthetic route for conversion of a commercially or synthetically available substituted phenol into a substituted salicylaldehyde. Several different methods which utilize formaldehyde or a chemically equivalent reagent are described in detail below.

Reaction of an appropriately substitutedphenol 18 in basic media with formaldehyde (or chemical equivalent) will yield the corresponding salicylaldehyde 1. The intermediate, ortho-hydroxymethylphenol 19, will under appropriate reaction conditions be oxidized to the salicylaldehyde 1 in situ. The reaction commonly employs ethyl magnesium bromide or magnesium methoxide (one equivalent) as the base, toluene as the solvent, paraformaldehyde (two or more equivalents) as the source of formaldehyde, and employs hexamethylphoramide (HMPA) or N,N,N',N'-tetramethylethylenediamine (TMEDA). (See: Casiraghi, G. et al., J. C. S. Perkin 1,1978, 318–321.)

Alternatively an appropriately substituted phenol 18 may react with formaldehyde under aqueous basic conditions to form the substituted ortho-hydroxybenzyl alcohol 19 (See: a) J. Leroy and C. Wakselman, J. Fluorine Chem., 40, 23–32 (1988). b) A. A. Moshfegh, et al., Helv. Chi. Acta., 65, 1229–1232 (1982)). Commonly used bases include aqueous potassium hydroxide or sodium hydroxide. Formalin (38% formaldehyde in water) is commonly employed as the source of formaldehyde. The resulting ortho-hydroxybenzyl alcohol 19 can be converted to the salicylaldehyde 1 by an oxidizing agent such as manganese (IV) dioxide in a solvent such as methylene chloride or chloroform (See: R-G. Xie, et al., Synthetic Commun. 24, 53–58 (1994)).

An appropriately substituted phenol 18 can be treated under acidic conditions with hexamethylenetetramine (HMTA) to prepare the salicylaldehyde 1 (Duff Reaction; See: Y. Suzuki, and H. Takahashi, Chem. Pharm. Bull., 31, 1751–1753 (1983)). This reaction commonly employs acids such as acetic acid, boric acid, methanesulfonic acid, or trifluoromethanesulfonic acid. The source of formaldehyde commonly used is hexamethylenetetramine.

SCHEME 7

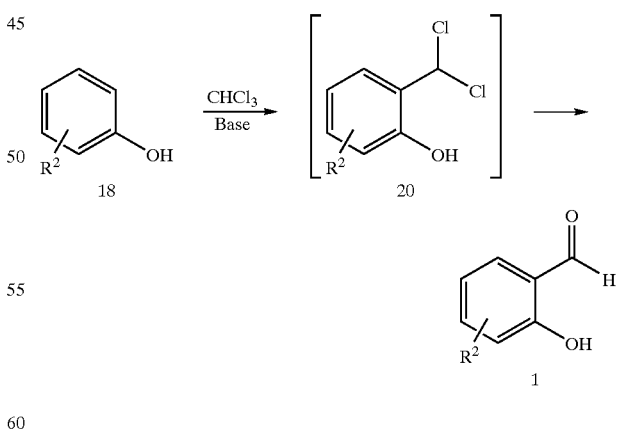

Synthetic Scheme 7 shows the Reimer-Tiemann reaction in which a commercially or synthetically available appropriately substituted phenol 18 will under basic conditions react with chloroform to yield a substituted salicylaldehyde 1 (See: Cragoe, E. J.; Schultz, E. M., U.S. Pat. No. 3,794, 734, 1974).

SCHEME 8

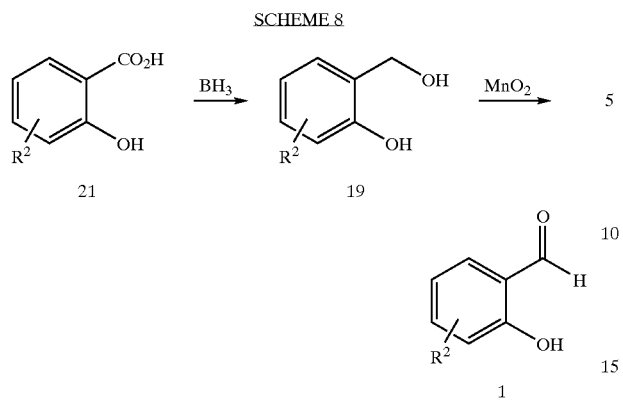

Synthetic Scheme 8 shows the conversion of a commercially or synthetically available appropriately substituted salicylic acid 21 to its respective salicylaldehyde 1 via an intermediate 2-hydroxybenzyl alcohol 19. Reduction of the salicylic acid 21 can be accomplished with a hydride reducing agent such as borane in a solvent such as tetrahydrofuran. Treatment of the intermediate 2-hydroxybenzyl alcohol 19 with an oxidizing agent such as manganese (IV) oxide in a solvent such as methylene chloride or chloroform provides salicylaldehyde 1.

SCHEME 9

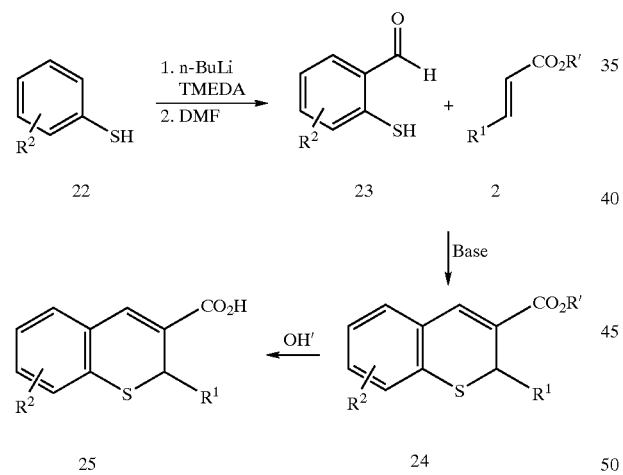

Synthetic Scheme 9 illustrates a general synthetic method for preparation of a wide variety of substituted 2-(trifluoromethyl)-2H-1-benzothiopyran-3-carboxylic acids (25). In step 1, an appropriately commercially or synthetically available substituted thiophenol 22 is ortho-metallated with a base such as n-butyllithium employing TMEDA (N,N,N',N'-tetramethylethylenediamine) followed by treatment with dimethylformamide to provide the 2-mercaptobenzaldehyde 23. Condensation of the 2-mercaptobenzaldehyde 23 with an acrylate 2 in the presence of base provides ester 24 which can be saponified in the presence of aqueous base to afford the substituted 2H-1-benzothiopyran-3-carboxylic acids 25.

SCHEME 10

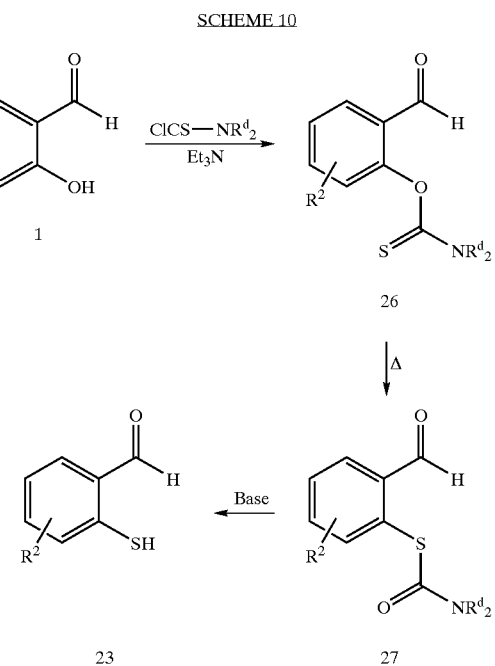

Synthetic Scheme 10 shows a method for preparing a substituted 2-mercaptobenzaldehyde from an appropriate commercially or synthetically available substituted salicylaldehyde. In step 1, the phenolic hydroxyl of salicylaldehyde 1 is converted to the corresponding O-aryl thiocarbamate 26 by acylation with an appropriately substituted thiocarbamoyl chloride such as N,N-dimethylthiocarbamoyl chloride in a solvent such as dimethylformamide using a base such as triethylamine. In Step 2, O-aryl thiocarbamate 26 rearranges to S-aryl thiocarbamate 27 when heated sufficiently such as to 200° C. using either no solvent or a solvent such as N,N-dimethylaniline (See: A. Levai, and P. Sebok, Synth. Commun., 22 1735–1750 (1992)). Hydrolysis of S-aryl thiocarbamate 27 with a base such as 2.5 N sodium hydroxide in a solvent mixture such as tetrahydrofuran and ethanol yields the substituted 2-mercaptobenzaldehyde 23 which can be converted to the substituted 2H-1-benzothiopyran-3-carboxylic acids 25 as described in Scheme 9.

SCHEME 11

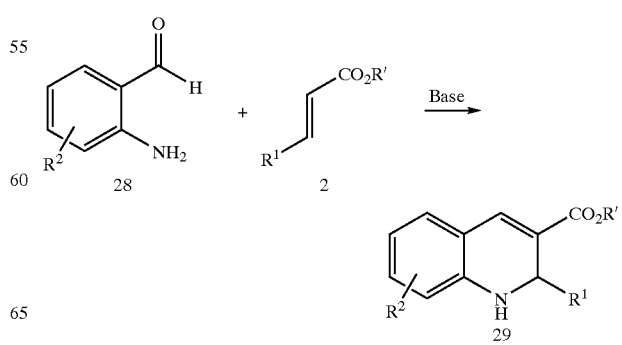

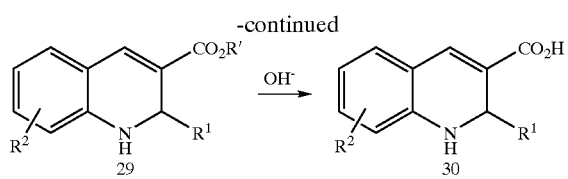

Synthetic Scheme 11 illustrates the general method for the preparation of a wide variety of dihydroquinoline-3-carboxylic acid derivatives 30. $R^2$ represents the aromatic substitution of commercially and synthetically available 2-aminobenzaldeydes 28. The 2-amino-benzaldehyde derivative 28, where $R^2$ represents various substitutions, is condensed with a acrylate derivative 2 in the presence of base such as potassium carbonate, triethylamine, or diazbicyclo[2.2.2]undec-7-ene in solvents such as dimethylformamide to afford the dihydroquinoline-3-carboxylate esters 29. The ester 29 can be saponified to the corresponding acid, such as by treatment with aqueous inorganic base such as 2.5 N sodium hydroxide in a suitable solvent such as ethanol to afford after acidification the desired dihydroquinoline-3-carboxylic acid 30.

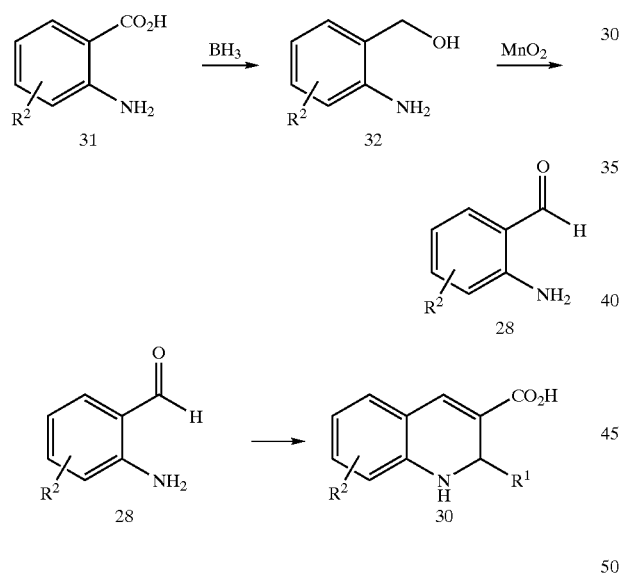

Synthetic Scheme 12 illustrates the preparation of dihydroquinoline-3-carboxylic acid 30 from 2-aminobenzoic acids 31. $R^2$ represents the aromatic substitution of commercially and synthetically available 2-aminobenzoic acids 31. Reduction of the representative 2-aminoberizoic acid 31 to the desired 2-aminobenzyl alcohol 32 was accomplished with a hydride reducing agent such as borane in a solvent such as tetrahydrofuran. Treatment of the desired 2-aminobenzyl alcohol 32 with an oxidizing agent such as manganese (IV) oxide in a solvent such as methylene chloride provides the representative 2-aminobenzaldehydes 28. (C. T. Alabaster, et al. *J. Med. Chem.* 31, 2048–2056 (1988)) The 2-aminobenzaldehydes were converted to the desired dihydroquinoline-3-carboxylic acid 30 as described in Scheme 11.

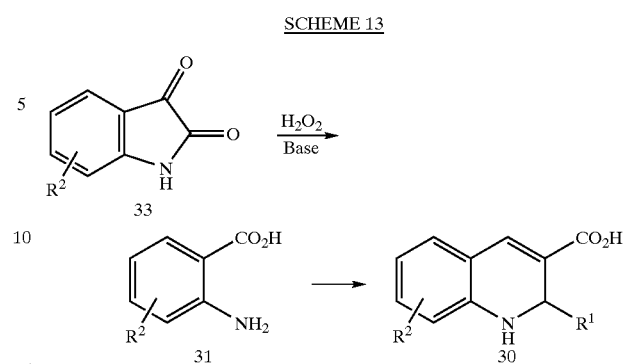

Synthetic Scheme 13 illustrates the general method for the preparation of a wide variety of dihydroquirioline-3-carboxylic acid derivatives 30 from isatins 33. $R^2$ represents the aromatic substitution of commercially and synthetically available isatins 33. A representative isatin 33 was treated with basic peroxide generated from hydrogen peroxide and a base such as sodium hydroxide to afford the desired representative 2-aminobenzoic acids 31. (M. S. Newman and M. W. Lougue, *J. Org. Chem.*, 36, 1398–1401 (1971)) The 2-aminobenzoic acids 31 are subsequently converted to the desired dihydroquinoline-3-carboxylic acid derivatives 30 as described in synthetic Scheme 12.

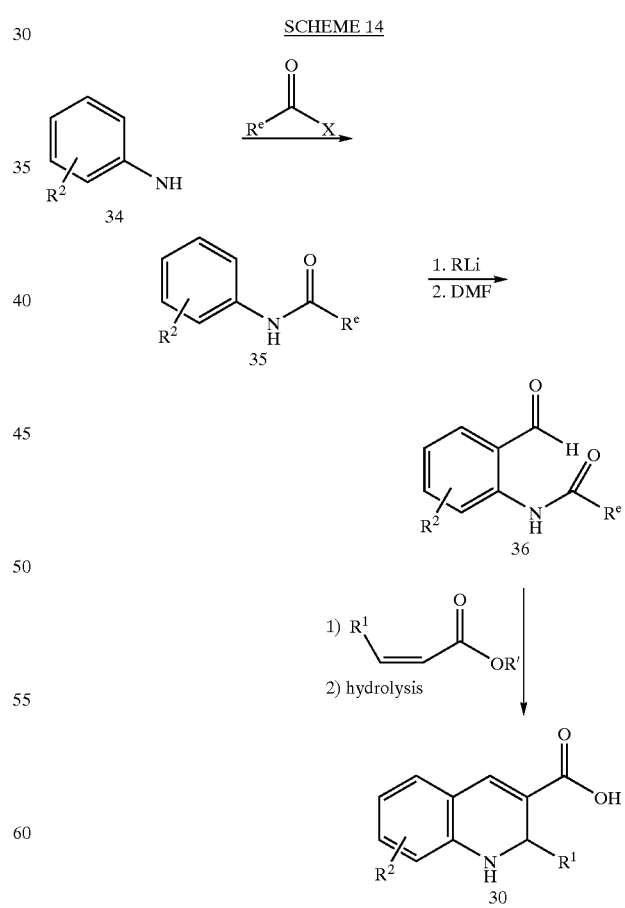

Synthetic Scheme 14 is another general method for the preparation of dihydroquinoline-3-carboxylic acid derivatives 30. In step 1, an appropriate commercially or synthetically available substituted aniline 34 can be treated with an acylating reagent such as pivaloyl chloride yielding an amide 35. The ortho-dianion of amide 35 is prepared by treating amide 35 with organo-lithium bases such as n-butyllithium or tert-butyllithium in tetrahydrofuran at low temperature. The dianion is quenched with dimethylformamide to afford the acylated-2-amino-benzaldehydes 36. (J. Turner, *J. Org. Chem.*, 48, 3401–3408 (1983)) Reaction of these aldehydes in the presence of bases such as lithium hydride with a acrylate followed by work up with aqueous inorganic bases and hydrolysis, such as by treatment with aqueous base (sodium hydroxide) in a suitable solvent such as ethanol affords, after acidification, a dihydroquinoline-3-carboxylic acid 30.

SCHEME 15

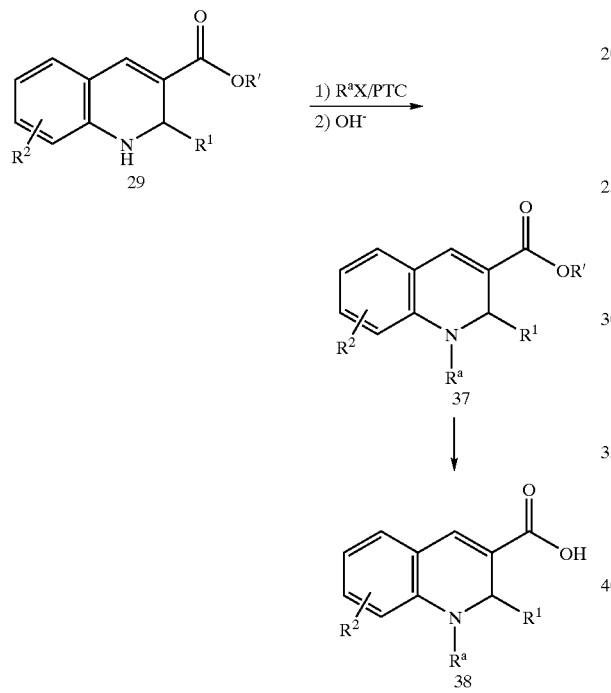

Synthetic Scheme 15 shows a general method for alkylation of the nitrogen of dihydroquinoline-3-carboxylate ester derivatives 29. The step involves treatment of dihydroquinoline-3-carboxylate ester derivatives 29 with alkyl halides such as iodoethane in the presence of phase transfer catalysts such a tetrabutylammonium iodide, and a base such as caustic (50% aqueous sodium hydroxide) in a solvent such as dichloromethane. These conditions afford the N-alkylated dihyrdoquinoline-3-carboxylate esters 37. Saponification of 37 with aqueous base provides N-alkylated-dihyroquinoline-3-carboxylic acid derivatives 38.

SCHEME 16

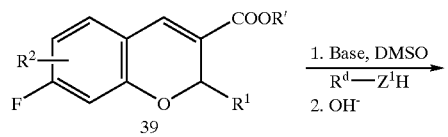

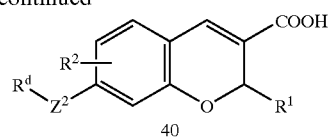

Synthetic Scheme 16 shows a general method for the preparation of a 7-ether ($Z^1$=O) or thioether ($Z^1$=S) substituted benzopyran-3-carboxylic ester. An appropriately substituted phenol, thiophenol, hydroxy-heterocycle, mercaptoheterocycle, alcohol, or alkylthiol can be condensed under basic conditions using a base such as potassium carbonate in a solvent such as dimethysulfoxide, at temperature above room temperature, such as 100° C., with an appropriately substituted 7-fluorobenzopyran derivative 30 to yield the corresponding ether or thioether. Hydrolysis of the ester with an aqueous base such as lithium hydroxide or sodium hydroxide in a solvent mixture such as tetrahydrofuran-ethanol-water yields acid 40. When appropriate, a thioether ($Z^2$=S) can be oxidized to the sulfoxide ($Z^2$=SO) or sulfone ($Z^2$=SO$_2$) with an oxidant such as OXONE® or m-CPBA either before or after ester hydrolysis. In this chemistry $R^d$ can include aryl, heteroaryl, heterocyclic, alicyclic, branched or linear aliphatic, branched or linear per fluoro-aliphatic moiety.

SCHEME 17

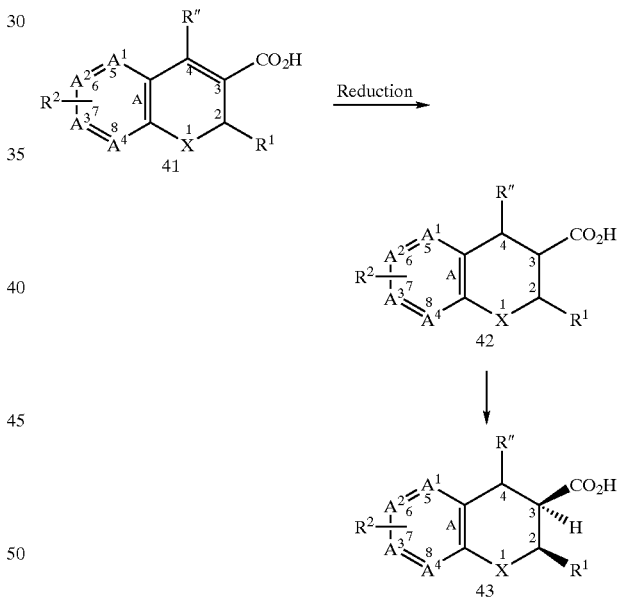

Synthetic Scheme 17 shows the general method for preparing selected 3,4-dihydrobenzopyrans (X=O), 3,4-dihydrobenzothiopyrans (X=S) or 1,2,3,4-tetrahydroquinolines (X=NH or NR$^a$ wherein R$^a$ is as previously defined). For example, treatment of an appropriately substituted 2H-1-benzopyran-3-carboxylic acid 41 (X=O), 2H-1-benzothiopyran-3-carboxylic acid 41 (X=S) or a 1,2-dihydroquinoline-3-carboxylic acid 41 (X=NH or NR$^a$) (wherein R$^1$, R$^2$ and R" are as previously defined) with an appropriate reducing agent yields the corresponding substituted 3,4-dihydrobenzopyran 42 (X=O), substituted 3,4-dihydrobenzothiopyran-3-carboxylic acid 42 (X=S), or substituted 1,2,3,4-tetrahydroquinoline-3-carboxylic acid 42 (X=NR$^a$), respectively. Suitable reducing agents include hydrogenation catalysts such as palladium (Pd on carbon), platinum(IV) oxide (PtO$_2$) and dissolving metal reductions utilizing zinc-HCl or sodium-mercury amalgam. Purification of the racemic mixture yields the isomers 43.

The following examples contain detailed descriptions of the methods of preparation of compounds of Formulas I–V. These detailed descriptions fall within the scope, and serve to exemplify, the above described General Synthetic Procedures which form part of the invention. These detailed descriptions are presented for illustrative purposes only and are not intended as a restriction on the scope of the invention. All parts are by weight and temperatures are in Degrees centigrade unless otherwise indicated. All compounds showed NMR spectra consistent with their assigned structures.

The following abbreviations are used:
HCl—hydrochloric acid
TFA—trifluoroacetic acid
CH$_3$CN—acetonitrile
MgSO$_4$—magnesium sulfate
h—hour
THF—tetrahydrofuran

EXAMPLE 1

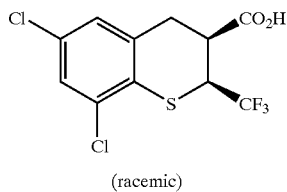

(racemic)

rel-(2R, 3S)-6,8-dichloro-3,4-dihydro-2-(trifluoromethyl)-2H-1-benzothiopyran-3-carbolic acid 6,8-Dichloro-2-trifluoromethyl-2H-1-benzothiopyran-3-carboxylic acid, prepared as described in WO98/47890, (0.32 g, 0.97 mmol) was placed in a Fisher & Porter™ tube with THF (30 mL), and platinium(IV) oxide (0.47 g). The tube was pressurized to 34 psi with hydrogen gas and the reaction mixture stirred at room temperature for about 23 hours. The reaction mixture was filtered through diatomaceous earth, concentrated in vacuo and passed through a column of silica gel with ethyl acetate-hexane-acetic acid (20:80:2) as the eluent, to give a white solid which was recrystallized from isooctane-hexane yielding a white crystalline solid (0.10 g, 31%): mp 165.0–170.2° C. $^1$H NMR (acetone-d$_6$/300 MHz) 7.34 (s, 1H), 7.28 (s, 1H), 4.63–4.69 (m, 1H), 3.40 (d, 1H, J=13.5 Hz), 3.29 (d, 1H, J=18.1 Hz), 3.04–3.16 (m, 1H). $^{19}$F NMR (acetone-d$_6$/282 MHz) −67.3 (d, J=8.7 Hz). FABLRMS m/z 329 (M−H). ESHRMS n/z 347.9830 (M+NH$_4$, Calc'd 347.9840). Anal. Calc'd for C$_{11}$H$_7$Cl$_2$F$_3$O$_2$S: C, 39.90; H, 2.13; Cl, 21.41. Found: C, 40.01; H, 1.74; Cl, 21.70.

EXAMPLE 2

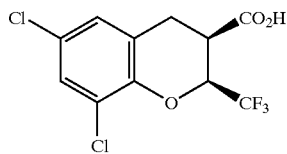

(2S,3R)-6,8-dichloro-3,4-dihydro-2-(trifluoromethyl)-2H-1-benzopyran-3-carboxylic acid.

A 500 mL Parr™ shaker bottle was charged with platinum (IV) oxide (2.99 g) and acetic acid (120 mL) pressurized with hydrogen gas (50 psi) and shaken for 0.75 hours. The hydrogen was vented and the reactor was charged with (2S)-6,8-dichloro-2-(trifluoromethyl)-2H-1-benzopyran-3-carboxylic acid (10.21 g, 32.62 mmol) and pressurized with hydrogen gas (25 psi). After 3 h, the reactor was vented, additional platinum (IV) oxide (1.59 g) was added, the reactor was pressurized with hydrogen gas (25 psi) and shaken for 2 h longer. The crude product mixture was filtered through diatomaceous earth and the filtrate concentrated in vacuo.

The resulting crude product was purified by flash silica chromatography (hexanes-ethyl acetate, 3:1) followed by reverse phase chromatography [C$_{18}$ stationary phase, CH$_3$CN—H$_2$O with 0.1% TFA (gradient 15:85 to 50:50)] providing 5.02 g of a white, oily foam. This foam was further purified by flash silica chromatography (hexanes-ethyl acetate with 2% acetic acid (gradient 4:1 to 0:1) and crystallization from methylene chloride-isooctane (1:10) followed by further purification by reverse phase chromatography [CH$_3$CN—HO with 0.1% TFA (gradient 15:85 to 45:65)] yielding 2.3 g of a sticky foam. This foam was crystallized from methylene chloride-isooctane (1:10) at room temperature yielding the desired product (1.50 g) as fine white clear needles: mp 100.3–101.1° C. $^1$H NMR (acetone-d$_6$ with TFA/400 MHz) 7.33 (d, 1H, J=2.4 Hz), 7.25 (d, 1H, J=2.4 Hz), 5.31–5.22 (m, 1H), 3.59–3.51 (m 1H), 3.16 (dd, 1H, J=6.2, 17.5 Hz), 3.10 (dd, 1H, J=8.1, 17.5 Hz). LRMS m/z 313 (M−H). HRMS m/z 312.9632 (M−H, C$_{11}$H$_6$Cl$_2$F$_3$O$_3$ requires 312.9646). Anal. Calc'd for C$_{11}$H$_7$Cl$_2$F$_3$O$_3$+0.77 wt % H$_2$O: C, 41.61; H, 2.31; Cl, 22.33. Found: C, 41.74; H, 2.22; Cl, 22.05.

EXAMPLE 3

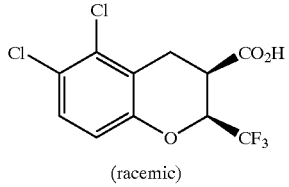

(racemic)

rel-(2R, 3S)-5,6-dichloro-3,4-dihydro-2-(trifluoromethyl)-2H-1-benzopyran-3-carboxylic acid Prepared by a procedure similar to that described in EXAMPLE 1. mp 173.0–174.4° C. $^1$H NMR (acetone-d$_6$/ 300 MHz) 7.43 (d, 1H, J=8.9 Hz), 7.03 (d, 1H, J=8.9 Hz), 5.19–5.22 (m, 1H), 3.59–3.69 (m, 1H), 3.23 (dd, 1H, J=17.9 Hz, 6.2 Hz), 3.13 (dd, 1H, J=17.9 Hz, 7.5 Hz). $^{19}$F NMR (acetone-d$_6$/282 MHz) −74.5 (d, J=7.2 Hz). FABLRMS m/z 313 (M−H). ESHRMS m/z 312.9635 (M−H, Calc'd 312.9646). Anal. Calc'd for C$_{11}$H$_7$Cl$_2$F$_3$O$_3$: C, 41.93; H, 2.24. Found: C, 41.52; H, 2.53.

EXAMPLE 4

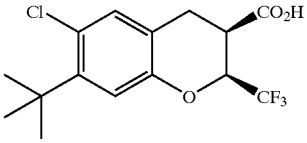

(2S,3R)-6-chloro-3,4-dihydro-7-(1,1-dimethylethyl)-2-(trifluoromethyl)-2H-1-benzopyran-3-carboxylic acid Prepared by a procedure similar to that described in EXAMPLE 1. mp 115.8–120.9° C. $^1$H NMR (acetone-d$_6$/ 300 MHz) 7.23 (s, 1H), 7.02 (s, 1H), 5.10–5.16 (m, 1H), 3.48–3.58 (m, 1H), 3.05–3.20 (m, 2H). $^{19}$F NMR (acetone-$d_6$/282 MHz) −74.3 (d, J=6.5 Hz). ESHRMS m/z 335.0658 (M−H, Calc'd 335.0661). Anal. Calc'd for $C_{15}H_{16}ClF_3O_3$: C, 53.50; H, 4.79; Cl, 10.53. Found: C, 53.19; H, 4.83; Cl, 10.20.

EXAMPLE 5

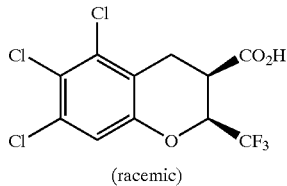

(racemic)

rel-(2R,3S)-3,4-dihydro-5,6,7-trichloro-2-(trifluoromethyl)-2H-1-benzopyran-3-carboxylic acid A solution of 6,7,8-trichloro-2-trifluoromethyl-2H-1-benzopyran-3-carboxylic acid (0.28 g, 0.81 mmol, prepared as described in WO98/47890, in ethanol (10 mL) was treated with concentrated HCl (5 mL) and zinc powder (1.21 g, 18.5 mmol). The mixture was stirred at room temperature for 3 hours, filtered, and concentrated in vacuo. The residue was extracted with ethyl acetate, washed with brine, dried over $MgSO_4$, and concentrated in vacuo to give a white solid (0.31 g) which was a 3:2 mixture of cis and trans isomers. The isomers were separated by reverse phase HPLC to obtain the desired cis isomer as a white solid (0.11 g, 39%): mp 207.3–208.5° C. $^1$H NMR (acetone-$d_6$/300 MHz) 7.23 (s, 1H), 5.17–5.31 (m, 1H), 3.58–3.72 (m, 1H), 3.19 (dd, 1H, J=17.9 Hz, 6.5 Hz), 3.10 (dd, 1H, J=17.9 Hz, 7.7 Hz) $^{19}$F NMR (acetone-$d_6$/282 MHz) −74.6 (d, J=7.2 Hz). ESHRMS m/z 346.9270 (M−H, Calc'd 346.9256). Anal. Calc'd for $C_{11}H_6Cl_3F_3O_3$: C, 37.80; H, 1.73; Cl, 30.43. Found: C, 37.66; H, 1.75; Cl, 30.71.

EXAMPLE 6

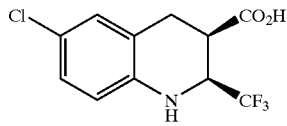

(2S,3R)-6-Chloro-1,2,3,4-tetrahydro-2-(trifluoromethyl)-3-quinolinecarboxylic acid Prepared by a procedure similar to that described in EXAMPLE 5. mp 154.4–154.5° C. $^1$H NMR (acetone-$d_6$/300 MHz) 7.09 (s, 1H), 7.00 (dd, 1H, J=8.7 Hz, 2.4 Hz), 6.77 (d, 1H, J=8.7 Hz), 6.23 (br s, 1H), 4.50–4.66 (m, 1H), 3.17–3.30 (m, 1H), 2.90–3.09 (m, 2H). $^{19}$F NMR (acetone-$d_6$/282 MHz) −72.5 (d, J=8.0 Hz). ESHRMS m/z 280.0351 (M+H, Calc'd 280.0352). Anal. Calc'd for $C_{11}H_9ClF_3NO_2$: C, 47.25; H, 3.24; N, 5.01; Cl, 12.68. Found: C, 46.92; H, 3.05; N, 4.96; Cl, 12.80.

EXAMPLE 7

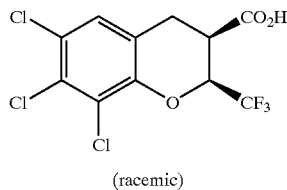

(racemic)

rel-(2R, 3S)-3,4-dihydro-6,7,8-trichloro-2-(trifluoromethyl)-2H-1-benzopyran-3-carboxylic acid Prepared by a procedure similar to that described in EXAMPLE 5. mp 205.2–208.1° C. $^1$H NMR (acetone-$d_6$/300 MHz) 7.46 (s, 1H, J=0.8 Hz), 5.28–5.38 (m, 1H), 3.56–3.63 (m, 1H), 3.25. (dd, 1H, J=17.7 Hz, 6.0 Hz), 3.16 (dd, 1H, J=17.5 Hz, 7.7 Hz). $^{19}$F NMR (acetone-$d_6$/282 MHz) −74.8 (d, J=6.5 Hz). ESHRMS m/z 346.9249 (M−H, Calc'd 346.9256). Anal. Calc'd for $C_{11}H_6Cl_3F_3O_3$: C, 37.80; H, 1.73; Cl, 30.43. Found: C, 37.69; H, 1.49; Cl, 30.33.

EXAMPLE 8

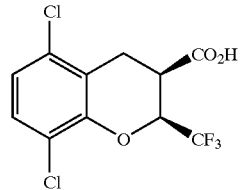

(racemic; ca. 85% s-cis, 15% s-trans)
rel-(2R,3S)-5,8-dichloro-3,4-dihydro-2-(trifluoromethyl)-2H-1-benzopyran-3-carboxylic acid Prepared by a procedure similar to that described in EXAMPLE 5. mp 185.7–188.9° C. $^1$H NMR (acetone-$d_6$/300 MHz) 7.33 (d, 1H, J=8.7 Hz), 7.14 (d, 1H, J=8.5 Hz), 5.20–5.37 (m, 1H), 3.65 (m, 1H), 3.19 (dd, 1H, J=17.7 Hz, 6.3 Hz), 3.09 (dd, 1H, J=17.7 Hz, 7.9 Hz). $^{19}$F NMR (acetone-$d_6$/282 MHz) −74.5 (d, J=7.1 Hz). FABLRMS m/z 313 (M−H). ESHRMS m/z 312.9645 (M−H, Calc'd 312.9646). Anal. Calc'd for $C_{11}H_7Cl_2F_3O_3$: C, 41.93; H, 2.24; Cl, 22.50. Found: C, 41.93; H, 2.15; Cl, 22.31.

EXAMPLE 9

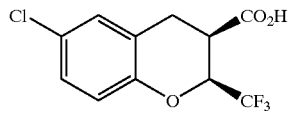

(2S,3R)-6-chloro-3,4-dihydro-2-(trifluoromethyl)-2H-1-benzopyran-3-carboxylic acid Prepared by a procedure similar to that described in EXAMPLE 5. mp 118.1–119.2° C. $^1$H NMR (acetone-$d_6$/300 MHz) 7.24 (s, 1H), 7.16 (d, 1H, J=8.7 Hz), 6.94 (d, 1H, J=8.7 Hz), 5.10–5.22 (m, 1H), 3.45–3.58 (m, 1H) 3.01–3.22 (m, 2H). $^{19}$F NMR (acetone-$d_6$/282 MHz) −74.4 (d, J=7.2 Hz). ESHRMS m/z 279.0005 (M−H, Calc'd 279.0036). Anal. Calc'd for $C_{11}H_8ClF_3O_3$: C, 47.08; H, 2.87; Cl, 12.63. Found: C, 46.87; H, 2.79; Cl, 12.52.

EXAMPLE 10

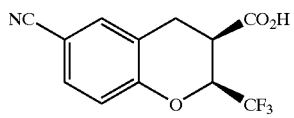

(racemic: ca. 93% s-cis, 7% s-trans)
rel-(2R,3S)-6-cyano-3,4-dihydro-2-(trifluoromethyl)-2H-1-benzopyran-3-carboxylic acid Prepared by a procedure similar to that described in EXAMPLE 5. mp 169.0–170.4° C. $^1$H NMR (acetone-$d_6$/300 MHz) 7.70 (s, 1H), 7.60 (d, 1H, J=8.5 Hz), 7.14 (d, 1H, J=8.5 Hz), 5.24–5.37 (m, 1H), 3.55–3.67 (m, 1H) 3.26 (dd, 1H, J=17.2 Hz, 5.9 Hz), 3.19 (dd, 1H, J=17.5 Hz, 8.3 Hz). $^{19}$F NMR (acetone-$d_6$/282 MHz) −74.6 (d, J=7.2 Hz). ESHRMS m/z 270.0365 (M−H, Calc'd 270.0378). Anal. Calc'd for $C_{12}H_8F_3NO_3$: C, 53.15; H, 2.97; N, 5.16. Found: C, 52.89; H, 2.73; N, 5.13.

EXAMPLE 11

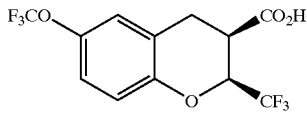

(racemic)
rel-(2R,3S)-3,4-dihydro-6-trifluoromethoxy-2-(trifluoromethyl)-2H-1-benzopyran-3-carboxylic acid Prepared by a procedure similar to that described in EXAMPLE 5. mp 120.1–120.8° C. $^1$H NMR (acetone-$d_6$/300 MHz) 7.25 (s, 1H), 7.16 (d, 1H, J=8.9 Hz), 7.06 (d, 1H, J=8.9 Hz), 5.15–5.28 (m, 1H), 3.51–3.61 (m, 1H) 3.23 (dd, 1H, J=17.3 Hz, 5.9 Hz), 3.17 (dd, 1H, J=17.3 Hz, 8.5 Hz). $^{19}$F NMR (acetone-$d_6$/282 MHz) −59.4 (s, 3F), −74.5 (d, 3F, J=7.2 Hz). ESHRMS m/z 329.0288 (M−H, Calc'd 329.0249). Anal. Calc'd for $C_{12}H_8F_6O_4$: C, 43.65; H, 2.44. Found: C, 43.87; H, 2.33.

Biological Evaluation

Rat Carrageenan Foot Pad Edema Test

The carrageenan foot edema test was performed with materials, reagents and procedures essentially as described by Winter, et al., (*Proc. Soc. Exp. Biol. Med.*, 111, 544 (1962)). Male Sprague-Dawley rats were selected in each group so that the average body weight was as close as possible. Rats were fasted with free access to water for over sixteen hours prior to the test. The rats were dosed orally (1 mL) with compounds suspended in vehicle containing 0.5% methylcellulose and 0.025% surfactant, or with vehicle alone. One hour later a subplantar injection of 0.1 mL of 1% solution of carrageenan/sterile 0.9% saline was administered and the volume of the injected foot was measured with a displacement plethysmometer connected to a pressure transducer with a digital indicator. Three hours after the injection of the carrageenan, the volume of the foot was again measured. The average foot swelling in a group of drug-treated animals was compared with that of a group of placebo-treated animals and the percentage inhibition of edema was determined (Otterness and Bliven, *Laboratory Models for Testing NSAIDs*, in Non-steroidal Anti-Inflammatory Drugs, (J. Lombardino, ed. 1985)). The % inhibition shows the % decrease from control paw volume determined in this procedure and the data for selected compounds in this invention are summarized in Table I.

TABLE I

| Example | RAT PAW EDEMA<br>% Inhibition<br>@ 30 mg/kg body weight | ANALGESIA<br>% Inhibition<br>@ 30 mg/kg body weight |
|---|---|---|
| 2 | 52 | 56 |

Evaluation of COX-1 and COX-2 Activity In Vitro

The compounds of this invention exhibited inhibition in vitro of COX-2. The COX-2 inhibition activity of the compounds of this invention illustrated in the Examples was determined by the following methods.

a. Preparation of recombinant COX baculoviruses

Recombinant COX-1 and COX-2 were prepared as described by Gierse et al, [*J. Biochem.*, 305, 479–84 (1995)]. A 2.0 kb fragment containing the coding region of either human or murine COX-1 or human or murine COX-2 was cloned into a BamHI site of the baculovirus transfer vector pVL1393 (Invitrogen) to generate the baculovirus transfer vectors for COX-1 and COX-2 in a manner similar to the method of D. R. O'Reilly et al (*Baculovirus Expression Vectors: A Laboratory Manual* (1992)). Recombinant baculoviruses were isolated by transfecting 4 μg of baculovirus transfer vector DNA into SF9 insect cells (2×10$^8$) along with 200 ng of linearized baculovirus plasmid DNA by the calcium phosphate method. See M. D. Summers and G. E. Smith, *A Manual of Methods for Baculovirus Vectors and Insect Cell Culture Procedures*, Texas Agric. Exp. Station Bull. 1555 (1987). Recombinant viruses were purified by three rounds of plaque purification and high titer (10$^7$–10$^8$ pfu/mL) stocks of virus were prepared. For large scale production, SF9 insect cells were infected in 10 liter fermentors (0.5×10$^6$/mL) with the recombinant baculovirus stock such that the multiplicity of infection was 0.1. After 72 hours the cells were centrifuged and the cell pellet homogenized in Tris/Sucrose (50 mM: 25%, pH 8.0) containing 1% 3-[(3-cholamidopropyl) dimethylammino]-1-propanesulfonate (CHAPS). The homogenate was centrifuged at 10,000×G for 30 minutes, and the resultant supernatant was stored at −80° C. before being assayed for COX activity.

b. Assay for COX-1 and COX-2 activity

COX activity was assayed as PGE$_2$ formed/μg protein/time using an ELISA to detect the prostaglandin released. CHAPS-solubilized insect cell membranes containing the appropriate COX enzyme were incubated in a potassium phosphate buffer (50 mM, pH 8.0) containing epinephrine, phenol, and heme with the addition of arachidonic acid (10 μM). Compounds were pre-incubated with the enzyme for 10–20 minutes prior to the addition of arachidonic acid. Any reaction between the arachidonic acid and the enzyme was stopped after ten minutes at 37° C./room temperature by transferring 40 μl of reaction mix into 160 μl ELISA buffer and 25 μM indomethacin. The PGE$_2$ formed was measured by standard ELISA technology (Cayman Chemical). Results are shown in Table II.

c. Fast assay for COX-1 and COX-2 activity

COX activity was assayed as PGE$_2$ formed/μg protein/time using an ELISA to detect the prostaglandin released. CHAPS-solubilized insect cell membranes containing the appropriate COX enzyme were incubated in a potassium phosphate buffer (0.05 M Potassium phosphate, pH 7.5, 2 μM phenol, 1 μM heme, 300 μM epinephrine) with the addition of 20 μl of 100 μM arachidonic acid (10 μM). Compounds were pre-incubated with the enzyme for 10 minutes at 25° C. prior to the addition of arachidonic acid.

Any reaction between the arachidonic acid and the enzyme was stopped after two minutes at 37° C./room temperature by transferring 40 μl of reaction mix into 160 μl ELISA buffer and 25 μM indomethacin. The $PGE_2$ formed was measured by standard ELISA technology (Cayman Chemical). Results are shown in Table II.

TABLE II

| Example | COX-2* $IC_{50}$ μM | COX-1* $IC_{50}$ μM | COX-2 $IC_{50}$ μM | COX-1 $IC_{50}$ μM |
|---|---|---|---|---|
| 1  | 0.6 | 0.6  | 0.3  | 0.6  |
| 2  | 0.3 | 1.0  | 0.2  | 2.8  |
| 3  | 0.2 | 5.7  | 0.2  | >100 |
| 4  | 1.6 | 1.3  | >100 | 12   |
| 5  | 0.4 | >100 | 0.4  | >100 |
| 6  | 2.6 | >100 | 25   | >100 |
| 7  | 0.6 | 54   | 0.7  | >100 |
| 8  | 2.3 | 8.7  | 2.0  | 22   |
| 9  | 0.5 | >100 | 29   | >100 |
| 10 | 4.8 | >100 | 18   | >100 |
| 11 | 0.6 | 65   | 0.4  | >100 |

Also embraced within this invention is a class of pharmaceutical compositions comprising the active compounds of Formula I in association with one or more non-toxic, pharmaceutically-acceptable carriers and/or diluents and/or adjuvants (collectively referred to herein as "carrier" materials) and, if desired, other active ingredients. The active compounds of the present invention may be administered by any suitable route, preferably in the form of a pharmaceutical composition adapted to such a route, and in a dose effective for the treatment intended. The active compounds and composition may, for example, be administered orally, pulmonary, mucosally, intravascularly, intraperitoneally, subcutaneously, intramuscularly or topically.

The phrase "co-therapy" (or "combination-therapy"), in defining use of a cyclooxygenase-2 inhibitor agent and another pharmaceutical agent, is intended to embrace administration of each agent in a sequential manner in a regimen that will provide beneficial effects of the drug combination, and is intended as well to embrace co-administration of these agents in a substantially simultaneous manner, such as in a single capsule having a fixed ratio of these active agents or in multiple, separate capsules for each agent.

The phrase "therapeutically-effective" is intended to qualify the amount of each agent which will achieve the goal of improvement in disease severity and the frequency of incidence over treatment of each agent by itself, while avoiding adverse side effects typically associated with alternative therapies.

For oral administration, the pharmaceutical composition may be in the form of, for example, a tablet, capsule, suspension or liquid. The pharmaceutical composition is preferably made in the form of a dosage unit containing a particular amount of the active ingredient. Examples of such dosage units are tablets or capsules. The active ingredient may also be administered by injection as a composition wherein, for example, saline, dextrose or water may be used as a suitable carrier.

The amount of therapeutically active compounds which are administered and the dosage regimen for treating a disease condition with the compounds and/or compositions of this invention depends on a variety of factors, including the age, weight, sex and medical condition of the subject, the severity of the disease, the route and frequency of administration, and the particular compound employed, and thus may vary widely. The pharmaceutical compositions may contain active ingredients in the range of about 0.1 to 2000 mg, preferably in the range of about 0.5 to 500 mg and most preferably between about 1 and 100 mg. A daily dose of about 0.01 to 100 mg/kg body weight, preferably between about 0.5 and about 20 mg/kg body weight and most preferably between about 0.1 to 10 mg/kg body weight, may be appropriate. The daily dose can be administered in one to four doses per day.

In the case of psoriasis and other skin conditions, it may be preferable to apply a topical preparation of compounds of this invention to the affected area two to four times a day.

For inflammations of the eye or other external tissues, e.g., mouth and skin, the formulations are preferably applied as a topical ointment or cream, or as a suppository, containing the active ingredients in a total amount of, for example, 0.075 to 30% w/w, preferably 0.2 to 20% w/w and most preferably 0.4 to 15% w/w. When formulated in an ointment, the active ingredients may be employed with either paraffinic or a water-miscible ointment base. Alternatively, the active ingredients may be formulated in a cream with an oil-in-water cream base. If desired, the aqueous phase of the cream base may include, for example at least 30% w/w of a polyhydric alcohol such as propylene glycol, butane-1,3-diol, mannitol, sorbitol, glycerol, polyethylene glycol and mixtures thereof. The topical formulation may desirably include a compound which enhances absorption or penetration of the active ingredient through the skin or other affected areas. Examples of such dermal penetration enhancers include dimethylsulfoxide and related analogs. The compounds of this invention can also be administered by a transdermal device. Preferably topical administration will be accomplished using a patch either of the reservoir and porous membrane type or of a solid matrix variety. In either case, the active agent is delivered continuously from the reservoir or microcapsules through a membrane into the active agent permeable adhesive, which is in contact with the skin or mucosa of the recipient. If the active agent is absorbed through the skin, a controlled and predetermined flow of the active agent is administered to the recipient. In the case of microcapsules, the encapsulating agent may also function as the membrane.

The oily phase of the emulsions of this invention may be constituted from known ingredients in a known manner. While the phase may comprise merely an emulsifier, it may comprise a mixture of at least one emulsifier with a fat or an oil or with both a fat and an oil. Preferably, a hydrophilic emulsifier is included together with a lipophilic emulsifier which acts as a stabilizer. It is also preferred to include both an oil and a fat. Together, the emulsifier(s) with or without stabilizer(s) make-up the so-called emulsifying wax, and the wax together with the oil and fat make up the so-called emulsifying ointment base which forms the oily dispersed phase of the cream formulations. Emulsifiers and emulsion stabilizers suitable for use in the formulation of the present invention include Tween 60, Span 80, cetostearyl alcohol, myristyl alcohol, glyceryl monostearate, and sodium lauryl sulfate, among others.

The choice of suitable oils or fats for the formulation is based on achieving the desired cosmetic properties, since the solubility of the active compound in most oils likely to be used in pharmaceutical emulsion formulations is very low. Thus, the cream should preferably be a non-greasy, non-staining and washable product with suitable consistency to avoid leakage from tubes or other containers. Straight or branched chain, mono- or dibasic alkyl esters such as di-isoadipate, isocetyl stearate, propylene glycol diester of coconut fatty acids, isopropyl myristate, decyl oleate, isopropyl palmitate, butyl stearate, 2-ethylhexyl palpitate or a blend of branched chain esters may be used. These may be used alone or in combination depending on the properties required. Alternatively, high melting point lipids such as white soft paraffin and/or liquid paraffin or other mineral oils can be used.

Formulations suitable for topical administration to the eye also include eye drops wherein the active ingredients are dissolved or suspended in suitable carrier, especially an aqueous solvent for the active ingredients. The antiinflammatory active ingredients are preferably present in such formulations in a concentration of 0.5 to 20%, advantageously 0.5 to 10% and particularly about 1.5% w/w.

For therapeutic purposes, the active compounds of this combination invention are ordinarily combined with one or more adjuvants appropriate to the indicated route of administration. If administered per os, the compounds may be admixed with lactose, sucrose, starch powder, cellulose esters of alkanoic acids, cellulose alkyl esters, talc, stearic acid, magnesium stearate, magnesium oxide, sodium and calcium salts of phosphoric and sulfuric acids, gelatin, acacia gum, sodium alginate, polyvinylpyrrolidone, and/or polyvinyl alcohol, and then tableted or encapsulated for convenient administration. Such capsules or tablets may contain a controlled-release formulation as may be provided in a dispersion of active compound in hydroxypropylmethyl cellulose. Formulations for parenteral administration may be in the form of aqueous or non-aqueous isotonic sterile injection solutions or suspensions. These solutions and suspensions may be prepared from sterile powders or granules having one or more of the carriers or diluents mentioned for use in the formulations for oral administration. The compounds may be dissolved in water, polyethylene glycol, propylene glycol, ethanol, corn oil, cottonseed oil, peanut oil, sesame oil, benzyl alcohol, sodium chloride, and/or various buffers. Other adjuvants and modes of administration are well and widely known in the pharmaceutical art.

For pulmonary administration, the pharmaceutical composition may be administered in the form of an aerosol or with an inhaler including dry powder aerosol.

All mentioned references are incorporated by reference as if here written.

Although this invention has been described with respect to specific embodiments, the details of these embodiments are not to be construed as limitations.

What is claimed is:
1. A compound of Formula I

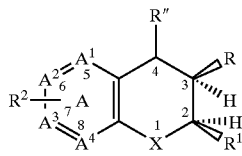

wherein X is O;
wherein R is selected from carboxyl, aminocarbonyl, $C_1$–$C_6$-alkylsulfonylaminocarbonyl and $C_1$–$C_6$-alkoxycarbonyl;
wherein R" is selected from hydrido, phenyl, thienyl, $C_1$–$C_6$-alkyl and $C_2$–$C_6$-alkenyl;
wherein $R^1$ is selected from $C_1$–$C_3$-perfluoroalkyl, chloro, $C_1$–$C_6$-alkylthio, nitro, cyano and cyano-$C_1$–$C_3$-alkyl;
wherein $R^2$ is one or more radicals independently selected from hydrido, halo, $C_1$–$C_6$-alkyl, $C_2$–$C_6$-alkenyl, $C_2$–$C_6$-alkynyl, halo-$C_2$–$C_6$-alkynyl, aryl-$C_1$–$C_3$-alkyl, aryl-$C_2$–$C_6$-alkynyl, aryl-$C_2$–$C_6$-alkenyl, $C_1$–$C_6$-alkoxy, methylenedioxy, $C_1$–$C_6$-alkylthio, $C_1$–$C_6$-alkylsulfinyl, aryloxy, arylthio, arylsulfinyl, heteroaryloxy, $C_1$–$C_6$-alkoxy-$C_1$–$C_6$-alkyl, aryl-$C_1$–$C_6$-alkoxy, heteroaryl-$C_1$–$C_6$-alkoxy, aryl-$C_1$–$C_6$-alkoxy-$C_1$–$C_6$-alkyl, $C_1$–$C_6$-haloalkyl, $C_1$–$C_6$-haloalkoxy, $C_1$–$C_6$-haloalkylthio, $C_1$–$C_6$-haloalkylsulfinyl, $C_1$–$C_6$-haloalkylsulfonyl, $C_1$–$C_3$-(haloalkyl)-$C_1$–$C_3$-hydroxyalkyl, $C_1$–$C_6$-hydroxyalkyl, hydroxyimino-$C_1$–$C_6$-alkyl, $C_1$–$C_6$-alkylamino, arylamino, N-aryl-N—$C_1$–$C_6$-alkylamino, heteroarylamino, N-heteroaryl-N—$C_1$–$C_6$-alkylamino, nitro, cyano, amino, aminosulfonyl, $C_1$–$C_6$-alkylaminosulfonyl, arylaminosulfonyl, heteroarylaminosulfonyl, N-aryl-$C_1$–$C_6$-alkylaminosulfonyl, N-heteroaryl-$C_1$–$C_6$-alkylaminosulfonyl, heterocyclylsulfonyl, $C_1$–$C_6$-alkylsulfonyl, aryl-$C_1$–$C_6$-alkylsulfonyl, optionally substituted aryl, optionally substituted heteroaryl, aryl-$C_1$–$C_6$-alkylcarbonyl, heteroaryl-$C_1$–$C_6$-alkylcarbonyl, heteroarylcarbonyl, arylcarbonyl, aminocarbonyl, $C_1$–$C_6$-alkoxycarbonyl, formyl, $C_1$–$C_6$-haloalkylcarbonyl and $C_1$–$C_6$-alkylcarbonyl; and
wherein the A ring atoms $A^1$, $A^2$, $A^3$ and $A^4$ are carbon;
or wherein $R^2$ together with ring A forms a radical selected from naphthyl, quinolyl, isoquinolyl, quinolizinyl, quinoxalinyl and dibenzofuryl;
or an isomer or pharmaceutically acceptable salt thereof.

2. A compound of claim 1 wherein X is O; wherein R is selected from carboxyl, aminocarbonyl, $C_1$–$C_4$-alkylsulfonylaminocarbonyl and $C_1$–$C_4$-alkoxycarbonyl; wherein R" is selected from hydrido, phenyl, thienyl, $C_1$–$C_4$-alkyl and $C_2$–$C_4$-alkenyl; wherein $R^1$ is selected from $C_1$–$C_3$-perfluoroalkyl, chloro, $C_1$–$C_4$-alkylthio, nitro, cyano and cyano-$C_1$–$C_3$-alkyl; wherein $R^2$ is one or more radicals independently selected from hydrido, halo, $C_1$–$C_4$-alkyl, $C_2$–$C_4$-alkenyl, $C_2$–$C_6$-alkynyl, halo-$C_2$–$C_6$-alkynyl, aryl-$C_1$–$C_3$-alkyl, aryl-$C_2$–$C_4$-alkynyl, aryl-$C_2$–$C_4$-alkenyl, $C_1$–$C_4$-alkoxy, methylenedioxy, $C_1$–$C_4$-alkylthio, $C_1$–$C_4$-alkylsulfinyl, aryloxy, arylthio, arylsulfinyl, heteroaryloxy, $C_1$–$C_4$-alkoxy-$C_1$–$C_4$-alkyl, aryl-$C_1$–$C_4$-alkoxy, heteroaryl-$C_1$–$C_4$-alkoxy, aryl-$C_1$–$C_4$-alkoxy-$C_1$–$C_4$-alkyl, $C_1$–$C_4$-haloalkyl, $C_1$–$C_4$-haloalkoxy, $C_1$–$C_4$-haloalkylthio, $C_1$–$C_4$-haloalkylsulfinyl, $C_1$–$C_4$-haloalkylsulfonyl, $C_1$–$C_3$-(haloalkyl)-$C_1$–$C_3$-hydroxyalkyl, $C_1$–$C_4$-hydroxyalkyl, hydroxyimino-$C_1$–$C_4$-alkyl, $C_1$–$C_4$-alkylamino, arylamino, N-aryl-N—$C_1$–$C_4$-alkylamino, heteroarylamino, N-heteroaryl-N—$C_1$–$C_4$-alkylamino, nitro, cyano, amino, aminosulfonyl, $C_1$–$C_4$-alkylaminosulfonyl, arylaminosulfonyl, heteroarylaminosulfonyl, aryl-$C_1$–$C_4$-alkylaminosulfonyl, heteroaryl-$C_1$–$C_4$-alkylaminosulfonyl, heterocyclylsulfonyl, $C_1$–$C_4$-alkylsulfonyl, aryl-$C_1$–$C_4$-alkylsulfonyl, optionally substituted aryl, optionally substituted heteroaryl, aryl-$C_1$–$C_4$-alkylcarbonyl, heteroaryl-$C_1$–$C_4$-alkylcarbonyl, heteroarylcarbonyl, arylcarbonyl, aminocarbonyl, $C_1$–$C_4$-alkoxycarbonyl, formyl, $C_1$–$C_4$-haloalkylcarbonyl and $C_1$–$C_4$-alkylcarbonyl; and wherein the A ring atoms $A^1$, $A^2$, $A^3$ and $A^4$ are carbon; or wherein $R^2$ together with ring A forms a naphthyl or quinolyl radical; or an isomer or pharmaceutically acceptable salt thereof.

3. A compound of claim 2 wherein X is O; wherein R is carboxyl; wherein R" is selected from hydrido, $C_1$–$C_3$-alkyl and $C_2$–$C_3$-alkenyl; wherein $R^1$ is selected from $C_1$–$C_3$-perfluoroalkyl; wherein $R^2$ is one or more radicals independently selected from hydrido, halo, $C_1$–$C_4$-alkyl, $C_2$–$C_3$-alkenyl, $C_2$–$C_6$-alkynyl, halo-$C_2$–$C_6$-alkynyl, optionally substituted phenyl-$C_1$–$C_3$-alkyl, optionally substituted phenyl-$C_2$–$C_3$-alkynyl, phenyl-$C_2$–$C_3$-alkenyl, $C_1$–$C_3$-alkoxy, methylenedioxy, $C_1$–$C_3$-alkoxy-$C_1$–$C_3$-alkyl, $C_1$–$C_3$-alkylthio, $C_1$–$C_3$-alkylsulfinyl, optionally substituted phenyloxy, optionally substituted phenylthio, optionally substituted phenylsulfinyl, $C_1$–$C_3$-haloalkyl-$C_1$–$C_3$-hydroxyalkyl, phenyl-$C_1$–$C_3$-alkoxy-$C_1$–$C_3$-alkyl, $C_1$–$C_3$-haloalkyl, $C_1$–$C_3$-haloalkoxy, $C_1$–$C_3$-haloalkylthio, $C_1$–$C_3$-hydroxyalkyl, $C_1$–$C_3$-alkoxy-$C_1$–$C_3$-alkyl, hydroxyimino-$C_1$–$C_3$-alkyl, $C_1$–$C_6$-alkylamino, nitro, cyano, amino, aminosulfonyl, N-alkylaminosulfonyl, N-arylaminosulfonyl, N-heteroarylaminosulfonyl, N-(phenyl-$C_1$–$C_6$-alkyl)aminosulfonyl, N-(heteroaryl-$C_1$–$C_6$-alkyl)aminosulfonyl, phenyl-$C_1$–$C_3$-alkylsulfonyl, 5- to 8-membered heterocyclylsulfonyl, $C_1$–$C_3$-alkylsulfonyl, optionally substituted phenyl, optionally substituted 5- to 9-membered heteroaryl, phenyl-$C_1$–$C_3$-alkylcarbonyl, phenylcarbonyl, 4-chlorophenylcarbonyl, 4-hydroxyphenylcarbonyl, 4-trifluoromethylphenylcarbonyl, 4-methoxyphenylcarbonyl, aminocarbonyl, formyl, and $C_1$–$C_6$-alkylcarbonyl; wherein the A ring atoms $A^1$, $A^2$, $A^3$ and $A^4$ are carbon; or wherein $R^2$ together with ring A forms a naphthyl, benzofurylphenyl, or quinolyl radical; or an isomer or pharmaceutically acceptable salt thereof.

4. A compound of claim 3 wherein X is O; wherein R is carboxyl; wherein R" is selected from hydrido, ethyl and ethenyl; wherein $R^1$ is trifluoromethyl or pentafluoroethyl; wherein $R^2$ is one or more radicals independently selected from hydrido, chloro, bromo, fluoro, iodo, methyl, tert-butyl, ethenyl, ethynyl, 5-chloro-1-pentynyl, 1-pentynyl, 3,3-dimethyl-1-butynyl, benzyl, phenylethyl, phenylethynyl, 4-chlorophenyl-ethynyl, 4-methoxyphenyl-ethynyl, phenylethenyl, methoxy, methylthio, methylsulfinyl, phenyloxy, phenylthio, phenylsulfinyl, methylenedioxy, benzyloxymethyl, trifluoromethyl, difluoromethyl, pentafluoroethyl, trifluoromethoxy, trifluoromethylthio, hydroxymethyl, hydroxy-trifluoroethyl, methoxymethyl, hydroxyiminomethyl, N-methylamino, nitro, cyano, amino, aminosulfonyl, N-methylaminosulfonyl, N-phenylaminosulfonyl, N-furylaminosulfonyl, N-(benzyl)aminosulfonyl, N-(furylmethyl)aminosulfonyl, benzylsulfonyl, phenylethylaminosulfonyl, furylsulfonyl, methylsulfonyl, phenyl, phenyl substituted with one or more radicals selected from chloro, fluoro, bromo, methoxy, methylthio and methylsulfonyl, benzimidazolyl, thienyl, thienyl substituted with chloro, furyl, furyl substituted with chloro, benzylcarbonyl, optionally substituted phenylcarbonyl, aminocarbonyl, formyl and methylcarbonyl; wherein the A ring atoms $A^1$, $A^2$, $A^3$ and $A^4$ are carbon; or wherein $R^2$ together with ring A forms a naphthyl, or quinolyl radical; or an isomer or pharmaceutically acceptable salt thereof.

5. A compound of claim 4 selected from compounds, and their isomers and pharmaceutically-acceptable salts, of the group consisting of (2S,3R)-6,8-dichloro-3,4-dihydro-2-(trifluoromethyl)-2H-1-benzopyran-3-carboxylic acid;

rel-(2R,3S)-5,6-dichloro-3,4-dihydro-2-(trifluoromethyl)-2H-1-benzopyran-3-carboxylic acid;

(2S,3R)-6-chloro-3,4-dihydro-7-(1,1-dimethylethyl)-2-(trifluoromethyl)-2H-1-benzopyran-3-carboxylic acid;

rel-(2R,3S)-3,4-dihydro-5,6,7-trichloro-2-(trifluoromethyl)-2H-1-benzopyran-3-carboxylic acid;

rel-(2R,3S)-3,4-dihydro-6,7,8-trichloro-2-(trifluoromethyl)-2H-1-benzopyran-3-carboxylic acid;

rel-(2R,3S)-5,8-dichloro-3,4-dihydro-2-(trifluoromethyl)-2H-1-benzopyran-3-carboxylic acid;

(2S,3R)-6-chloro-3,4-dihydro-2-(trifluoromethyl)-2H-1-benzopyran-3-carboxylic acid;

rel-(2R,3S)-6-cyano-3,4-dihydro-2-(trifluoromethyl)-2H-1-benzopyran-3-carboxylic acid; and rel-(2R,3S)-3,4-dihydro-6-trifluoromethoxy-2-(tnfluoromethyl)-2H-1-benzopyran-3-carboxylic acid.

6. A compound of Formula II

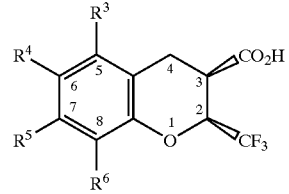

II wherein $R^3$ is selected from hydrido, $C_1$–$C_3$-alkyl, $C_1$–$C_3$-hydroxyalkyl, $C_1$–$C_3$-alkoxy and halo;

wherein $R^4$ is selected from hydrido, halo, $C_1$–$C_4$-alkyl, $C_1$–$C_3$-alkylthio, $C_1$–$C_3$-haloalkyl, amino, aminosulfonyl, $C_1$–$C_3$-alkylsulfonyl, $C_1$–$C_3$-alkylsulfinyl, $C_1$–$C_3$-alkoxy-$C_1$–$C_3$-alkyl, $C_1$–$C_3$-alkylcarbonyl, formyl, cyano, $C_1$–$C_3$-haloalkylthio, substituted or unsubstituted phenylcarbonyl, $C_1$–$C_3$-haloalkoxy, $C_1$–$C_3$-alkoxy, aryl-$C_1$–$C_3$-alkylcarbonyl, di-$C_1$–$C_3$-alkylaminosulfonyl, $C_1$–$C_3$-alkylaminosulfonyl, aryl-$C_1$–$C_3$-alkylaminosulfonyl, 5- or 6-heteroaryl-$C_1$–$C_3$-alkylaminosulfonyl, 5- or 6-membered heteroaryl, $C_1$–$C_3$-hydroxyalkyl, substituted or unsubstituted phenyl and 5- or 6-membered nitrogen-containing heterocyclylsulfonyl;

wherein $R^5$ is selected from hydrido, $C_1$–$C_4$-alkyl, halo, $C_1$–$C_3$-haloalkyl, $C_1$–$C_4$-hydroxyalkyl, $C_2$–$C_3$-alkynyl, $C_2$–$C_3$-alkenyl, $C_1$–$C_3$-alkoxy, phenoxy, phenoxy independently substituted with one or more radicals selected from $C_1$–$C_3$-haloalkyl, nitro, carboxyl, $C_1$–$C_3$-haloalkoxy, $C_1$–$C_3$-alkoxy, cyano, $C_1$–$C_3$-alkyl and halo, naphthyloxy, naphthyloxy substituted with one or more halo radicals, phenylthio, phenylthio substituted with one or more halo radicals, phenylsulfinyl, phenylsulfinyl substituted with one or more halo radicals, phenylsulfonyl, phenylsulfonyl substituted with one or more halo radicals, pyridinyloxy, pyridinyloxy substituted with one or more halo radicals, and phenyl; and wherein $R^6$ is selected from hydrido, halo, cyano, hydroxyiminomethyl, $C_1$–$C_3$-hydroxyalkyl, $C_2$–$C_3$-alkynyl, phenyl-$C_2$–$C_3$-alkynyl, $C_1$–$C_4$-alkyl, $C_1$–$C_3$-alkoxy, formyl and phenyl; or an isomer or pharmaceutically acceptable salt thereof.

7. Compound of claim 6 wherein $R^3$ is hydrido or chloro; wherein $R^4$ selected from hydrido, chloro, methyl, tert-butyl, methylthio, trifluoromethyl, difluoromethyl, pentafluoroethyl, trifluoromethylthio, trifluoromethoxy, cyano, substituted or unsubstituted phenylcarbonyl, and substituted or unsubstituted phenyl; wherein $R^5$ is selected from hydrido, methyl, tert-butyl, 2,2,2-trifluoroethoxy, 2-hydroxy-1,1-dimethylethyl, phenoxy, 4-methoxyphenoxy, 4-chlorophenoxy, 3-chlorophenoxy, 2-chlorophenoxy, 4-cyanophenoxy, 2,6-dimethylphenoxy, 2,4-dichlorophenoxy, 3,4-difluorophenoxy, 4-chloro-3-fluorophenoxy, 4-(trifluoromethyl)phenoxy, 4-nitrophenoxy, 4-carboxyphenoxy, 3-carboxyphenoxy, 2-chloro-4-carboxyphenoxy, 4-(trifluoromethoxy)phenoxy, 2-bromo-4-chlorophenoxy, (6-bromo-2-naphthalenyl)oxy, phenylthio, (4-methoxyphenyl)thio, (4-chlorophenyl)thio, (4-chlorophenyl)sulfinyl, (4-chlorophenyl)sulfonyl, (6-chloro-2-pyridinyl)oxy, (2-chloro-3-pyridinyl)oxy, (3-pyridinyl)oxy, (2-pyridinyl)oxy, iodo, ethenyl, ethynyl, chloro; and wherein $R^6$ selected from hydrido, chloro, thienyl, hydroxyiminomethyl, substituted or unsubstituted phenylethynyl, phenyl and substituted phenyl; or an isomer or pharmaceutically acceptable salt thereof.

8. A compound of claim 7 selected from compounds, and their isomers and pharmaceutically-acceptable salts, of the group consisting of (2S,3R)-6,8-dichloro-3,4-dihydro-2-(trifluoromethyl)-2H-1-benzopyran-3-carboxylic acid;

rel-(2R, 3S)-5,6-dichloro-3,4-dihydro-2-(trifluoromethyl)-2H-1-benzopyran-3-carboxylic acid;

(2S,3R)-6-chloro-3,4-dihydro-7-(1,1-dimethylethyl)-2-(trifluoromethyl)-2H-1-benzopyran-3-carboxylic acid;

rel-(2R,3 S)-3,4-dihydro-5,6,7-trichloro-2-(trifluoromethyl)-2H-1-benzopyran-3-carboxylic acid;

rel-(2R,3S)-3,4-dihydro-6,7,8-trichloro-2-(trifluoromethyl)-2H-1-benzopyran-3-carboxylic acid;

rel-(2R,3 S)-5,8-dichloro-3,4-dihydro-2-(trifluoromethyl)-2H-1-benzopyran-3-carboxylic acid;

(2S,3R)-6-chloro-3,4-dihydro-2-(trifluoromethyl)-2H-1-benzopyran-3-carboxylic acid;

rel-(2R,3 S)-6-cyano-3,4-dihydro-2-(trifluoromethyl)-2H-1-benzopyran-3-carboxylic acid; and rel-(2R,3S)-3,4-dihydro-6-trifluoromethoxy-2-(trifluoromethyl)-2H-1-benzopyran-3-carboxylic acid.

9. A method of treating or preventing a cyclooxygenase-2 mediated disorder in a subject, said method comprising treating the subject having or susceptible to said disorder with a therapeutically-effective amount of a compound of claims 1–8; or a pharmaceutically-acceptable salt thereof.

10. The method of claim 9 wherein the cyclooxygenase-2 mediated disorder is inflammation.

11. The method of claim 9 wherein the cyclooxygenase-2 mediated disorder is arthritis.

12. The method of claim 9 wherein the cyclooxygenase-2 mediated disorder is pain.

13. The method of claim 9 wherein the cyclooxygenase-2 mediated disorder is cancer.

14. A pharmaceutical composition comprising a therapeutically-effective amount of a compound, said compound selected from a family of compounds of claims 1–8; or a pharmaceutically-acceptable salt thereof.

15. A process for the preparation of compounds of compound of Formula I

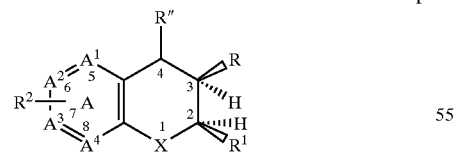

I wherein X is O;

wherein R is selected from carboxyl, aminocarbonyl, $C_1$–$C_6$-alkylsulfonylaminocarbonyl and $C_1$–$C_6$-alkoxycarbonyl;

wherein R" is selected from hydrido, phenyl, thienyl, $C_1$–$C_6$-alkyl and $C_2$–$C_6$-alkenyl;

wherein $R^1$ is selected from $C_1$–$C_3$-perfluoroalkyl, chloro, $C_1$–$C_6$-alkylthio, nitro, cyano and cyano-$C_1$–$C_3$-alkyl;

wherein $R^2$ is one or more radicals independently selected from hydrido, halo, $C_1$–$C_6$-alkyl, $C_2$–$C_6$-alkenyl, $C_2$–$C_6$-alkynyl, halo-$C_2$–$C_6$-alkynyl, aryl-$C_{1-C_3}$-alkyl, aryl-$C_2$–$C_6$-alkynyl, aryl-$C_2$–$C_6$-alkenyl, $C_1$–$C_6$-alkoxy, methylenedioxy, $C_1$–$C_6$-alkylthio, $C_1$–$C_6$-alkylsulfinyl, aryloxy, arylthio, arylsulfinyl, heteroaryloxy, $C_1$–$C_6$-alkoxy-$C_1$–$C_6$-alkyl, aryl-$C_1$–$C_6$-alkoxy, heteroaryl-$C_1$–$C_6$-alkoxy, aryl-$C_1$–$C_6$-alkoxy-$C_1$–$C_6$-alkyl, $C_1$–$C_6$-haloalkyl, $C_1$–$C_6$-haloalkoxy, $C_1$–$C_6$-haloalkylthio, $C_1$–$C_6$-haloalkylsulfinyl, $C_1$–$C_6$-haloalkylsulfonyl, $C_1$–$C_3$-(haloalkyl-$C_1$–$C_3$-hydroxyalkyl, $C_1$–$C_6$-hydroxyalkyl, hydroxyimino-$C_1$–$C_6$-alkyl, $C_1$–$C_6$-alkylamino, arylamino, aryl-$C_1$–$C_6$-alkylamino, heteroarylamino, heteroaryl-$C_1$–$C_6$-alkylamino, nitro, cyano, amino, aminosulfonyl, $C_1$–$C_6$-alkylaminosulfonyl, arylaminosulfonyl, heteroarylaminosulfonyl, aryl-$C_1$–$C_6$-alkylaminosulfonyl, heteroaryl-$C_1$–$C_6$-alkylaminosulfonyl, heterocyclylsulfonyl, $C_1$–$C_6$-alkylsulfonyl, aryl-$C_1$–$C_6$-alkylsulfonyl, optionally substituted aryl, optionally substituted heteroaryl, aryl-$C_1$–$C_6$-alkylcarbonyl, heteroaryl-$C_1$–$C_6$-alkylcarbonyl, heteroarylcarbonyl, arylcarbonyl, aminocarbonyl, $C_1$–$C_6$-alkoxycarbonyl, formyl, $C_1$–$C_6$-haloalkylcarbonyl and $C_1$–$C_6$-alkylcarbonyl; and wherein the A ring atoms $A^1$, $A^2$, $A^3$ and $A^4$ are carbon;

or wherein $R^2$ together with ring A forms a radical selected from naphthyl, quinolyl, isoquinolyl, quinolizinyl, quinoxalinyl and dibenzofuryl;

or an isomer or pharmaceutically acceptable salt thereof;

Said process comprising reducing a compound of Formula 41:

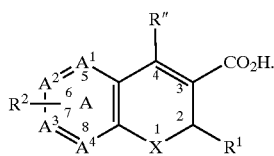

41

* * * * *